United States Patent
Dähne et al.

(10) Patent No.: US 10,688,033 B2
(45) Date of Patent: Jun. 23, 2020

(54) HAIR COLOURATION FORMULATION

(71) Applicant: Noxell Corporation, Hunt Valley, MD (US)

(72) Inventors: Lars Siegfried Dähne, Berlin (DE); Gabriella Egri, Berlin (DE); Mandy Hecht, Falkensee (DE); Mathias Kurt Herrlein, Kronberg (DE); Moritz Klickermann, Berlin (DE); Bryan Patrick Murphy, Loveland, OH (US); Monica Jo Patten, Jeannette, PA (US); Tatjana Schaefer, Schwalbach (DE); Stephen Robert Schofield, Egham Surrey (GB); Cagri Üzüm, Berlin (DE); Ingo Reinhold Weber, Schwalbach am Taurus (DE)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 16/096,164

(22) PCT Filed: Apr. 25, 2017

(86) PCT No.: PCT/US2017/029351
§ 371 (c)(1),
(2) Date: Oct. 24, 2018

(87) PCT Pub. No.: WO2017/189539
PCT Pub. Date: Nov. 2, 2017

(65) Prior Publication Data
US 2019/0133912 A1    May 9, 2019

Related U.S. Application Data

(60) Provisional application No. 62/326,946, filed on Apr. 25, 2016.

(51) Int. Cl.
*A61Q 5/10* (2006.01)
*A61K 8/81* (2006.01)
(Continued)

(52) U.S. Cl.
CPC ............... *A61K 8/817* (2013.01); *A61K 8/73* (2013.01); *A61K 8/733* (2013.01); *A61K 8/8117* (2013.01);
(Continued)

(58) Field of Classification Search
CPC ........ A61Q 5/065; A61Q 5/10; A61K 8/8152; A61K 8/817; A61K 8/8158; A61K 8/8147; A61K 8/8117; A61K 2800/434
See application file for complete search history.

(56) References Cited

U.S. PATENT DOCUMENTS 4,182,612 A * 1/1980 Sokol ............... A61K 8/355
525/359.2
4,228,259 A * 10/1980 Kalopissis ............ A61K 8/88
525/435

(Continued)

FOREIGN PATENT DOCUMENTS

EP    3015134 A1    5/2016
EP    3015135 A1    5/2016
(Continued)

OTHER PUBLICATIONS

"International Application Serial No. PCT US2017 029351, International Preliminary Report on Patentability dated Nov. 8, 2018", 7 pgs.

(Continued)

*Primary Examiner* — Eisa B Elhilo
(74) *Attorney, Agent, or Firm* — Schwegman Lundberg & Woessner, P.A.

(57) ABSTRACT

Formulation for colouring hair having at least one coloured polymer.

11 Claims, 6 Drawing Sheets

(51) Int. Cl.
  *A61Q 5/06* (2006.01)
  *A61K 8/84* (2006.01)
  *A61K 8/73* (2006.01)

(52) U.S. Cl.
  CPC .............. *A61K 8/8147* (2013.01); *A61K 8/84* (2013.01); *A61Q 5/065* (2013.01); *A61K 2800/434* (2013.01)

(56) References Cited

U.S. PATENT DOCUMENTS

2011/0061179 A1* 3/2011 Cremer ................ A61K 8/8152
  8/407
2012/0328550 A1 12/2012 De Boni et al.

FOREIGN PATENT DOCUMENTS

FR   2882929 A1   9/2006
WO   WO-2017189539 A1   11/2017

OTHER PUBLICATIONS

"International Application Serial No. PCT/US2017/029351, International Search Report dated Jun. 22, 2017", 4 pgs.
"International Application Serial No. PCT/US2017/029351, Written Opinion dated Jun. 22, 2017", 5 pgs.
"European Application Serial No. 17722276.7, Communication Pursuant to Article 94(3) EPC dated Dec. 10, 2019", 4 pgs.
"European Application Serial No. 17722276.7, Response filed Jun. 3, 2019 to Communication Pursuant to Rules 161(1) and 162 EPC", w/ English Claims, 15 pgs.

* cited by examiner

HAIR COLOURATION FORMULATION

PRIORITY APPLICATION

This application is a U.S. National Stage Filing under 35 U.S.C. 371 from International Application No. PCT/US2017/029351, filed on Apr. 25, 2017, and published as WO 2017/189539 on Nov. 2, 2017, which claims the benefit of priority to U.S. Provisional Application No. 62/326,946, filed on Apr. 25, 2016, which application is incorporated by reference herein in its entirety.

FIELD OF THE INVENTION

The invention relates to a hair colouring formulation for providing a single or a multilayer structure on an area of hair. The formulation can include a first and a second composition. The first composition can include at least one cationic polymer and the second composition can include at least one anionic polymer. The invention further relates to a method for colouring hair by applying the hair colouring formulation, and to the use of the hair colouring formulation for providing a single or a multilayer structure on an area of hair and/or for controlling the colour intensity of hair. The hair colouration which is obtained according to the method of the present invention is particularly advantageous in term of washfastness, stability and tailoring of the colour result.

BACKGROUND OF THE INVENTION

Different systems and methods for changing the natural colour of hair are known in the art. These systems and methods involve the use of hair colouring compositions which allow either permanent or temporary change of hair colour. Hair colouring compositions which are used to permanently change the colour of hair, also called oxidative hair colouring compositions, typically comprise oxidative hair dye precursors, which can diffuse into the hair through the cuticle and into the cortex where they then react with each other and with a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may be irritating for the scalp of the user, especially when such a process is repeated regularly and the compositions which are usually used have an undesirable odour. Furthermore, obtaining the desired colour result is not easy since standard oxidative hair colouring compositions are reactive compositions and it is therefore not easy to control the reaction on hair.

Alternatively, systems and methods for temporarily changing the colour of hair have also been developed. These systems and methods usually involve the application of hair colouring compositions comprising direct dyes. Direct dye compositions are usually less aggressive for the hair in that they are non reactive compositions. However, the problem with these compositions is that the hair colouration which is obtained is typically characterized by a weaker washfastness than when the hair is coloured with standard oxidative hair colouring compositions, especially when the hair is washed with standard shampoo compositions. A further problem with direct dyes is that since direct dyes are low molecular weight molecules, they may have the tendency to also colour the scalp of the user.

Therefore, there is still the need for a hair colouring formulation and a method for providing the hair with the desired colour result and colour intensity in an easy manner. There is also the need for a hair colouring formulation and a method providing a hair colouration which is characterized by a better stability and good washfastness. Furthermore, there is also the need for a hair colouring formulation and a method involving the use of hair colouring compositions which are less aggressive for the hair and for the scalp. Finally, there is also the need for a hair colouring formulation and a method using compositions which are less smelly.

SUMMARY OF THE INVENTION

The present invention relates to a hair colouring formulation, such as a hair colouring formulation, for providing a single or a multilayer hair colouring structure on an area of hair. The hair colouring formulation may include a coloured polymer selected from the group consisting of:
  a coloured cationic polymer formed by a cationic polymer backbone and at least a cationic chromophore linked to the cationic polymer backbone;
  a coloured cationic polymer formed by a cationic polymer backbone and at least an anionic chromophore linked to the cationic polymer backbone;
  a coloured cationic polymer formed by a cationic polymer backbone and at least a non-ionic chromophore linked to the cationic polymer backbone;
  a coloured cationic polymer formed by a cationic polymer backbone and at least an amphoteric chromophore linked to the cationic polymer backbone;
  a coloured cationic polymer formed by a cationic polymer backbone and at least a cationic fluorophore linked to the cationic polymer backbone;
  a coloured cationic polymer formed by a cationic polymer backbone and at least an anionic fluorophore linked to the cationic polymer backbone;
  a coloured cationic polymer formed by a cationic polymer backbone and at least a non-ionic fluorophore linked to the cationic polymer backbone;
  a coloured cationic polymer formed by a cationic polymer backbone and at least an amphoteric fluorophore linked to the cationic polymer backbone;
  a coloured anionic polymer formed by a anionic polymer backbone and at least a cationic chromophore linked to the anionic polymer backbone;
  a coloured anionic polymer formed by a anionic polymer backbone and at least an anionic chromophore linked to the anionic polymer backbone;
  a coloured anionic polymer formed by a anionic polymer backbone and at least a non-ionic chromophore linked to the anionic polymer backbone;
  a coloured anionic polymer formed by a anionic polymer backbone and at least an amphoteric chromophore linked to the anionic polymer backbone;

a coloured anionic polymer formed by a anionic polymer backbone and at least a cationic fluorophore linked to the anionic polymer backbone;

a coloured anionic polymer formed by a anionic polymer backbone and at least an anionic fluorophore linked to the anionic polymer backbone;

a coloured anionic polymer formed by a anionic polymer backbone and at least a non-ionic fluorophore linked to the anionic polymer backbone;

a coloured anionic polymer formed by a anionic polymer backbone and at least an amphoteric fluorophore linked to the anionic polymer backbone; and any combinations thereof.

The present invention also relates to a polymeric hair colouring formulation, which includes at least two different chromophores and/or fluorophores linked to polymer(s), and optionally one or more uncoloured polymer(s).

The present invention also relates to a method for colouring hair comprising applying any of the above mentioned coloured polymers to hair.

The present invention also relates to a method for manufacturing a polymeric hair colouring formulation.

The present invention also relates to a use of a polymeric hair colouring formulation.

MODES OF THE INVENTION

Figure 1:
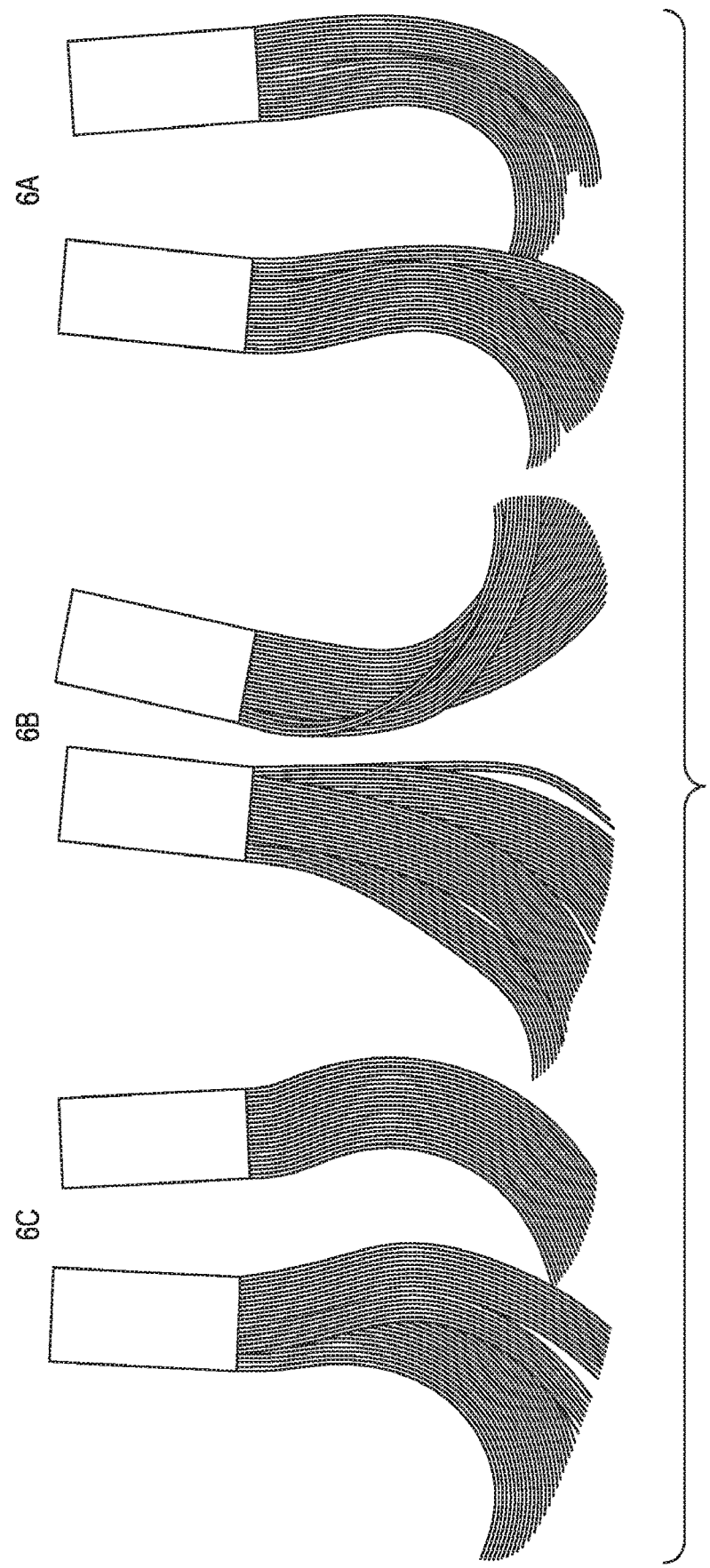
FIG. 1 illustrates samples prepared according to an embodiment of the invention, wherein different chromophores were linked to the same polymer backbone.

In the following, general embodiments of the invention are described without being limited thereto.

Polymeric Hair Colouring Formulation with Different Chromophores and/or Fluorophores According to an embodiment, a polymeric hair colouring formulation includes at least two different chromophores and/or fluorophores linked to polymer(s), and optionally one or more uncoloured polymer(s).

The different chromophores and/or fluorophores can be linked to the polymer-backbone of the same polymer(s) or to the polymer-backbones of different polymer(s). The different polymer(s), i.e. coloured polymer(s) can be of the same type and can be mixed to form a common polymeric layer.

The different polymer(s), i.e. different coloured polymer(s) can also form separate polymeric layers.

A Method for Manufacturing a Polymeric Hair Colouration Composition for Hair Coloration According to an embodiment, a method for manufacturing a polymeric hair colouration composition for hair coloration is provided, the method includes:

providing at least first and second polymer(s) each having a polymer back-bone;

linking at least a first chromophore and/or a first fluorophore to the polymer back-bone of the first polymer(s) to form a first composition comprising first coloured polymer(s);

linking at least a second chromophores and/or a second fluorophores to the polymer back-bone of the second polymer(s) to form a second composition comprising second coloured polymer(s); and mixing the first and second composition to form the polymeric hair colouration composition, wherein the first and second polymer(s) both are either anionic or cationic.

According to an embodiment, a method for manufacturing a polymeric hair colouration composition for hair coloration is provided, the method includes providing at least one of anionic polymer(s) and cationic polymer(s); and linking at least two different chromophores and/or fluorophores to the at least one of anionic polymer(s) and cationic polymer(s).

Use of a Polymeric Hair Colouration Formulation to Provide Hair Colouration

According to an embodiment, a use of a polymeric hair colouration formulation to provide hair colouration is provided, wherein the polymeric hair colouration formulation includes at least one of:

a first composition comprising one or more polymer(s) to which at least two different chromophores and/or fluorophores are linked;

a first composition comprising a mixture of at least first polymer(s), to which at least a first chromophore and/or a first fluorophore is linked, and at least second polymer(s) to which at least a second chromophore and/or second fluorophores different to the first chromophore and/or first fluorophore is linked, wherein the first and second polymer(s) are both either anionic or cationic; and a first composition comprising at least first polymer(s), to which at least a first chromophore and/or a first fluorophore is linked, and a second composition comprising at least second polymer(s) to which at least a second chromophore and/or second fluorophores different to the first chromophore and/or first fluorophore is linked.

Coloured Cationic Polymer with High Labelling Degree—Optional Anionic Polymer

According to an embodiment, a hair colouring system, such as a hair colouring formulation, for providing a single or a multilayer hair colouring structure on an area of hair, includes:

a first composition comprising at least one coloured cationic polymer, wherein the coloured cationic polymer is formed by a cationic polymer, and at least one chromophore and/or at least one fluorophore linked to the cationic polymer with a given labelling degree k, wherein the labelling degree k defined as n:m is from 1:2 to 1:1000, particularly from 1:3 to 1:500, more particularly from 1:3 to 1:100, more particularly from 1:3 to 1:15, and even more particularly from 1:3 to 1:9, with n being the number of chromophores and/or fluorophores molecules per polymer and m being the monomeric units per polymer, and an optionally second composition comprising at least one anionic polymer.

The labelling degree can also be from 20:100 to 90:200, particularly from 30:100 to 60:100 if a less intense colouration is desired.

According to an embodiment, the chromophore and/or the fluorophore can be anionic, cationic, non-ionic, or amphoteric.

According to an embodiment, a method for colouring hair includes:
a) carrying out the following sequence of steps:
    (i) applying a first composition comprising at least one coloured cationic polymer to a first portion of hair, wherein the coloured cationic polymer is formed by
        a cationic polymer, and
        at least one chromophore and/or at least one fluorophore linked to the cationic polymer with a given labelling degree k, wherein the labelling degree k defined as n:m is from 1:2 to 1:1000, particularly from 1:3 to 1:500, more particularly from 1:3 to 1:100, more particularly from 1:3 to 1:15, and even more particularly from 1:3 to 1:9, with n being the number of chromophores and/or fluorophores molecules per polymer and m being the monomeric units per polymer; and
    (ii) optionally applying a second composition comprising at least one anionic polymer to a second portion of the hair;
    the first and the second portions of the hair having at least one common area;
    and optionally
b) repeating step a) at least once, wherein the common area of each of the repeated steps a) has at least one common area with:
    the common area of step a); and
    the common area of each of the other repeated steps a) in case step a) is repeated more than once.

Any other labelling degree as mentioned above can be used. Furthermore, any of the above types of chromophores and/or fluorophores (cationic, anionic, non-ionic or amphoteric) can be used.

Coloured Cationic Polymer with Low Labelling Degree—Optional Anionic Polymer

According to an embodiment, a hair colouring system, such as a hair colouring formulation, for providing a single or a multilayer hair colouring structure on an area of hair, includes:
a first composition comprising at least one coloured cationic polymer, wherein the coloured cationic polymer is formed by
    a cationic polymer, and
    at least one chromophore and/or at least one fluorophore linked to the cationic polymer with a given labelling degree k, wherein the labelling degree k defined as n:m is from 1:1,000 to 1:1000,000, particularly between 1:1,100 to 1:100,000, more particularly between 1:1,200 to 1:10,000, with n being the number of chromophores and/or fluorophores molecules per polymer and m being the monomeric units per polymer,
and an optionally second composition comprising at least one anionic polymer.

The labelling degree can also be from 1:2,000 to 1:100,000, particularly from 1:3,000 to 1:30,000.

According to an embodiment, the chromophore and/or the fluorophore can be anionic, cationic, non-ionic, or amphoteric.

Still further, according to an embodiment, a method for colouring hair includes:
a) carrying out the following sequence of steps:
    (i) applying a first composition comprising at least one coloured cationic polymer to a first portion of hair, wherein the coloured cationic polymer is formed by
        a cationic polymer, and
        at least one chromophore and/or at least one fluorophore linked to the cationic polymer with a given labelling degree k, wherein the labelling degree k defined as n:m is from 1:1,000 to 1:1000,000, particularly from 1:1,100 to 1:100,000, more particularly from 1:1,200 to 1:10,000, with n being the number of chromophores and/or fluorophores molecules per polymer and m being the monomeric units per polymer; and
    (ii) optionally applying a second composition comprising at least one anionic polymer to a second portion of the hair, wherein the first and the second portions of the hair having at least one common area;
    and optionally
b) repeating step a) at least once, wherein the common area of each of the repeated steps a) has at least one common area with:
    the common area of step a); and
    the common area of each of the other repeated steps a) in case step a) is repeated more than once.

Any other labelling degree as mentioned above can be used. Furthermore, any of the above types of chromophores and/or fluorophores (cationic, anionic, non-ionic or amphoteric) can be used.

Coloured Cationic Polymer—Anionic Polymer—Coloured Cationic Polymer with Different Labelling Degrees According to an embodiment, a hair colouring system, such as a hair colouring formulation, for providing a multilayer hair colouring structure on an area of hair, includes:
a first composition comprising at least one coloured cationic polymer which is formed by
    a cationic polymer, and
    at least one chromophore and/or at least one fluorophore linked to the cationic polymer with a labelling degree k1,
a second composition comprising at least one anionic polymer; and
a third composition comprising at least one coloured cationic polymer which is formed by
    a cationic polymer, and
    at least one chromophore and/or at least one fluorophore linked to the cationic polymer with a labelling degree k3, wherein the labelling degree k1 of the coloured cationic polymer of the first composition is different to the labelling degree k3 of the coloured cationic polymer of the third composition.

The labelling degree k1 can be higher than the labelling degree k3 meaning the coloured cationic polymer of the first composition has more chromophore and/or fluorophore molecules per polymer than the coloured cationic polymer of the third composition. For example, the labelling degree k1 can be at least two times higher than the labelling degree k3. A specific example is a labelling degree k1 from 1:3 to 1:10, and a labelling degree k3 from 1:8 to 1:30. The different labelling degrees can be beneficial for hair colouration shading, for example when the chromophores and/or the fluorophores of the first and third compositions are different.

According to an embodiment, the anionic polymer can be uncoloured, i.e. that no chromophore and/or fluorophore is linked to the anionic polymer.

According to an embodiment, the coloured cationic polymer of the first composition includes a chromophore and/or fluorophore different to the chromophore and/or fluorophore of the coloured cationic polymer of the third composition.

When using different chromophores and/or the fluorophores for the first and third composition, the order of application of the respective compositions may result in a different overall hair colouration. The overall visual impression of the hair colouration when applying the first composition prior to the third composition can be different to the visual impression when applying the third composition before the first composition. The second composition having the anionic polymer is applied in between.

A different labelling degree can also improve the evenness of the hair colouration. Typically, the first composition is applied first, followed by the second and finally the third composition to form the multilayer hair colouring structure. The coloured cationic polymer of the third composition thus forms, relative to the hair, an outer layer which partially or fully covers the anionic polymer and the coloured cationic polymer of the first composition. The first composition may give a base colouration which may be uneven depending on the actual condition of the hair. The additional third composition provides a further coloured cationic polymer for the outer coloured layer of the multilayer hair colouring structure, which outer layer can be less intense than the inner coloured layer to provide a more even overall colouration.

According to an embodiment, the labelling degrees $k1$ and $k3$ can be in any of the above mentioned ranges with the labelling degree $k1$ higher than the labelling degree $k3$. For example, the labelling degree $k1$ can be from 1:2 to 1:100, particularly from 1:3 to 1:15, and more particularly from 1:3 to 1:9. The labelling degree $k3$ can be from 20:100 to 90:100, particularly from 30:100 to 60:100.

According to an embodiment, the labelling degree $k1$ can also be lower than 1:1,000 such as from 1:1,100 to 1:1000,000, particularly from 1:1,200 to 1:10,000. The labelling degree $k3$ can be 1 from 1:2,000 to 1:1000,000, particularly from 1:5,000 to 1:30,000. Such low labelling degrees are typically used for fluorophores.

According to an embodiment, the any one of the coloured cationic polymers of the first and third compositions can include a fluorophore with a lower labelling degree while the other one of the coloured cationic polymers of the first and third compositions can include a chromophore with a higher labelling degree. Since fluorophores typically produce a higher visual effect, their labelling degree can be lower than the labelling degree for the chromophores. It is, however, also possible to provide the fluorophores with a higher labelling degree than the chromophores.

According to an embodiment, the coloured cationic polymer of the first composition can include a chromophore with the labelling degree $k1$ and the coloured cationic polymer of the third composition can include a fluorophore with the labelling degree $k3$. The labelling degree $k1$ can be higher than the labelling degree $k3$. For example, the labelling degree $k1$ can be in a range higher than 1:1,100 such as from 1:5 to 1:500, more particularly from 1:10 to 1:200, and the labelling degree $k3$ can be in a range lower than 1:1,000 such as from 1:2,000 to 1:100,000, and more particularly from 1:5,000 to 1:100,000.

According to an embodiment, the coloured cationic polymer of the first composition can include a fluorophore with the labelling degree $k1$ and the coloured cationic polymer of the third composition can include a chromophore with the labelling degree $k3$. The labelling degree $k1$ can be lower than the labelling degree $k3$. For example, the labelling degree $k3$ can be in a range higher than 1:1,100 such as from 1:5 to 1:500, more particularly from 1:10 to 1:200, and the labelling degree $k1$ can be in a range lower than 1:1,000 such as from 1:2,000 to 1:100,000, and more particularly from 1:5,000 to 1:100,000.

According to an embodiment, the type of the chromophore and/or of the fluorophore for the coloured cationic polymers of the first and third compositions is different.

According to an embodiment, the chromophore and/or fluorophore of the coloured cationic polymer of the first composition can be cationic, while the chromophore and/or fluorophore of the coloured cationic polymer of the third composition can be anionic. According to another embodiment, the chromophore and/or fluorophore of the coloured cationic polymer of the first composition can be anionic, while the chromophore and/or fluorophore of the coloured cationic polymer of the third composition can be cationic. According to yet another embodiment, the chromophore and/or fluorophore of the coloured cationic polymer of the first composition can be cationic and/or anionic, while the chromophore and/or fluorophore of the coloured cationic polymer of the third composition can be non-ionic or amphoteric. According to yet another embodiment, the chromophore and/or fluorophore of the coloured cationic polymer of the first composition can be non-ionic or amphoteric, while the chromophore and/or fluorophore of the coloured cationic polymer of the third composition can be cationic and/or anionic.

According to an embodiment, the type of the chromophore and/or of the fluorophore for the coloured cationic polymers of the first and third compositions is the same but different chromophores and/or fluorophore are linked to the respective cationic polymers.

According to an embodiment, a method for colouring hair includes:

a) carrying out the following sequence of steps:
  (i) applying a first composition comprising at least one coloured cationic polymer to a first portion of hair, wherein the coloured cationic polymer comprises
    a cationic polymer, and
    at least one chromophore and/or at least one fluorophore linked to the cationic polymer with a labelling degree $k1$;
  (ii) applying a second composition comprising at least one anionic polymer to a second portion of the hair; the first and the second portions of the hair having at least one common area; and
  (iii) applying a third composition comprising at least one coloured cationic polymer to a third portion of hair, wherein the coloured cationic polymer comprises
    a cationic polymer, and
    at least one chromophore and/or at least one fluorophore linked to the cationic polymer with a labelling degree $k3$;
  and
  (iv) optionally applying a fourth composition comprising at least one anionic polymer to a fourth portion of the hair;
  wherein the first, second, third and fourth portions of the hair having at least one common area.

The labelling degrees $k1$ and $k3$ can be in the above mentioned ranges.

Coloured Cationic Polymer—Coloured Anionic Polymer

According to an embodiment, a hair colouring system, such as a hair colouring formulation, for providing a multilayer hair colouring structure on an area of hair, the system includes:
- a first composition comprising at least one coloured cationic polymer which is formed by
  - a cationic polymer, and
  - at least one chromophore and/or at least one fluorophore linked to the cationic polymer with a labelling degree k1, and
- a second composition comprising at least one coloured anionic polymer which is formed by
  - an anionic polymer, and
  - at least one chromophore and/or at least one fluorophore linked to the anionic polymer with a labelling degree k2, wherein the labelling degree k1 of the coloured anionic polymer of the first composition is different to the labelling degree k2 of the coloured anionic polymer of the second composition.

The labelling degree k1 can be higher than the labelling degree k2. For example, the labelling degree k1 can be at least two-times higher, more particularly at least three-times than the labelling degree k2. A specific example is a labelling degree k1 from 1:3 to 1:10, and a labelling degree k2 from 1:8 to 1:30. The different labelling degrees can be beneficial for hair colouration shading, for example when the chromophores and/or the fluorophores of the first and third compositions are different.

According to an embodiment, the coloured cationic polymer of the first composition includes a chromophore and/or fluorophore different to the chromophore and/or fluorophore of the coloured anionic polymer of the second composition.

According to an embodiment, the type of the chromophore and/or of the fluorophore for the coloured cationic polymers of the first and second compositions is different as described above.

According to an embodiment, the type of the chromophore and/or of the fluorophore for the coloured cationic polymers of the first and second compositions is the same but different chromophores and/or fluorophore are linked to the respective polymers.

According to an embodiment, the labelling degrees k1 and k2 can be in any of the above mentioned ranges. For example, the labelling degree k1 can from 1:2 to 1:100, particularly from 1:3 to 1:15, and more particularly from 1:3 to 1:9. The labelling degree k2 can be from 20:100 to 90:100, particularly from 30:100 to 60:100.

According to an embodiment, the labelling degree k1 can also be lower than 1:1,000 such as from 1:1,100 to 1:1000,000, particularly from 1:1,200 to 1:10,000. The labelling degree k2 can be 1 from 1:2,000 to 1:1000,000, particularly from 1:5,000 to 1:30,000. Such low labelling degrees are typically used for fluorophores.

According to an embodiment, the coloured cationic polymer of the first composition can include a chromophore with the labelling degree k1 and the coloured anionic polymer of the third composition can include a fluorophore with the labelling degree k2. For example, the labelling degree k1 can be higher than the labelling degree k2. For example, k1 can be in a range higher than 1:1,100 such as from 1:5 to 1:500, more particularly from 1:10 to 1:200, and the labelling degree k2 can be in a range lower than 1:1,000 such as from 1:2,000 to 1:100,000, and more particularly from 1:5,000 to 1:100,000.

According to an embodiment, the coloured cationic polymer of the first composition can include a fluorophore with the labelling degree k1 and the coloured anionic polymer of the second composition can include a chromophore with the labelling degree k2. For example, the labelling degree k1 can be lower than the labelling degree k2. For example, k2 be in a range higher than 1:1,100 such as from 1:5 to 1:500, more particularly from 1:10 to 1:200, and the labelling degree k1 can be in a range lower than 1:1,000 such as from 1:2,000 to 1:100,000, and more particularly from 1:5,000 to 1:100,000.

According to an embodiment, a method for colouring hair includes:
b) carrying out the following sequence of steps:
  (i) applying a first composition comprising at least one coloured cationic polymer to a first portion of hair, wherein the coloured cationic polymer comprises
    a cationic polymer, and
    at least one chromophore and/or at least one fluorophore linked to the cationic polymer with a labelling degree k1;
  (ii) applying a second composition comprising at least one coloured anionic polymer to a second portion of the hair, wherein the first and the second portions of the hair have at least one common area, and wherein
    a anionic polymer, and
    at least one chromophore and/or at least one fluorophore linked to the anionic polymer with a labelling degree k2;
  and
  (iii) optionally applying a third composition comprising at least one cationic polymer to a third portion of the hair;
  wherein the first, second, and third portions of the hair having at least one common area.

The labelling degrees k1 and k2 can be in the above mentioned ranges.

According to an embodiment, the present invention relates to the use of the hair colouring system for providing a multilayer structure on an area of hair and/or for controlling the colour intensity of hair.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention.

All ratios or percentages are weight ratios or weight percentages unless specifically stated otherwise.

By "hair colouring system" it is meant any system, formulation, article, product which is suitable for changing the colour result and/or colour intensity of hair.

By "multilayer structure" it is meant that at least two polymeric layers are placed on hair on top of each other by alternating the deposition of a first polymeric layer and a second polymeric layer, thereby forming a layer-by-layer structure.

By "an area of hair" it is meant at least a portion of hair including only a small portion of one single hair up to the complete hair of head.

By "cationic polymer" it is meant any polymer comprising an overall charge at full protonation which is positive.

By "coloured cationic polymer" it is meant any cationic polymer comprising at least one chromophore and/or at least one fluorophore either in the skeleton or as pendent group.

By "uncoloured cationic polymer" it is meant any cationic polymer which does not comprise any chromophore or fluorophore either in the skeleton or as pendent group.

By "polymeric backbone" it is meant any series of covalently bound atoms that together create the continuous chain of a molecule, including the main chain and all other pendant chains.

By "homopolymer" it is meant any polymer that contains only a single type of repeat unit.

By "heteropolymer" it is meant any polymer that contains a mixture of at least two different repeat units.

As used herein the expression "labelling degree k" is a measure for the loading of a polymer with a dye. The "labelling degree k" is defined as n:m, with n being the number of chromophores and/or fluorophores per polymer and m being the monomeric units per polymer.

A "higher labelling degree" means more chromophore and/or fluorophore molecules per polymer. For example, a labelling degree 1:20 is higher than a labelling degree 1:100. A "lower labelling degree" means less chromophore and/or fluorophore molecules per polymer. For example, a labelling degree 1:30 is lower than a labelling degree 1:5.

By "anionic polymer" it is meant any polymer comprising an overall charge at full deprotonation which is negative.

By "coloured anionic polymer" it is meant any anionic polymer comprising at least one chromophore and/or at least one fluorophore either in the skeleton or as pendent group.

By "uncoloured anionic polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "linked to the polymer" it is meant a covalent bond between the chromophore and/or the fluorophore with the polymer.

By "type of chromophore and/or fluorophore" it is meant whether the chromophore and/or of the fluorophore is cationic, anionic, non-ionic, or amphoteric.

Hair Colouring System

Embodiments of the present invention relate to a hair colouring system for providing a multilayer structure on an area of hair. The system comprises:
  a first composition comprising at least one coloured cationic polymer, wherein the coloured cationic polymer comprises
    a cationic polymer, and
    at least one chromophore and/or at least one fluorophore linked to the cationic polymer.

The labelling degree k of the coloured cationic polymer defined as n:m may be between 1:2 to 1:100, with n being the number of chromophores and/or fluorophores per polymer and m being the monomeric units per polymer.

The system further may comprise a second composition comprising at least one anionic polymer.

The system according to the present invention is particularly advantageous. For instance, the system is particularly suitable for providing a multilayer structure on an area of hair.

In its smallest version, the multilayer structure merely consists of two polymeric layers, the first polymeric layer being placed on top of the outer layer of natural hair, the second polymeric layer being placed on top of the first polymeric layer. More specifically, the coloured cationic polymer of the first composition is capable of binding to the negatively charged outer layer of the natural hair via ionic linkage. Accordingly, the anionic layer of the second composition is capable of binding to the coloured cationic polymer via ionic linkage. Thereby, a bilayer on hair is formed consisting of a coloured cationic polymer layer covering the outer hair layer followed by an anionic layer covering the coloured cationic polymer layer. Of course, the multilayer structure is not only restricted to the above-described bilayer structure. In fact, the multilayer structure can comprise x coloured cationic polymer layers and y anionic layers in alternating sequence, with x and y, independent from each other, being 1, 2, 3, 4, 5, 6, 7, 8, 9 or 10. In "alternating sequence" means that two layers of the same ionic type typically cannot lie next to each other.

For instance, the multilayer structure can comprise two coloured cationic polymer layers and two anionic layers in alternating sequence. The multilayer structure can also comprise three coloured cationic polymer layers and three anionic layers in alternating sequence. Alternatively, the multilayer structure can comprise four coloured cationic polymer layers and four anionic layers in alternating sequence. The total number of polymeric layers with the multilayer structure may be even or odd. For instance, the multilayer structure can comprise two coloured cationic polymer layers and only one anionic layer in alternating sequence, thereby providing the outer layer of the coated hair with a cationic structure. A cationic structure of the outer layer can provide the user with a good hair feeling which is similar to what is obtained when standard commercially available conditioners are applied to the hair.

The advantageous multilayer structure can be achieved by applying the first composition comprising at least one coloured cationic polymer before applying the second composition comprising at least one anionic polymer and optionally repeating this procedure until the desired a multilayer structure is obtained.

Since the coloured cationic polymer(s) and the anionic polymer(s) of the multilayer structure are high molecular weight molecules, they usually do not diffuse into the hair or at least only to a limited extent when compared with dyes used in standard oxidative hair colouring methods for permanent change of hair colour. Moreover, they do not colour the scalp of the user, as direct dyes usually do.

Controlling the number of coloured cationic and anionic polymeric layers within the multilayer structure enables a better control on the final colour result and colour intensity by the user. By increasing the number of layers which are applied to the hair it is possible to obtain hair colorations having increased colour intensity. The user may decide on how many times the sequence of steps should be repeated and therefore have a better control over the colour result which is obtained on hair. The user may further decide on which parts of the hair of head have greater/weaker colour intensity than other parts.

Furthermore, in case the anionic polymer which is comprised in the second composition is the outer layer of the multilayer structure, an electrostatic structure is provided which is similar to the one of the outer layer of natural hair, i.e. a negatively charged surface. Therefore it is possible to apply standard cationic conditioners to the hair after the hair colouring process.

The presence of the anionic layer is further essential in order to have the possibility of applying a subsequent cationic layer on top of it when a multilayer of more than two polymeric layers is desired. While not wishing to be bound by theory it is also believed that in some embodiments, the anionic polymeric layer may act as a protective layer for the coloured cationic layer which is placed underneath and therefore may contribute to the good washfastness of the hair coloration. Contrary thereto, when using direct dyes, the hair colouration which is obtained is typically characterized by a weaker washfastness, especially when the hair is washed with standard shampoo compositions.

Furthermore, the compositions which are used in the system according to the present invention are particularly advantageous since—contrary to standard oxidative hair colouring compositions—these compositions are typically odourless.

As such, the hair colouration which is obtained by the system of the invention is particularly advantageous in terms of washfastness, stability and tailoring of the colour result. Specifically, based on the identity of chromophores and/or fluorophores attached to the cationic polymer, and particularly based on the degree to which the cationic polymer is labelled (i.e. the labelling degree), the user can achieve colours from pastel to intense, without hair damage. These coloured complexes show enhanced stability to cosmetic treatments and mechanical abrasion compared to the cationic polymer alone on hair.

These advantageous effects are unique since current hair colouring systems require deposition of the colour inside the hair to achieve any type of lastingness, particularly resistance to mechanical removal, shampoo fading and water bleed. However, such a deposition on the hair surface leads to a coated feel, and this coating is removed easily by mechanical abrasion.

Most attempts at surface colouring of hair fibres with coloured polymers have relied on exploitation of the negative surface charge on hair, particularly by attaching cationic chromophores to a polymer to enhance the attraction of the coloured polymer to hair. However, this results in over- or under-deposition of the colour depending on the level of surface charge of the hair, driven by fibre damage from previous cosmetic treatments and environmental factors.

With the system of the invention, the opportunity is given to tailor the colour effects and intensity. By the specific choice of various chromophores and/or fluorophores (anionic, cationic, amphoteric, or non-ionic) and their specific distribution (i.e. the specific labelling degree) on the cationic polymer (i.e. the polymer backbone), it is possible to avoid the above described problems and to deliver colours ranging from pastels to intense.

In the system described herein, the chromophores and/or fluorophores are covalently linked to a cationic polymer having e.g. primary amines that binds electrostatically to the hair surface. The extent of deposition in a single treatment is driven by the nascent charge of the cationic polymer at the pH of the hair surface, which is a function of damage. From that starting point, the overall charge of the coloured cationic polymer can be tailored by firstly choosing specific chromophores and/or fluorophores that are anionic, non-ionic, amphoteric, or cationic (depending on the desired colour, behaviour in wet atmosphere etc.), and by secondly choosing the ideal labelling degree for these specific chromophores and/or fluorophores. Subsequent treatments with an oppositely charged polymer partner (i.e. an anionic polymer), results in a complex that is more resistant to removal by water, shampoo, or mechanical forces.

With current technologies, when a chromophore is attached to a polymer, it is inherently more difficult to get pastel or light shades that are even. Using a lower concentration of the coloured polymer, as one possibly would for a monomeric dye formulation, can lead to patchy or uneven colour, because the polymer will first seek the more highly charged areas of the hair. By tailoring specific concentrations of the chromophores and/or fluorophores on the polymer backbone, even colours of all intensities are possible. This is best accomplished by the system according to embodiments using cationic polymers labelled with dyes (i.e. chromophores/and or fluorophores) that result in a balanced interaction with the fibres and that can be prepared reproducibly at a specific labelling degree from very dilute to exhaustive labelling, depending on the type of dyes used. Finally, the ability to tailor the colour intensity of the polymer gives users (i.e. colourists and consumers) the ability to generate currently impossible colour effects by application of differently coloured layers individually without the drawback of e.g., obtaining over-deposition of colour or colour build-up.

Coloured Cationic Polymer

The coloured cationic polymer which is comprised in the first composition comprises a cationic polymer, and at least one chromophore and/or at least one fluorophore.

The cationic polymer is the polymeric backbone of the coloured cationic polymer and may be a cationic homopolymer or a cationic heteropolymer. The cationic polymers may be linear or branched.

The cationic polymer according to the present invention may comprise cationic and anionic monomeric units as long as the overall charge at full protonation is positive. As such, the following applies: $C_1 > C_2$, with $C_1$ being the total number of cationic charges and $C_2$ being the total number of anionic charges within one cationic polymer at full protonation.

The cationic polymer may comprise at least one monomer unit, i.e. one or more monomer unit(s), comprising at least one, i.e. one or more, amino functional group(s). The amino functional group(s) may be selected from the group consisting of primary, secondary, tertiary, quaternary amino functional groups and mixtures thereof. Alternatively, the amino functional group may be selected from the group consisting of primary, secondary amino functional groups and mixtures thereof. Alternatively, the amino functional group may be selected from secondary amino functional groups.

The cationic polymer may have a charge density at full protonation of at least 0.3, alternatively at least 0.6, alternatively at least 0.8, alternatively at least 1.0 positive charges per monomer unit.

The cationic polymer may have a weight average molecular weight of more than 0.5 kDa, alternatively from 0.5 to 5000 kDa, alternatively from 2 to 4000 kDa, alternatively from 5 to 3000 kDa, alternatively from 10 to 2000 kDa, alternatively from 10 to 1000 kDa, alternatively from 15 to 500 kDa, alternatively from 20 to 100 kDa, alternatively from 25 to 70 kDa.

The cationic polymer may be selected from the group consisting of linear polyethyleneimine (linear PEI), branched polyethyleneimine (branched PEI), polyallylamine hydrochloride (PAH), polydiallyldimethylammonium chloride (PDADMAC), copolymers thereof and mixtures thereof.

The cationic polymer may be selected from the group consisting of:
a) Linear polyethyleneimine of the formula:

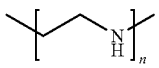

in which n is an integer representing the degree of polymerization, wherein n ranges from 50 to 20,000, alternatively from 100 to 3,500;
b) Branched polyethyleneimine consisting of primary, secondary and tertiary amine groups of the formula:

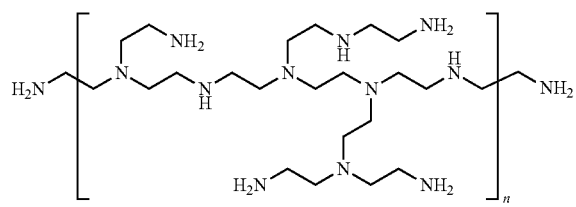

in which n is an integer representing the degree of polymerization, wherein n ranges from 10 to 4,000, alternatively from 50 to 1,000;
c) Polyallylamine hydrochloride (PAH) of the formula:

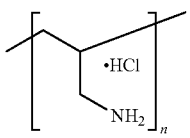

in which n is an integer representing the degree of polymerization, wherein n ranges from 50 to 20,000, alternatively from 150 to 800;
d) Polydiallyldimethylammonium chloride (PDADMAC) of the formula:

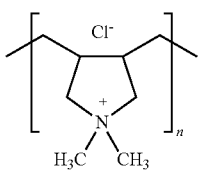

in which n is an integer representing the degree of polymerization, wherein n ranges from 50 to 20,000, alternatively from 150 to 4,000; and
e) copolymers thereof and mixtures thereof.

The cationic polymer may comprise one or more compounds selected from the group consisting of cosmetically active molecules, care ingredients, optically active molecules, pharmaceutical active molecules, biomarkers and mixtures thereof.

Anionic Polymer

The anionic polymer which is comprised in the second composition may be selected from the group consisting of coloured anionic polymers, anionic uncoloured polymers and mixtures thereof.

The anionic polymer may be a homopolymer or a heteropolymer.

The anionic polymer according to the present invention may comprise cationic and anionic monomeric units as long as the overall charge at full protonation is negative. As such, the following applies: $C_1 > C_2$, with $C_1$ being the total number of anionic charges and $C_2$ being the total number of cationic charges within one anionic polymer at full deprotonation.

The anionic polymer may have a charge density at full deprotonation of at least 0.3, alternatively at least 0.6, alternatively at least 0.8, alternatively at least 1.0 negative charges per monomer unit.

The anionic polymer may have a weight average molecular weight of at least 1 kDa, alternatively from 10 kDa to 1000 kDa, alternatively from 20 to 800 kDa, alternatively from 30 to 500 kDa, alternatively from 70 to 200 kDa.

The anionic polymer may be selected from the group consisting of a biopolymers, synthetic polymers, and mixtures thereof.

Synthetic polymers may be selected from the group consisting of polystyrene sulfonate salts, polyacrylic acid, poly(methacrylic acid) salts, carboxymethylcellulose salts, PVA (Polyvinylalcohol), Polyvinylpyrrolidon-co-vinylimidazol, PSS-co-maleic acid, and mixtures thereof.

Biopolymers may be selected from the group consisting of polysaccharides, carrageenans, and mixtures thereof.

Polysaccharides may be selected from the group consisting of Dextrans, and mixtures thereof. Most preferred polysaccharides are Dextrans, more preferably Dextran sulfate salts.

Carrageenans may be selected from the group consisting of κ-, ι- and λ-Carrageens. Most preferred Carrageenans are λ-Carrageens.

The anionic polymer may comprise at least one monomer unit comprising at least one functional group selected from the group consisting of sulfate, sulfonate, carboxylate, phosphate, phosphonate groups and mixtures thereof. Alternatively, the functional group may be selected from the group consisting of sulfate, sulfonate, carboxylate groups and mixtures thereof.

The anionic polymers may be selected from the group consisting of:
a) Polystyrene sulfonate (PSS) sodium salt of the formula:

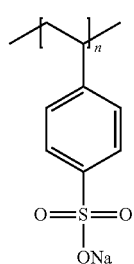

in which n is an integer representing the degree of polymerization, wherein n ranges from 50 to 20,000, alternatively from 150 to 500;
b) Co-polymer of polystyrene sulfonate (PSS) sodium salt and poly(4-styrenesulfonic acid-co-maleic acid) of the formula:

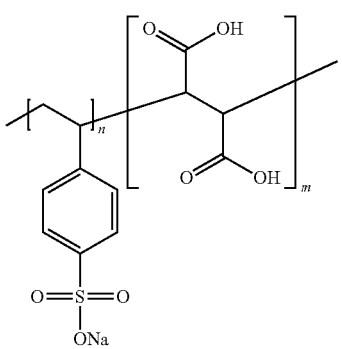

in which n and m are integers representing the degree of polymerization, wherein n+m ranges from 50 to 20,000, alternatively from 150 to 500;
c) λ-Carrageenan;
d) Dextran sulfate sodium salt;
e) Polyacrylic acid (PAA) of the formula:

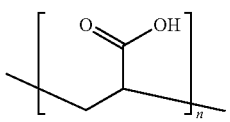

in which n is an integer representing the degree of polymerization, wherein n ranges from 50 to 20,000, alternatively from 150 to 1,000;
f) Alginic acid sodium salt;
g) Carboxymethylcellulose sodium salt of the formula:

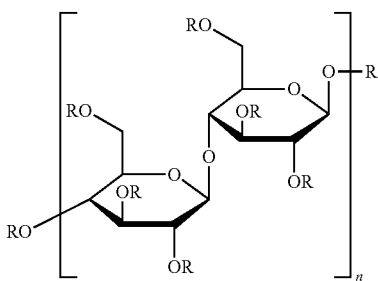

in which R is H or $(CH_2)_2COONa$ and n is an integer representing the degree of polymerization; copolymers thereof and mixtures thereof.

The anionic polymers may comprise one or more compounds selected from the group consisting of cosmetically active molecules, care ingredients, optically active molecules, pharmaceutical active molecules, biomarkers and mixtures thereof.

Coloured Cationic Polymers and Coloured Anionic Polymers

The coloured cationic polymers and the coloured anionic polymers comprise at least one chromophore and/or at least one fluorophore. Any of the hereinbefore exemplified cationic polymers or anionic polymers can comprise at least one chromophore and/or at least one fluorophore either in the skeleton or as pendent group of the polymeric backbone.

The chromophores may be selected from the group consisting of radicals derived from nitrobenzene, azo, imine, hydrazine, phenothiazine, xanthene, phenanthridine, phthalocyanin and triarylmethane-based dyes, and those obtained from direct dyes containing a carbonyl group and mixtures thereof. The chromophores may be selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

The chromophores may be substituted with at least one amine, hydroxyl, sulfate, sulfonate, carboxylate, phosphate, phosphonate, or halide group. These chromophores may be selected from the group consisting of radicals derived from acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of radicals derived from di-, tetra- or hexa-sulfonated triazine-stilbenes, coumarins, imidazolines, diazoles, triazoles, benzoxazolines, biphenyl-stilbenes optical brighteners, and mixtures thereof.

The coloured cationic polymer and/or the coloured anionic polymer may comprise the same type of chromophore and/or fluorophore or different types of chromophores and/or fluorophores.

The chromophores and/or fluorophores of the coloured cationic polymers and/or the coloured anionic polymers may be anionic, cationic, non-ionic, amphoteric or any combination thereof.

For instance, the coloured cationic polymers and/or the coloured anionic polymers may comprise at least one first chromophore that is anionic, cationic, non-ionic or amphoteric, and at least one second chromophore that is anionic, cationic, non-ionic or amphoteric.

Alternatively, the coloured cationic polymers and/or the coloured anionic polymers may comprise at least one first fluorophore that is anionic, cationic, non-ionic or amphoteric, and at least one second fluorophore that is anionic, cationic, non-ionic or amphoteric. Alternatively, the coloured cationic polymers and/or the coloured anionic polymers may comprise at least one chromophore that is anionic, cationic, non-ionic or amphoteric, and at least one fluorophore that is anionic, cationic, non-ionic or amphoteric.

In preferred embodiments, the coloured cationic polymers and/or the coloured anionic polymers comprise at least one first chromophore that is anionic and at least one second chromophore that is anionic. Alternatively, the coloured cationic polymers and/or the coloured anionic polymers comprise at least one first chromophore that is anionic and at least one second chromophore that is cationic. Alternatively, the coloured cationic polymers and/or the coloured anionic polymers comprise at least one first chromophore that is anionic and at least one second chromophore that is non-ionic. Alternatively, the coloured cationic polymers and/or the coloured anionic polymers comprise at least one first chromophore that is anionic and at least one second chromophore that is amphoteric.

Alternatively, the coloured cationic polymers and/or the coloured anionic polymers comprise at least one first chromophore that is cationic and at least one second chromophore that is cationic. Alternatively, the coloured cationic polymers and/or the coloured anionic polymers comprise at least one first chromophore that is cationic and at least one second chromophore that is non-ionic. Alternatively, the coloured cationic polymers and/or the coloured anionic polymers comprise at least one first chromophore that is cationic and at least one second chromophore that is amphoteric.

Alternatively, the coloured cationic polymers and/or the coloured anionic polymers comprise at least one first chromophore that is non-ionic and at least one second chromophore that is non-ionic. Alternatively, the coloured cationic polymers and/or the coloured anionic polymers comprise at least one first chromophore that is non-ionic and at least one second chromophore that is amphoteric.

Alternatively, the coloured cationic polymers and/or the coloured anionic polymers comprise at least one first chromophore that is amphoteric and at least one second chromophore that is amphoteric.

In further preferred embodiments, the coloured cationic polymers and/or the coloured anionic polymers comprise at least one first fluorophore that is anionic and at least one second fluorophore that is anionic. Alternatively, the coloured cationic polymers and/or the coloured anionic polymers comprise at least one first fluorophore that is anionic and at least one second fluorophore that is cationic. Alternatively, the coloured cationic polymers and/or the coloured anionic polymers comprise at least one first fluorophore that is anionic and at least one second fluorophore that is non-ionic. Alternatively, the coloured cationic polymers and/or the coloured anionic polymers comprise at least one first fluorophore that is anionic and at least one second fluorophore that is amphoteric.

Alternatively, the coloured cationic polymers and/or the coloured anionic polymers comprise at least one first fluorophore that is cationic and at least one second fluorophore that is cationic. Alternatively, the coloured cationic polymers and/or the coloured anionic polymers comprise at least one first fluorophore that is cationic and at least one second fluorophore that is non-ionic. Alternatively, the coloured cationic polymers and/or the coloured anionic polymers comprise at least one first fluorophore that is cationic and at least one second fluorophore that is amphoteric.

Alternatively, the coloured cationic polymers and/or the coloured anionic polymers comprise at least one first fluorophore that is non-ionic and at least one second fluorophore that is non-ionic. Alternatively, the coloured cationic polymers and/or the coloured anionic polymers comprise at least one first fluorophore that is non-ionic and at least one second fluorophore that is amphoteric. A Alternatively, the coloured cationic polymers and/or the coloured anionic polymers comprise at least one first fluorophore that is amphoteric and at least one second fluorophore that is amphoteric.

In further preferred embodiments, the coloured cationic polymers and/or the coloured anionic polymers comprise at least one chromophore that is anionic and at least one fluorophore that is anionic. Alternatively, the coloured cationic polymers and/or the coloured anionic polymers comprise at least one chromophore that is anionic and at least one fluorophore that is cationic. Alternatively, the coloured cationic polymers and/or the coloured anionic polymers comprise at least one chromophore that is anionic and at least one fluorophore that is non-ionic. Alternatively, the coloured cationic polymers and/or the coloured anionic polymers comprise at least one chromophore that is anionic and at least one fluorophore that is amphoteric.

Alternatively, the coloured cationic polymers and/or the coloured anionic polymers comprise at least one chromophore that is cationic and at least one fluorophore that is anionic. Alternatively, the coloured cationic polymers and/or the coloured anionic polymers comprise at least one chromophore that is cationic and at least one fluorophore that is cationic. Alternatively, the coloured cationic polymers and/or the coloured anionic polymers comprise at least one chromophore that is cationic and at least one fluorophore that is non-ionic. Alternatively, the coloured cationic polymers and/or the coloured anionic polymers comprise at least one chromophore that is cationic and at least one fluorophore that is amphoteric.

Alternatively, the coloured cationic polymers and/or the coloured anionic polymers comprise at least one chromophore that is non-ionic and at least one fluorophore that is anionic. Alternatively, the coloured cationic polymers and/or the coloured anionic polymers comprise at least one chromophore that is non-ionic and at least one fluorophore that is cationic. Alternatively, the coloured cationic polymers and/or the coloured anionic polymers comprise at least one chromophore that is non-ionic and at least one fluorophore that is non-ionic. Alternatively, the coloured cationic polymers and/or the coloured anionic polymers comprise at least one chromophore that is non-ionic and at least one fluorophore that is amphoteric.

Alternatively, the coloured cationic polymers and/or the coloured anionic polymers comprise at least one chromophore that is amphoteric and at least one fluorophore that is anionic. Alternatively, the coloured cationic polymers and/or the coloured anionic polymers comprise at least one chromophore that is amphoteric and at least one fluorophore that is cationic. Alternatively, the coloured cationic polymers and/or the coloured anionic polymers comprise at least one chromophore that is amphoteric and at least one fluorophore that is non-ionic. Alternatively, the coloured cationic polymers and/or the coloured anionic polymers comprise at least one chromophore that is amphoteric and at least one fluorophore that is amphoteric.

Having a coloured cationic polymer and/or a coloured anionic polymer with different types of chromophores and/or fluorophores may help to cover a broad range of colour shades which can be obtained on hair which are coloured according to the method of the present wherein the first composition or the second composition comprises such a coloured cationic polymer or such a coloured anionic polymer. Specifically, choosing specific combinations of different chromophores and/or fluorophores enables the provision of various colours, shades and intensities of colour optimally tailored for the user.

The coloured cationic polymers may be selected from the group consisting of:
1. Coloured linear or branched polyethyleneimine (PEI) of the formula:

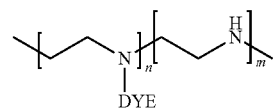

in which n and m are integers representing the degree of polymerization, wherein m/n ranges from 0 to 1,000 provided that n is different from 0 and/or m+n ranges from 50 to 20,000, alternatively from 100 to 3,500;

2. Coloured polyallylamine hydrochloride of the formula:

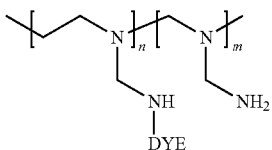

in which n and m are integers representing the degree of polymerization, wherein m/n ranges from 0 to 1,000 provided that n is different from 0 and/or m+n ranges from 50 to 20,000, alternatively from 150 to 800;

3. Coloured polydiallyldimethylammonium chloride of the formula:

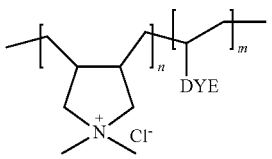

in which n and m are integers representing the degree of polymerization, wherein m/n ranges from 0 to 1,000 provided that n is different from 0 and/or m+n ranges from 50 to 20,000, alternatively from 100 to 3,500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The coloured cationic polymers may be selected from linear polyethyleneimine (PEI)—Rhodamine B of the formula:

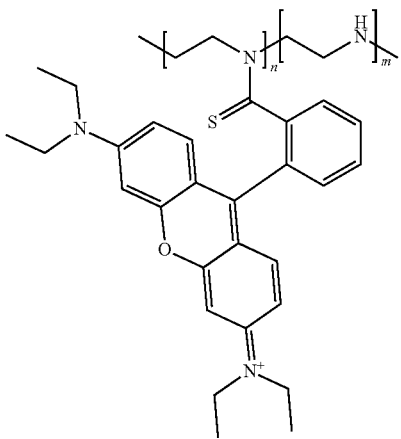

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The coloured anionic polymers may be selected from coloured anionic polymers with the following formula:

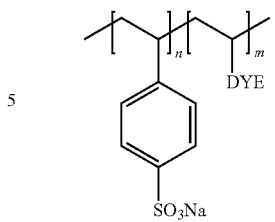

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

Labelling Degree

The labelling degree k is a measure for the loading of a polymer with a dye. The labelling degree k is defined as n:m, with n being the number of chromophores and/or fluorophores per polymer and m being the monomeric units per polymer. As such, the higher the labelling, the higher the labelling degree, i.e. the more chromophores and/or fluorophores are present in one coloured cationic polymer. The labelling degree k may be between 1:2 to 1:100, alternatively between 1:5 to 1:90. alternatively between 1:10 to 1:80, alternatively between 1:15 to 1:70, alternatively between 1:20 to 1:60, alternatively between 1:30 to 1:50, alternatively between 1:35 to 1:45. Alternatively, the labelling degree k may be between 1:1100 to 1:1:1000,000, alternatively between 1:2000 to 1:900,000, alternatively between 1:5000 to 1:800,000, alternatively between 1:10,000 to 1:700,000, alternatively between 1:50,000 to 1:600,000, alternatively between 1:100,000 to 1:500,000, alternatively between 1:150,000 to 1:400,000, alternatively between 1:200,000 to 1:300,000.

The choice of the appropriate labelling degree primarily depends on the types of chromophores and/or fluorophores used for labelling the cationic and/or anionic polymer. For instance, when using chromophores and/or fluorophores providing per se a stronger colour intensity to hair, the labelling degree can be lower, e.g., between 1:100,000 to 1:1,000,000. On the other hand, when using chromophores and/or fluorophores providing per se a weaker colour intensity to hair, the labelling degree should be higher, e.g., between 1:2 to 1:1000.

The labelling degree may also depend on the type of polymer backbone, and more particularly on the number of possible binding positions on the polymer backbone onto which the dye can be covalently bonded. Notably, these binding positions can be activated or deactivated. For instance, deactivation can be carried out by e.g., chemically bonding specific protection groups to at least some of the binding positions. Accordingly, activation can be carried out e.g., by splitting such protection groups from the respective binding position. As such, the polymer backbone can be tailored to have the desired number of binding positions for the dye. Various other parameters help adjusting the appropriate labelling degree.

Compositions

The system of the present invention may comprise a first composition and a second composition as described herewith. The system may further comprise a third, a fourth, a fifth, a sixth, a seventh, an eighth, a ninth and/or a tenth composition. Each of these compositions may be first or second compositions as defined herein.

For instance, the system of the present invention may comprise:
- a first composition comprising at least one coloured cationic polymer as defined herein with a labelling degree as defined herein,
- a second composition comprising at least one coloured or uncoloured anionic polymer as defined herein,
- a third composition comprising at least one coloured or uncoloured cationic polymer as defined herein with a labelling degree as defined herein, and
- a fourth composition comprising at least one coloured or uncoloured anionic polymer as defined herein. As such, the coloured cationic polymers of the first and third compositions may be the same or different. Similarly, the anionic polymers of the second and fourth compositions may be the same or different. As such, the third and fourth compositions may have the same or different solvents, polymer concentrations, pH values, salt concentrations, and further ingredients as the respective first and second compositions.

Solvents

The first and/or the second compositions which are used to carry out the method according the present invention may further comprise a solvent. The solvent may be selected from water, or a mixture of water and at least one organic solvent to dissolve the compounds that would not typically be sufficiently soluble in water. The first and/or the second compositions may be aqueous compositions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the first and/or the second compositions may comprise water as a main ingredient, particularly in a total amount ranging from at least 50%, alternatively from at least 60%, alternatively from at least 70%, by total weight of the composition. Typically, when present, the first and/or the second compositions comprises a total amount of organic solvents ranging from about 1% to about 30%, by total weight of the composition.

Concentrations

The first composition may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

The second composition may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

In preferred embodiments, the first composition may comprise a total concentration of cationic polymers which is lower than the total concentration of anionic polymers in the second composition. Alternatively, the first composition may comprise a total concentration of cationic polymers which is higher than the total concentration of anionic polymers in the second composition. Alternatively, the first composition may comprise a total concentration of cationic polymers which is equal to the total concentration of anionic polymers in the second composition.

By using different polymer concentrations in the first and second compositions, different effects can be achieved. For instance, using higher polymer concentrations in the first composition than in the second composition can result in portions of hair with bilayer structure (i.e. a structure where a coloured cationic polymer layer attached to the hair surface is covered by an anionic polymer layer) and portions of hair where no such bilayer structure is formed. By repeating applying the first composition followed by the second composition (i.e. carrying out a second treatment), only in those portions where a bilayer has formed, a second coloured cationic polymer layer can be attached to the anionic polymer layer of the bilayer structure resulting in an increase of colour intensity. On the other hand, in those portions where no bilayer has formed (i.e., where only a cationic polymer layer has been attached to the hair surface without an anionic protective layer), no second coloured cationic polymer layer can be attached, and as such, no change in colour intensity occurs. This leads to different colour intensities on different hair portions of the user which may be intentional in order to spotlight certain portions of hair. Notably, those portions of hair where no such additional second coloured cationic polymer layer could be attached due to a lack of bilayer structure will now be covered by an anionic polymer layer from the second treatment, thus forming a "delayed" bilayer structure. On this "delayed" bilayer structure, a second coloured cationic polymer layer can now be attached by repeating applying the first composition followed by the second composition once again (i.e. carrying out a third treatment). On the other hand, those portions where an additional second coloured cationic polymer layer has already been attached by the second treatment, the third treatment enables the attachment of a third coloured cationic polymer layer depending on whether or not a second anionic polymer layer covers said second coloured cationic polymer layer. To ensure the attachment of a second anionic polymer layer to the second coloured cationic polymer layer in the second treatment, the total concentration of anionic polymers in the second composition now should be higher than the total concentration of coloured cationic polymers in order to compensate the lack of anionic polymers on those portions of hair where no such bilayer structure has formed. Thus, after the third treatment, there may be portions of hair having two full bilayer structures while there may also be portions of hair having three full bilayer structures, thereby providing different colour intensities in different hair portions. After having adjusted the desired colour intensity interval between at least two portions of hair, a fourth treatment can be carried out by repeating the step of applying the first composition followed by the second composition wherein the polymer concentrations in the first and second compositions are substantially the same.

Therefore, through variation of the total polymer concentrations in the first and second compositions, different colour intensities on different hair portions can be tailored which may be desired in various cases, e.g., where hair greying takes place only in certain areas of hair such as temples etc.

pH Value

The first and/or second composition may have a pH ranging from 2 to 14, alternatively from 3 to 11, alternatively from 5 to 10, alternatively from 7 to 9.

For instance, the first composition may have a pH ranging from 6 to 11, alternatively from 7 to 11, alternatively from 7 to 10.5, alternatively from 7.5 to 10.5, more alternatively from 7.5 to 10, even more alternatively from 8 to 10.

The second composition may have a pH ranging from 3 to 10, alternatively from 4 to 9, more alternatively from 4 to 9, even more alternatively from 4 to 8.

In preferred embodiments, the first composition may have a pH that is lower than the pH of the second composition. Alternatively, the first composition may have a pH that is higher than the pH of the second composition. Alternatively, the first composition may have a pH that is equal to the pH of the second composition. In further embodiments, the first composition may have a pH different to the pH of the third composition, wherein the pH of the first composition can be higher or lower than the pH of the third composition.

Adjusting the pH values in the first and second compositions is desirable for various reasons. For instance, too extreme pH values, e.g., pH>12 or pH<3 may cause damage to the structure of the hair and may be irritating for the scalp of the user, especially when such a process is repeated more than once. On the other hand, the lower the pH of the first composition, the better the protonation of the coloured cationic polymer. This leads to a higher cationic charge which is desirable for a better attachment to the anionic hair surface. Similarly, the higher the pH of the second composition, the better the deprotonation of the anionic polymer. This leads to a higher anionic charge which is desirable for a better attachment to the coloured cationic polymer. Therefore, in principle, the first composition may have a pH that is lower than the pH of the second composition.

However, the present inventors unexpectedly found out that the colour intensity increases proportionally to the pH of the first composition. Thus, in most preferred embodiments, the first composition may have a pH that is higher than the pH of the second composition. In certain instances, while it is preferred to use a weak acidic pH in the second composition, such as a pH between 5 and 6, the pH in the first composition may be between 6 to 10, more preferably between 7 to 9.

Nevertheless, one of the advantages of the system according to the present invention is that the hair may be coloured with a good colour intensity even if both compositions which are used have a lower pH. Taking further into account the skin's natural pH levels being in the weakly acid, depending e.g. on the gender and age of the user, the pH levels of the first and second compositions can particularly be tailored for the user's need.

Salt

The first and/or the second composition may comprise a cosmetically acceptable salt at a concentration ranging from 0 to 1.5 mol/L, alternatively from 0.05 to 1 mol/L, alternatively from 0.2 to 0.5 mol/L. The first and/or the second composition may comprise the same cosmetically acceptable salt(s) or different cosmetically acceptable salt(s).

The first composition may comprise at least one cosmetically acceptable salt at a concentration ranging from 0 to 1.5 mol/L, preferably from 0.05 to 1 mol/L, more preferably from 0.2 to 0.5 mol/L.

The second compositions may comprise at least one cosmetically acceptable salt at a concentration ranging from 0 to 1.5 mol/L, preferably from 0.05 to 1 mol/L, more preferably from 0.2 to 0.5 mol/L.

In preferred embodiments, the first composition may comprise a cosmetically acceptable salt at a concentration that is higher than the concentration of the cosmetically acceptable salt in the second composition. Alternatively, the first composition may comprise a cosmetically acceptable salt at a concentration that is lower than the concentration of the cosmetically acceptable salt in the second composition. Alternatively, the first composition may comprise a cosmetically acceptable salt at a concentration that is equal to the concentration of the cosmetically acceptable salt in the second composition.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Adjusting the concentration of the cosmetically acceptable salt in the first composition is another important parameter. For instance, using higher concentrations of cosmetically acceptable salts in the first composition comprising the coloured cationic polymer (e.g. up to 1 mol/L) has the effect that a greater number of negatively charged ions can gather around each cationic polymer chain. This leads to the formation of a strong electrostatic shield around each polymer chain. The resulting decrease of positive charge in the immediate surroundings of each polymer chain has the effect that only those parts of the polymer chain which have still enough positive charge will ionically bind to the negatively charged hair surface. The number decrease of anchoring sites of each polymer chain results in an undulated orientation of each coloured cationic polymer, e.g., on the hair surface, thereby enabling the binding of a greater number of coloured cationic polymers. The greater the number of bound coloured cationic polymers on a defined hair surface portion, the more intensive the colour of this portion. Thus, adjusting the salt concentration, particularly in the first composition, may be particularly useful to modify the colour intensity.

Applicators

The first and/or the second compositions may be applied to the hair using an applicator such as a brush or a sponge. Alternatively, the first and/or the second compositions may be applied to the hair by spraying or foaming the first and/or the second compositions to the hair or by dipping the hair into the first and/or the second composition. Alternatively, the first and/or the second compositions may be applied to the hair using printing technology.

Method

Embodiments also relate to a method for colouring hair comprising applying the two different compositions, i.e. the first and second compositions, successively to the hair. The method for colouring hair may comprise the step a) of carrying out the following sequence of steps:
  (i) applying the first composition as described herein to a first portion of the hair;
  (ii) applying the second composition as described herein to a second portion of the hair, and
  (iii) optionally the third composition as described herein to a third portion of the hair,
  wherein the first, the second and the third portions have at least one common area.

The second composition is applied after the first composition to the hair. The optional third composition is applied after the second composition to the hair.

Having at least one common area between the first portion of the hair to which the first composition is applied and the second portion of the hair to which the second composition is applied ensures that at least a portion of the second composition is applied to the same portion of the hair as at least a portion of the first composition.

The method may further comprise the optional step b) of repeating step a), without item (iii), at least once, wherein the common area of each of the repeated steps a) has at least one common area with the common area of step a) and the common area of each of the other repeated steps a), in case step a) is repeated more than once. This ensures that at least a portion of each of the first and second compositions which are applied to the hair in each of the sequences of steps is applied to the same portion of the hair.

Each of the first compositions of step a) and of the repeated steps a) may be the same or different. Each of the second compositions of step a) and of the repeated steps a) may be the same or different.

In step a) and/or in at least one of the repeated steps a), the cationic polymer is a coloured cationic polymer.

In step a) and/or in each of the repeated steps a), the cationic polymer may be a coloured cationic polymer.

In step a) and/or in each of the repeated step a), the first and the second compositions may be applied all over the hair.

In step b), step a) may be repeated at least at least twice, alternatively at least three times. Alternatively, in step b), step a) may be repeated from 1 to 3 times.

In the embodiments wherein in step b) of the method, step a) is repeated once, the first composition of step a) may comprise at least one coloured cationic polymer and the first composition of the repeated a) may comprise at least one cationic uncoloured polymer.

The method may further comprise step c) of applying after step a) a third composition comprising at least one cationic polymer to a third portion of the hair wherein the third portion of the hair has at least one common area with the common area of step a).

Alternatively, the method may further comprise the step d) of applying after step b) a third composition comprising at least one cationic polymer to a third portion of the hair, wherein the third portion of the hair has at least one common area with the common area of step b).

In the steps c) and/or d), the third composition may be applied all over the hair. The cationic polymer comprised in the third composition may be a coloured cationic polymer or a cationic uncoloured polymer.

Steps i) and/or ii) of the sequence of steps of the method may further comprise the subsequent sub-step of removing the excess of respectively the first composition and/or the second composition from the hair.

Steps i) and/or ii) of the sequence of steps of the method may further comprise the subsequent sub-step of applying energy to the hair in the form of heat, ultrasounds, infrared and/or microwaves. This sub-step may be carried out either after the application of the first or second composition to the hair or after removing the excess of the first composition or the second composition from the hair. While not wishing to be bound by theory, it is believed that applying energy to the hair may accelerate the speed of formation of the polymeric layers on the hair and therefore may increase the stability of the layers once they are formed on the hair. The hair may be heated to a temperature ranging from 5° C. to 70° C., alternatively 20° C. to 60° C., alternatively 40° C. to 60° C.

Steps i) and/or ii) of the sequence of steps of the method may further comprise the subsequent sub-step of washing and/or rinsing the hair. The hair may be washed and/or rinsed with a liquid selected from the group consisting of a cosmetically acceptable solvent, a solution comprising a cosmetically acceptable solvent and a cosmetically acceptable salt, a shampoo composition and mixtures thereof. Alternatively, the hair may be washed and/or rinsed with water.

After carrying out the method according to the present invention, a conditioning agent may be applied to the hair. Any of the conditioning agents disclosed hereinafter may be applied to the hair.

The hair may be pretreated prior to step i) of the first sequence of steps to modify the number of positive or negative charges in some portions of the hair or all over the hair. This pretreatment may be done using chemical or physical means such as pH change, oxidation, reduction, bleaching, plasma treatment, ozone treatment, electrowetting, dry or wet ion-treatment.

Depending on the charge of the hair, the cationic and/or the anionic polymers may attach more or less easily to the hair and therefore a different colour result may be obtained on different portions of the hair which are differently charged. This pretreatment may therefore help to tailor the colour result which is obtained on different portions of the hair, e.g. to obtain a different colour result on hair roots vs. hair tips.

Use

The present invention also relates to the use of the hair colouring system for providing a multilayer structure on an area of hair. The multilayer structure may comprise at least two polymeric layers which are placed on top of each other by alternating the deposition of the cationic polymers and the anionic polymers as described herein. The present invention further relates to the use of the hair colouring system for controlling the colour intensity of hair. Controlling the colour intensity of hair may be particularly achieved by at least one of adjusting the labelling degree of the coloured cationic polymer, adjusting the pH value of the first and/or second compositions, adjusting the polymer concentrations in the first and/or second compositions, adjusting the salt concentration in the first and/or second compositions, adjusting the ionic strength in the first and/or second compositions, adding specific additives, such as additives selected from the group consisting of alkalizing agents, pH modifiers and/or buffering agents, thickeners and/or rheology modifiers, (anionic, cationic, nonionic, amphoteric or zwitterionic) surfactants, and any combination thereof.

Hair Colouration

The present invention also relates to a hair colouration which is obtainable by the method according to the present invention. As already explained hereinbefore, the structure of the hair colouration is unique in that it is made of alternating polymeric layers which are formed by the alternate deposition of coloured cationic polymers and anionic polymers.

Hair Colouring Kit

The present invention also relates to a hair colouring kit comprising a first compartment comprising the first composition as defined hereinbefore and a second compartment comprising the second composition as defined hereinbefore.

Other Ingredients

The first and/or the second compositions according to the present invention may comprise, in addition to the ingredients indicated above, further ingredients in order to further enhance the properties of the composition, as long as these are not excluded by the claims.

Suitable further ingredients include, but are not limited to: oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Particularly preferred further ingredients comprise alkalizing agents, pH modifiers and/or buffering agents, thickeners and/or rheology modifiers, (anionic, cationic, nonionic, amphoteric or zwitterionic) surfactants, and any combination thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Oxidizing Agents

Any of the first to fourth compositions according to the present invention may further comprise one or more oxidizing agent(s). The oxidizing agent(s) may preferably be selected from the group consisting of hypochlorous acid, peracetic acid, persulfate, chlorine dioxide, perboric acid, salts thereof, ozone, hydrogen peroxide and mixtures thereof. The oxidizing agent(s) may more preferably be selected from the group consisting of hypochlorous acid, salts thereof and mixtures thereof. The oxidizing agent(s) may even more preferably be selected from the group consisting of sodium hypochlorite, calcium hypochlorite, potassium hypochlorite and mixtures thereof.

Any of the first to fourth compositions may comprise a total amount of oxidizing agents selected from the group consisting of sodium hypochlorite, calcium hypochlorite, potassium hypochlorite and mixtures thereof of up to 25% by total weight of the respective first to fourth compositions. Any of the first to fourth compositions may comprise a total amount of oxidizing agents selected from the group consisting of sodium hypochlorite, calcium hypochlorite, potassium hypochlorite and mixtures thereof ranging from 0.01% to 10%, preferably from 0.2% to 2%, more preferably from 0.5% to 1.5% by total weight of the respective first to fourth compositions. The amount of each particular oxidizing agent or mixtures thereof described hereinbefore can account for up to 100% (or 100%) of the total amount of oxidizing agents in the any of the first to fourth compositions.

The first or second compositions may be a shampoo composition, a hair conditioning composition or a hair treatment composition.

Any of the first to fourth compositions of the present invention may comprise at least one oxidizing agent and/or at least one source of an oxidizing agent. The oxidizing agents may be provided in aqueous solution or as a powder which is dissolved prior to use. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 litre of deionized water at 25° C. Suitable water-soluble oxidizing agents include, but are not limited to: inorganic peroxygen materials capable of yielding hydrogen peroxide in an aqueous solution.

The oxidizing agents are valuable for the initial solubilisation and decolourisation of the melanin (bleaching) as well as for the activation of the hair surface such that through oxidization of proteins located at the hair surface, the overall negative charge is increased. An increased overall negative charge of the hair surface is desirable for a better attachment of the cationic polymer comprised in the hair colouring system applied to the hair in the subsequent step c) of the method of the present invention.

According to an embodiment, any of the first to fourth compositions may comprise a total amount of oxidizing agents ranging from 0.1% to 15%, alternatively from 0.2% to 15%, alternatively from 0.3% to 15%, alternatively ranging from 0.1% to 12%, alternatively from 0.2% to 12%, alternatively from 0.3% to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the respective first to fourth compositions. Alternatively, any of the first to fourth compositions may comprise a total amount of oxidizing agents of less than 3%, alternatively less than 2%, alternatively less than 1%, alternatively less than 0.5%, alternatively less than 0.3% alternatively less than 0.1% by total weight of the respective first to fourth compositions. The lower limit for the oxidizing agents may be at least 0.01% by total weight of the respective first to fourth compositions. Any of the first to fourth compositions having a low amount of oxidizing agents is less damaging the hair than standard hair colouring composition which usually comprise a high concentration of oxidizing agent.

Any of the first to fourth compositions may also be substantially free of oxidizing agents, i.e. having oxidizing agents less than 0.1%, and more particularly less than 0.01% by total weight of the respective first to fourth compositions. For example, a first and/or the second compositions having surfactants such as amphoteric surfactants may be substantially free of oxidizing agents. A first and/or the second compositions which comprises oxidizing agents, however, may also include surfactants such as at least one of anionic surfactants, cationic surfactants, amphoteric surfactants, non-ionic surfactants, and combination thereof.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired.

Any of the first to fourth compositions may comprise a water-soluble oxidizing agent selected from the group consisting of peroxides, percarbonates (which may be used to provide a source of both oxidizing agent and carbonate ions and or ammonium ions), persulphates, and mixtures thereof. The particularly preferred oxidizing agent is hydrogen peroxide.

When any of the first to fourth compositions of the present invention is obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the H2O2 relative to the total weight of the developer composition. A preferred example of a developer composition with respectively about 6% and about 9% H2O2, comprises as INCI ingredients: Water, H2O2, Cetearyl Alcohol, Ceteareth-25, Salicylic Acid, Phosphoric Acid, Disodium Phosphate, Etidronic Acid. Another preferred example a developer composition comprises as INCI ingredients: Water, H2O2, cetearyl alcohol, lanolin alcohol, sodium lauryl sulfate, parfum, salicylic acid, phosphoric acid, disodium phosphate, linalool, hexyl cinnamal, etidronic acid, tocopherol. Another preferred example a developer composition comprises as INCI ingredients: Water, H2O2, cetearyl alchohol, lanolin alcohol, sodium lauryl sulfate, parfum, salicylic acid, phosphoric acid, disodium phosphate, linalool, hexyl cinnamal, etidronic acid, tocopherol.

Reducing Agents

Any of the first to fourth compositions of the present invention may comprise at least one reducing agent and/or at least one source of a reducing agent. The reducing agents may be provided in aqueous solution or as a powder which is dissolved prior to use. any of the first to fourth compositions may comprise a total amount of reducing agents ranging from 0.1% to 15%, alternatively from 0.2% to 15%, alternatively from 0.3% to 15%, alternatively from 0.1% to 12%, alternatively from 0.2% to 12%, alternatively from 0.3% to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the respective composition.

The reducing agent(s) may preferably be selected from the group consisting inorganic reducing agent(s) and organic reducing agent(s), and combinations thereof.

Inorganic Reducing Agents:

sulfide, disulfite, thiosulfate, sulfite, phosphonic acid, hydrazine, borohydride, aluminiumhydride, hydrogen, sodium sulfite, sodium bisulfate, sodium hydrogensulfite, sodiumthiosulfate, and combinations thereof.

Organic Reducing Agents:

formic acid, ketoglutarate, DTT red, NADH/H+, dihydrolipoic acid, cysteine, vitamin C, vitamin E, Dithiothreitol (DTT), mercaptanes, thioglycolic acid, ammonium thioglycolate, sodium thioglycolate cysteine, ascorbic acid, glyceryl monothiopropionate, ammonium thiolactate, dithioerythritol, glutathione, 1,3-dithiopropanol, thioglycolamide, glyceryl monothioglycolate, glyceryl thiolactate, and combinations thereof.

Any of the first to fourth compositions may include either reducing agent(s) or oxidizing agent(s).

Alternatively, any of the first to fourth compositions may also be substantially free of reducing agents, i.e. having reducing agents less than 0.1%, and more particularly less than 0.01% by total weight of the respective composition. For example, any of the first to fourth compositions having surfactants such as amphoteric surfactants may be substantially free of reducing agents. A first to fourth compositions which comprises reducing agents, however, may also include surfactants such as at least one of anionic surfactants, cationic surfactants, amphoteric surfactants, non-ionic surfactants, and combination thereof.

Preferred reducing agents are thioglycolic acid, mercaptanes, ammonium thioglycolate, sodium thioglycolate cysteine, sodium sulfite, ascorbic acid, glyceryl monothiopropionate, ammonium thiolactate, dithiothreitol, dithioerythritol, glutathione, dihydrolipoic acid, 1,3-dithiopropanol, thioglycolamide, glyceryl monothioglycolate, sodium bisulfite, sodium hydrogensulfite, sodiumthiosulfate, glyceryl thiolactate, and combinations thereof.

Alkalizing Agents

Alkalizing agents are particularly useful to adjust the pH value in the first and second compositions which—as described in detail uner the headline "pH Value"—is inter alia an important parameter for controlling the colour intensity of hair.

Any of the first to fourth compositions according to the present invention may further comprise at least one alkalizing agent. Any alkalizing agent known in the art may be used.

Typically, any of the first to fourth compositions may comprise a total amount of alkalizing agents ranging from 0.1% to 10%, alternatively from 0.5% to 6%, alternatively from 1% to 4%, by total weight of the respective composition.

Alternatively, the any of the first to fourth compositions may comprise a total amount of alkalizing agents of less than 1%, alternatively less than 0.5%, alternatively less than 0.3%, alternatively less than 0.1% by total weight of the composition. Alternatively, the first and/or the second compositions may be free of alkalizing agents. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The any of the first to fourth compositions may comprise a total amount of ammonia of less than 1%, alternatively less than 0.5%, alternatively less than 0.3%, alternatively less than 0.1% by total weight of the composition. Alternatively, the any of the first to fourth compositions may be free of ammonia. These embodiments are particularly interesting in that such compositions are odourless.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The first and/or the second compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the first and/or the second compositions may comprise a total amount of oxidative dye precursors ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dyes

The first and/or the second compositions according to the present invention may further comprise compatible direct dyes, in an amount sufficient to provide additional colouring, particularly with regard to intensity. Typically, the first and/or the second compositions may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-TH-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a, 10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

The first and/or the second compositions according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first and/or the second compositions may comprise a total amount of chelants ranging from at least 0.01%, alternatively from 0.01% to 5%, alternatively from 0.25% to 3%, alternatively from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative —$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first and/or the second compositions according to the present invention may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the first and/or the second compositions may comprise a total amount of radical scavengers ranging from 0.1% to 10%, alternatively from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

Similar to alkalizing agents, pH modifiers and buffering agents are particularly useful to adjust the pH value in the first and second compositions which—as described in detail uner the headline "pH Value"—is inter alia an important parameter for controlling the colour intensity of hair.

The first and/or the second compositions according to the present invention may further comprise, in addition to the alkalizing agent discussed above, a pH modifier and/or buffering agent.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The first and/or the second compositions according to the invention may further comprise a thickener in an amount sufficient to provide the compositions with a viscosity so that it can be readily applied to the hair without unduly dripping off the hair and causing mess.

Typically, the first and/or the second compositions may comprise a total amount of thickeners ranging from at least 0.1%, alternatively at least 0.5%, alternatively at least 1%, by total weight of the composition.

Suitable thickeners include, but are not limited to: associative polymers, polysaccharides such as hydroxyethylcellulose, non-associative polycarboxylic polymers, and mixtures thereof.

Thickeners and/or rheology modifiers in the first and second compositions may have a beneficial impact on the final colour intensity of hair. In principle, the more viscous the composition is, the better is the adherence of the respective polymers to the target surface (e.g., hair surface or polymer chain), For instance, the more viscous the first composition is, the better is the adherence of the coloured cationic polymer on hair. This results in a better interaction between hair and polymer, thereby assisting in achieving a more intensive colour. However, it is not desirable to use an excessive amount of thickeners in the first and/or second compositions since this would hamper the natural diffusion of the respective polymers, thereby limiting the contact times with the target surface. Therefore, a well-balanced concentration of thickeners helps to better control the colour intensity of hair.

Carbonate Ion Sources

The first and/or the second compositions according to the present invention may further comprise a source of carbonate ions, carbamate ions, hydrogen carbonate ions, and mixtures thereof in a sufficient amount to reduce damage to the hair during the colouring process.

Typically, the first and/or the second compositions may comprise a total amount of a carbonate ion source ranging from 0.1% to 15%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The first and/or the second compositions according to the present invention may further comprise a conditioning agent, and/or be used in combination with a composition comprising a conditioning agent.

Typically, the first and/or the second compositions may comprise a total amount of conditioning agents ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerine and sorbitol.

Surfactants

Surfactants help solubilizing the polymers in the solvent. This is particularly important when using polymers (e.g., coloured cationic polymers) having a high weight average molecular weight, e.g. up to 5000 kDa otherwise undesired precipitation might occur.

Any of the first to fourth compositions according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof. Depending on their ionic (or non-ionic) character, surfactants can help adjusting the ionic strength of the first and/or second compositions which may affect the resultant viscosity and root adhesion properties of the respective composition.

Typically, the respective compositions may comprise a total amount of surfactants ranging from 1% to 60%, alternatively from 2% to 30%, alternatively from 8% to 25%, alternatively from 10% to 20%, by total weight of the composition.

Any of the first to fourth compositions may comprise a mixture of an anionic surfactant and an amphoteric surfactant with one or more nonionic surfactants. Alternatively, any of the first to fourth compositions may comprise a mixture of a cationic surfactant and an amphoteric surfactant with one or more nonionic surfactants.

Any of the first to fourth compositions may comprise a total amount of anionic surfactants ranging from 0.1% to 20%, alternatively from 0.1% to 15%, alternatively from 5% to 15%, by total weight of the compositions; and a total amount of amphoteric and/or nonionic components, which may range independently from each other from 0.1% to 15%, alternatively from 0.5% to 10%, alternatively from 1% to 8%, by total weight of the compositions.

Cationic Surfactant(s)

Any of the first to fourth compositions may comprise one or more cationic surfactant(s). The cationic surfactant(s) may preferably comprise one or more linear or branched group(s) comprising at least 8 carbon atoms. The cationic surfactant(s) may more preferably comprise one or more linear or branched group(s) comprising from 8 to 22 carbon atoms. The cationic surfactant(s) may even more preferably comprise one or more linear or branched group(s) comprising from 10 to 22 carbon atoms. The cationic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

While not wishing to be bound by theory, it is believed that the interaction between the cationic surfactant(s) comprised in any of the first to fourth compositions and the first anionic polymer(s) may be stronger than the interaction between the first anionic polymer(s) and the first cationic polymer(s) inside the first polymeric layer and therefore may help to remove a part of the first polymeric layer, i.e. a part of the anionic polymeric sublayer.

While not wishing to be bound by theory, it is believed that the interaction between the cationic surfactant(s) comprised in any of the first to fourth compositions and the first anionic polymer(s) may be even stronger when the first anionic polymer(s) are more hydrophobic, e.g. when the first anionic polymer(s) comprise one or more functional group(s) per polymer chain selected from the group consisting of phenyl group, alkyl groups comprising at least 8 carbon atoms and mixtures thereof.

The cationic surfactant(s) may be selected from the group consisting of quaternary ammonium salts, amido-amines, primary amines, secondary amines, tertiary amines and mixtures thereof.

The cationic surfactant(s) may be selected from quaternary ammonium salts having the following formula:

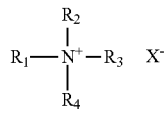

wherein:
$R_1$ is selected from the group consisting of linear or branched groups optionally comprising at least one heteroatom selected from oxygen, nitrogen, sulfur and halogens, wherein the linear or branched groups comprise from 6 to 22 carbon atoms, preferably from 16 to 22 carbon atoms; and $R_2$ is selected from the group consisting of linear or branched groups optionally comprising at least one heteroatom selected from oxygen, nitrogen, sulfur and halogens, wherein the linear or branched groups comprise from 1 to 22 carbon atoms, preferably from 16 to 22 carbon atoms, aryl groups and alkylaryl groups; and $R_3$ and $R_4$ are independently selected from the group consisting of linear or branched groups comprising from 1 to 4 carbon atoms, aryl groups and alkylaryl groups; and $X^-$ is an anion selected from chloride, bromide, iodide, alkyl sulfates, phosphates, alkyl sulfonates, alkylaryl sulfonates and anions derived from organic acids or amino acids.

The linear or branched groups may be aliphatic groups. The aliphatic groups may be selected from alkyl, alkoxy and alkylamide groups.

The amino acid may be glutamic acid. The anions derived from organic acids may be acetate anions or lactates anions.

The cationic surfactant(s) may be selected from amido-amines having the following formula:

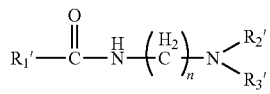

wherein:
$R_{1'}$ is selected from the group consisting of linear or branched groups optionally comprising at least one heteroatom selected from oxygen, nitrogen, sulfur and halogens, wherein the linear or branched groups comprise from 10 to 22 carbon atoms, preferably from 16 to 22 carbon atoms;

$R'_2$ and $R'_3$ are independently selected from the group consisting of hydrogen, linear or branched groups optionally comprising at least one heteroatom selected from oxygen, nitrogen, sulfur and halogens, wherein the linear or branched groups comprise from 1 to 4 carbon atoms, aryl groups and alkylaryl groups;

n is integer ranging from 1 to 4.

The linear or branched groups may be aliphatic groups. The aliphatic groups may be selected from alkyl, alkoxy and alkylamide groups.

The cationic surfactant(s) may be selected from the group consisting of cetrimonium halide, stearimonium halide, behentrimonium halide, behentrimonium halide, stearamidopropyltrimonium halide, dodecyltrimethylammonium halide, didodecyldimethylammonium halide, tetradecyltrimethylammonium halide, distearyldimethylammonium halide, dicetyldimethylammonium halide, distearoylethyl dimonium halide, behenamidopropyltrimonium methosulfate, behenamidopropyl dimethylamine, stearamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures thereof, wherein the halide is selected from bromide and chloride. The cationic surfactant(s) may preferably be selected from the group consisting of dodecyltrimethylammonium halide, didodecyldimethylammonium halide, tetradecyltrimethylammonium halide, cetrimonium halide and mixtures thereof, wherein the halide is selected from bromide and chloride.

Any of the first to fourth compositions comprises a total amount of cationic surfactants ranging from 0.01% to 10%, preferably from 0.05% to 5%, more preferably from 0.3% to 3% by total weight of the respective composition. The amount of each particular cationic surfactant or mixtures thereof described hereinbefore can account for up to 100% (or 100%) of the total amount of cationic surfactants in the respective composition.

Amphoteric Surfactant(s)

Any of the first to fourth compositions may comprise one or more amphoteric surfactant(s). The amphoteric surfactant(s) may preferably comprise one or more linear or branched group(s) comprising at least 8 carbon atoms. The amphoteric surfactant(s) may more preferably comprise one or more linear or branched group(s) comprising from 8 to 40 carbon atoms. The amphoteric surfactant(s) may even more preferably comprise one or more linear or branched group(s) comprising from 10 to 40 carbon atoms. The amphoteric surfactant(s) may most preferably comprise one or more linear or branched group(s) comprising from 16 to 35 carbon atoms. The linear or branched group(s) may optionally comprise at least one heteroatom selected from oxygen, nitrogen, sulfur and halogens. The linear or branched groups may be aliphatic groups.

Amphoteric (zwitterionic) surfactants have both cationic and anionic centers attached to the same molecule. The cationic part may be based on primary, secondary, tertiary amines or quaternary ammonium cations. The anionic part can be more variable and may include sulfonates, as in the sultaines CHAPS (3-[(3-Cholamidopropyl)dimethylammonio]-1-propanesulfonate) and cocamidopropyl hydroxysultaine.

Suitable amphoteric surfactants may include betaines, such as cocamidopropyl betaine, phospholipids, such as phosphatidylserine, phosphatidylethanolamine, phosphatidylcholine, and sphingomyelins.

Suitable betaines may have the following formula

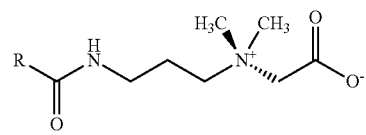

with R=alkyl chain with 5 to 21 C atoms.

Further suitable amphoteric surfactants may include sultaines which may have the following formula

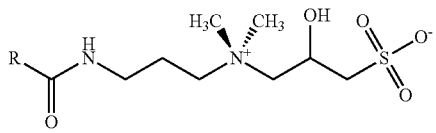

with R=alkyl chain with 5 to 21 C atoms.

Further suitable amphoteric surfactants may include taurin (2-aminoethansulfonic acid), cocoamidopropyl hydroxysultain, N-coco 3-aminopropionic acid, (or the sodium salt thereof), N-tallow 3-iminodipropionate (or the disodium salt thereof), N-carboxymethyl N-dimethyl N-9 octadecenyl ammonium hydroxide, N-cocoamidethyl N-hydroxyethylglycine, cocoamphocarboxyglycinate, cocamidopropyl betaine, and sulfobetaine.

Most preferred amphoteric surfactants are selected from the group consisting of betain, sultaines, phospholipids, aminopropionates, aminoglycinates, amphoacetate, amphodiacetate, amphopropionate, amphohydroxypropylsulfonates, and combinations thereof. Most preferred are betains selected from the group consisting of Cocamidopropyl betaine, Laurylamidopropyl betaine Tetradecyl betaine, Alkylaminopropyl betaine, Octyl betain, Cetyl betain, Staeryl betain. Amino acid Further suitable amphoteric surfactants may comprise amino acids. Specifically, amino acids with their polyampholytic character in any of the first to fourth compositions can help to enhance the ionic and hydrophobic interactions between the hair surface. Suitable amino acids may be selected from the group consisting of alanine, arginine, asparagine, aspartic acid, cysteine, glutamic acid, glutamine, glycine, proline, selenocysteine, serine, tyrosine, histidine, isoleucine, leucine, lysine, methionine, phenylalanine, threonine, tryptophan, valine, and combinations thereof.

According to an embodiment, any of the first to fourth compositions may comprise one or more anionic surfactant(s). The anionic surfactant(s) may include, for example, sodium dodecyl sulfate SDS, sodium xylenesulfonat sodium naphthalenesulfonate, dodecyl trimethyl ammonium bromid, sodium lauryl sulfate SDS, Tween 20.
Nonionic Surfactant(s)

Any of the first to fourth compositions may comprise one or more nonionic surfactant(s). The nonionic surfactant(s) may preferably comprise one or more linear or branched group(s) comprising at least 8 carbon atoms. The nonionic surfactant(s) may more preferably comprise one or more linear or branched group(s) comprising from 8 to 22 carbon atoms. The nonionic surfactant(s) may even more preferably comprise one or more linear or branched group(s) comprising from 10 to 22 carbon atoms. The nonionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

The nonionic surfactants may be selected form the group consisting of alkohols, ethers, esthers, alkanolamides and aminoxides.

Suitable alcohols may include primary alcohols ranging from 8 to 18 carbon atoms. Preferred primary alcohols are fatty alcohols, cetyl alcohol, stearyl alcohol, cetostearyl alcohol (consisting predominantly of cetyl and stearyl alcohols), and oleyl alcohol.

Suitable ethers may include Polyoxyethylene glycol alkyl ethers (Brij) (CH3-(CH2)10-16-(O—C2H4)1-25-OH), Octaethylene glycol monododecyl ether, Pentaethylene glycol monododecyl ether, Polyoxypropylene glycol alkyl ethers (CH3-(CH2)10-16-(O—C3H6)1-25-OH), Glucoside alkyl ethers (CH3-(CH2)10-16-(O-Glucoside)1-3-OH), Decyl glucoside, Lauryl glucoside, Octyl glucoside, Polyoxyethylene glycol octylphenol ethers (C8H17-(C6H4)-(O—C2H4)1-25-OH, Triton X-100), Polyoxyethylene glycol alkylphenol ethers (C9H19-(C6H4)-(O—C2H4)1-25-OH, Nonoxynol-9), and block copolymers of polyethylene glycol and polypropylene glycol (Poloxamers).

Suitable esthers may include Glycerol alkyl esters, such as Glyceryl laurate, Polyoxyethylene glycol sorbitan alkyl esters, such as Polysorbate, and Sorbitan alkyl esters, such as Spans.

Suitable alkanolamides may include cocamide MEA, cocamide DEA

Suitable aminoxides may include Dodecyldimethylamine oxide and Polyethoxylated tallow amine (POEA).
Anionic Surfactant(s)

Any of the first to fourth compositions may comprise one or more anionic surfactant(s). The anionic surfactant(s) may preferably comprise one or more linear or branched group(s) comprising at least 8 carbon atoms. The anionic surfactant(s) may more preferably comprise one or more linear or branched group(s) comprising from 8 to 22 carbon atoms. The anionic surfactant(s) may even more preferably comprise one or more linear or branched group(s) comprising from 10 to 22 carbon atoms. The anionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants are selected from the group consisting of sodium laurylethersulfate, sodium lauretheth-ersulfate, sodium dodecyl sulfate, ammonium laurethethersulfat, ammonium dodecyl sulfate, alkylbenzenesulfonate, and combinations thereof.
Ionic Strength The first and/or the second compositions of the present invention may further have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS, as well as surfactants. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17$ M.

Foam

The first and/or second compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Molecular Weight

According to an embodiment, the one or more cationic polymer(s) of the first composition and may have a higher molecular weight than the one or more cationic polymer(s) of the third composition. Using a higher molecular weight may allow the formation of a thicker and/or denser polymeric sublayer which may be beneficial for the following layers and also for the removal of the coloured layers.

The molecular weight is expressed as weight average molecular weight.

According to an embodiment, the third composition comprising one or more second cationic polymer(s) being cationic coloured polymer(s) and/or the fourth composition comprising one or more second anionic polymer(s) being anionic coloured polymer(s) is/are substantially free from low molecular weight compounds selected from the group consisting of coloured polymer(s), coloured monomer(s), unbound chromophore(s), and fluorophore(s), and mixtures thereof. According to an embodiment, "low molecular weight compounds" are compounds having a molecular weight of less than 500 Da, particularly less than 1 kDa, more particularly less than 2 kDa, even more particularly less than 3 kDa, and further more particularly less than 5 kDa. According to an embodiment, "substantially free" may mean less than 1000 ppm, particularly less than 500 ppm, more particularly less than 100 ppm, and even more particularly less than 50 ppm. The monomers mentioned above mean the monomeric units from which the polymers are made. 1 ppm corresponds to 1 µg/kg polymer.

According to an embodiment, the molecular weight distribution of the cationic coloured polymer(s) and/or of the anionic coloured polymer(s) may be substantially free from low molecular weight polymeric compounds as described above. Such a molecular weight distribution may be obtained by suitable purification steps such as dialysis or filtration.

Avoiding low molecular weight compounds that includes chromophores and/or fluorophores may avoid that such low molecular weight compounds diffuse through the polymeric layer, which may be uncoloured, and interact with the hair. Such low molecular weight compounds may then remain on the hair which may result in unwanted reactions.

According to an embodiment, the molecular weight for the coloured polymers may be in the ranges as described further above in connection with the third and fourth composition, or may also have a lower limit of 15 kDa, particularly of 25 kDa, and more particularly of 40 kDa, and an upper limit of 300 kDa, particularly 200 kDa, and more particularly 150 kDa. Specific examples are 25 kDa to 300 kDa, 25 kDa to 150 kDa, 40 kDa to 200 kDa, 40 kDa to 150 kDa, and 70 kDa to 150 kDa, without being limited thereto.

Improved Polymer Loading of First Polymeric Layer

According to an embodiment, the first composition may have a first pH value, the second composition may have a second pH value, the third composition may have a third pH value, and the fourth composition may have a fourth pH value. The pH values can be different from each other.

According to an embodiment, the first composition comprising one or more first cationic polymer(s) has a first pH value higher than third pH value of the third composition comprising one or more second cationic polymer(s) and/or one or more pigment(s). Without wishing to be tight by theory, it is believed that a higher pH value renders the first cationic polymer(s) less charged resulting in an increased loading of the hair surface with the first cationic polymer(s). The cationic polymeric sublayer of the first polymeric layer can thus be provided with a higher polymer loading. This also improves the binding, and loading, of the subsequently formed anionic polymeric sublayer.

The third pH of the third composition may be lower than the first pH value of the first composition to avoid that a high pH weakens the interaction between the previously formed polymeric sublayers bound to keratin fibres of the hair. However, since the polymer loading of the cationic polymeric sublayer of the first polymeric layer is increased as described above, the anionic polymeric sublayer also shows an increased loading which facilitates binding of the second cationic polymer(s).

For example, the first composition may have a pH value (first pH value) higher than 8, particularly higher than 8.5, more particularly higher than 9, and even more particularly higher than 9.5. The first composition may have a pH value less than 13, particularly less than 12, more particularly less than 11, and even more particularly less than 10.5. An example is a pH in a range from 8 to 13, particularly from 8.5 to 12 or 8 to 11, more particularly from 8.5 to 11 or 9 to 11, and even more particularly from 9 to 10.5.

The third composition may have a pH value (fourth pH value) less than 9.5, particularly less than 9, more particularly less than 8.5, and even more particularly less than 8.

According to an embodiment, the difference of the pH values (first and third pH values) of the first composition and the third composition can be at least 0.5, particularly at least 1, and more particularly at least 1.5.

The pH of the second composition may be higher than the pH of the fourth composition to avoid that a too low pH of the second composition weakens the interaction between the previously formed polymeric sublayers bound to keratin fibres of the hair. However, since the polymer loading of the cationic polymeric sublayer of the first polymeric layer is increased as described above, the anionic polymeric sublayer also shows an increased loading which facilitates binding of the second cationic polymer(s).

The second cationic polymer(s) of the third composition may be coloured while the first cationic polymer(s) of the first composition may be uncoloured.

In addition to that, the second composition comprising one or more first anionic polymer(s) may have a pH value (second pH value) lower than the first composition. At the lower pH, it is believed that the first cationic polymer(s) linked to the hair are highly charged thus presenting more charges to the first anionic layer polymer(s) so that the anionic polymeric sublayer is strongly bound and has a higher loading.

According to an embodiment, the first pH value can be higher than the second pH value.

According to an embodiment, the fourth pH value can be lower than the first pH value.

According to an embodiment, the one or more second anionic coloured polymer(s) of the fourth composition may include an anionic polymer backbone and at least one cationic chromophore and/or cationic fluorophore linked to the anionic polymer backbone. The overall charge of the second anionic coloured polymer(s) is such that the second anionic coloured polymer(s) is anionic at the pH of the fourth composition. Having the second anionic coloured polymer(s) provided with cationic groups by linking the cationic chromophores and/or cationic fluorophores further facilitates removal of the second anionic coloured polymer(s) by applying the third composition. Due to the cationic groups of the chromophore and/or fluorophores the second anionic coloured polymer(s) may become neutral or even inversely charged when the third composition is applied which improves removal of the second cationic coloured polymer(s).

The same also applies to anionic coloured polymer(s) of other compositions which may be subsequently applied. Hence, the invention may include a polymeric layer structure on keratin fibres of the hair having one or more first cationic uncoloured polymer(s), one or more first anionic uncoloured polymer(s), one or more second cationic coloured polymer(s), and one or more second anionic coloured polymer(s), wherein the one or more second anionic coloured polymer(s) includes a anionic polymer backbone and at least one cationic chromophore and/or cationic fluorophore linked to the anionic polymer backbone.

The invention may include a polymeric layer structure on keratin fibres of the hair having one or more first cationic uncoloured polymer(s), one or more first anionic uncoloured polymer(s), and one or more second anionic coloured polymer(s), wherein the one or more second anionic coloured polymer(s) includes an anionic polymer backbone and at least one cationic chromophore and/or cationic fluorophore linked to the anionic polymer backbone.

Exemplary Hair Colouring Systems

Most preferred hair colouring systems are as follows:

A) Systems Based on a Coloured Linear or Branched Polyethyleneimine (PEI)

Coloured linear or branched polyethyleneimine (PEI) of the formula (I) is defined as follows:

A coloured linear or branched polyethyleneimine (PEI) of the formula:

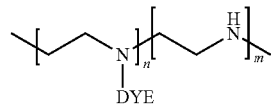

in which n and m are integers representing the degree of polymerization, wherein m/n ranges from 0 to 1,000 provided that n is different from 0 and/or m+n ranges from 50 to 20,000, alternatively from 100 to 3,500;

wherein the DYE is a chromophore which is selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

1. A hair colouring system for providing a multilayer structure on an area of hair, the system comprising a first composition comprising
   a coloured linear or branched polyethyleneimine (PEI) of the formula (I), wherein the labelling degree k is 1:2 to 1:10, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

2. A hair colouring system for providing a multilayer structure on an area of hair, the system comprising a first composition comprising
   a coloured linear or branched polyethyleneimine (PEI) of the formula (I), wherein the labelling degree k is 1:11 to 1:20, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

3. A hair colouring system for providing a multilayer structure on an area of hair, the system comprising a first composition comprising
   a coloured linear or branched polyethyleneimine (PEI) of the formula (I), wherein the labelling degree k is 1:21 to 1:30, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

4. A hair colouring system for providing a multilayer structure on an area of hair, the system comprising a first composition comprising
a coloured linear or branched polyethyleneimine (PEI) of the formula (I) wherein the labelling degree k is 1:31 to 1:40, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

5. A hair colouring system for providing a multilayer structure on an area of hair, the system comprising a first composition comprising
a coloured linear or branched polyethyleneimine (PEI) of the formula (I), wherein the labelling degree k is 1:41 to 1:50, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

6. A hair colouring system for providing a multilayer structure on an area of hair, the system comprising a first composition comprising
a coloured linear or branched polyethyleneimine (PEI) of the formula (I), wherein the labelling degree k is 1:51 to 1:60, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

7. A hair colouring system for providing a multilayer structure on an area of hair, the system comprising a first composition comprising
a coloured linear or branched polyethyleneimine (PEI) of the formula (I), wherein the labelling degree k is 1:61 to 1:70, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

8. A hair colouring system for providing a multilayer structure on an area of hair, the system comprising a first composition comprising
a coloured linear or branched polyethyleneimine (PEI) of the formula (I), wherein the labelling degree k is 1:71 to 1:80, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

9. A hair colouring system for providing a multilayer structure on an area of hair, the system comprising a first composition comprising
a coloured linear or branched polyethyleneimine (PEI) of the formula (I), wherein the labelling degree k is 1:81 to 1:90, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

10. A hair colouring system for providing a multilayer structure on an area of hair, the system comprising a first composition comprising
a coloured linear or branched polyethyleneimine (PEI) of the formula (I), wherein the labelling degree k is 1:91 to 1:100, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

11. A hair colouring system for providing a multilayer structure on an area of hair, the system comprising a first composition comprising
a coloured linear or branched polyethyleneimine (PEI) of the formula (I), wherein the labelling degree k is 1:1100 to 1:2000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

12. A hair colouring system for providing a multilayer structure on an area of hair, the system comprising a first composition comprising
   a coloured linear or branched polyethyleneimine (PEI) of the formula (I), wherein the labelling degree k is 1:1201 to 1:5000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

13. A hair colouring system for providing a multilayer structure on an area of hair, the system comprising a first composition comprising
   a coloured linear or branched polyethyleneimine (PEI) of the formula (I), wherein the labelling degree k is 1:5001 to 1:10,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

14. A hair colouring system for providing a multilayer structure on an area of hair, the system comprising a first composition comprising
   a coloured linear or branched polyethyleneimine (PEI) of the formula (I), wherein the labelling degree k is 1:10,001 to 20,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

15. A hair colouring system for providing a multilayer structure on an area of hair, the system comprising a first composition comprising
   a coloured linear or branched polyethyleneimine (PEI) of the formula (I), wherein the labelling degree k is 1:20,001 to 50,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

16. A hair colouring system for providing a multilayer structure on an area of hair, the system comprising a first composition comprising
   a coloured linear or branched polyethyleneimine (PEI) of the formula (I), wherein the labelling degree k is 1:50,001 to 100,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

17. A hair colouring system for providing a multilayer structure on an area of hair, the system comprising a first composition comprising
   a coloured linear or branched polyethyleneimine (PEI) of the formula (I), wherein the labelling degree k is 1:100,001 to 200,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

18. A hair colouring system for providing a multilayer structure on an area of hair, the system comprising a first composition comprising
   a coloured linear or branched polyethyleneimine (PEI) of the formula (I), wherein the labelling degree k is 1:200,001 to 300,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

19. A hair colouring system for providing a multilayer structure on an area of hair, the system comprising a first composition comprising
   a coloured linear or branched polyethyleneimine (PEI) of the formula (I), wherein the labelling degree k is 1:300,001 to 400,000, and
   a second composition comprising at least one anionic polymer,
   the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

20. A hair colouring system for providing a multilayer structure on an area of hair, the system comprising a first composition comprising
   a coloured linear or branched polyethyleneimine (PEI) of the formula (I), wherein the labelling degree k is 1:400,001 to 500,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

21. A hair colouring system for providing a multilayer structure on an area of hair, the system comprising a first composition comprising a coloured linear or branched polyethyleneimine (PEI) of the formula (I), wherein the labelling degree k is 1:500,001 to 600,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

22. A hair colouring system for providing a multilayer structure on an area of hair, the system comprising a first composition comprising a coloured linear or branched polyethyleneimine (PEI) of the formula (I), wherein the labelling degree k is 1:600,001 to 700,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

23. A hair colouring system for providing a multilayer structure on an area of hair, the system comprising a first composition comprising a coloured linear or branched polyethyleneimine (PEI) of the formula (I), wherein the labelling degree k is 1:700,001 to 800,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

24. A hair colouring system for providing a multilayer structure on an area of hair, the system comprising a first composition comprising a coloured linear or branched polyethyleneimine (PEI) of the formula (I), wherein the labelling degree k is 1:800,001 to 900,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

25. A hair colouring system for providing a multilayer structure on an area of hair, the system comprising a first composition comprising a coloured linear or branched polyethyleneimine (PEI) of the formula (I), wherein the labelling degree k is 1:900,001 to 1,000,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

Each of the above described systems based on a coloured linear or branched polyethyleneimine (PEI) according to items 1 to 25 can have the following additional features a) to g) and any combination thereof:

a) The first composition may have a pH ranging from 6 to 11, alternatively from 7 to 11, alternatively from 7 to 10.5, alternatively from 7.5 to 10.5, more alternatively from 7.5 to 10, even more alternatively from 8 to 10.

a) The second composition may have a pH ranging from 3 to 10, alternatively from 4 to 9, more alternatively from 4 to 9, even more alternatively from 4 to 8.

b) The first composition may comprise a cosmetically acceptable salt at a concentration ranging from 0 to 1.5 mol/L, preferably from 0.05 to 1 mol/L, more preferably from 0.2 to 0.5 mol/L.

c) The second composition may comprise a cosmetically acceptable salt at a concentration ranging from 0 to 1.5 mol/L, preferably from 0.05 to 1 mol/L, more preferably from 0.2 to 0.5 mol/L.

d) The first and/or second compositions may comprise pH modifiers and/or buffering agents selected from the group consisting of ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

e) The first and/or second compositions may comprise thickeners (i.e. rheology modifiers) selected from the group consisting of associative polymers, polysaccharides, non-associative polycarboxylic polymers, and mixtures thereof.

f) The first and/or second compositions may comprise surfactants selected from the group consisting of anionic surfactants, nonionic surfactants, amphoteric surfactants, cationic surfactants, and mixtures thereof.

g) The first and/or second compositions may comprise conditioning agents selected from the group consisting of silicones, aminosilicones, fatty alcohols, polymeric resins, polyol carboxylic acid esters, cationic polymers, cationic surfactants, oil derived materials, insoluble oils such as mineral oils, other oils such as glycerin and sorbitol, and mixtures thereof.
h) The first and/or the second compositions of the present invention may further have an ionic strength as defined herein of less than about 1.35 mole/kg, alternatively from about 0.10 to about 0.75 mole/kg, alternatively from about 0.20 to about 0.60 mole/kg.

B) Systems Based on a Coloured Polyallylamine Hydrochloride

A coloured polyallylamine hydrochloride formula (II) is defined as follows:
a coloured polyallylamine hydrochloride of the formula:

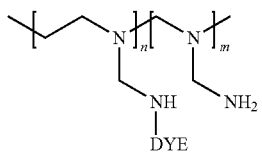

in which n and m are integers representing the degree of polymerization, wherein m/n ranges from 0 to 1,000 provided that n is different from 0 and/or m+n ranges from 50 to 20,000, alternatively from 150 to 2000 alternatively from 150 to 800;
wherein the DYE is a chromophore which is selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

1. A hair colouring system for providing a multilayer structure on an area of hair, the system comprising a first composition comprising
a coloured polyallylamine hydrochloride of the formula (II), wherein the labelling degree k is 1:2 to 1:10, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

2. A hair colouring system for providing a multilayer structure on an area of hair, the system comprising a first composition comprising
a coloured polyallylamine hydrochloride of the formula (II),
wherein the labelling degree k is 1:11 to 1:20, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

3. A hair colouring system for providing a multilayer structure on an area of hair, the system comprising a first composition comprising
a coloured polyallylamine hydrochloride of the formula (II), wherein the labelling degree k is 1:21 to 1:30, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

4. A hair colouring system for providing a multilayer structure on an area of hair, the system comprising a first composition comprising
a coloured polyallylamine hydrochloride of the formula (II), wherein the labelling degree k is 1:31 to 1:40, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), X-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

5. A hair colouring system for providing a multilayer structure on an area of hair, the system comprising a first composition comprising
a coloured polyallylamine hydrochloride of the formula (II), wherein the labelling degree k is 1:41 to 1:50, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

6. A hair colouring system for providing a multilayer structure on an area of hair, the system comprising a first composition comprising
a coloured polyallylamine hydrochloride of the formula (II), wherein the labelling degree k is 1:51 to 1:60, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

7. A hair colouring system for providing a multilayer structure on an area of hair, the system comprising a first composition comprising a coloured polyallylamine hydrochloride of the formula (II), wherein the labelling degree k is 1:61 to 1:70, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

8. A hair colouring system for providing a multilayer structure on an area of hair, the system comprising a first composition comprising a coloured polyallylamine hydrochloride of the formula (II), wherein the labelling degree k is 1:71 to 1:80, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

9. A hair colouring system for providing a multilayer structure on an area of hair, the system comprising a first composition comprising a coloured polyallylamine hydrochloride of the formula (II), wherein the labelling degree k is 1:81 to 1:90, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

10. A hair colouring system for providing a multilayer structure on an area of hair, the system comprising a first composition comprising a coloured polyallylamine hydrochloride of the formula (II), wherein the labelling degree k is 1:91 to 1:100, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

11. A hair colouring system for providing a multilayer structure on an area of hair, the system comprising a first composition comprising a coloured polyallylamine hydrochloride of the formula (II), wherein the labelling degree k is 1:1100 to 1:2000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

12. A hair colouring system for providing a multilayer structure on an area of hair, the system comprising a first composition comprising a coloured polyallylamine hydrochloride of the formula (II), wherein the labelling degree k is 1:1201 to 1:5000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

13. A hair colouring system for providing a multilayer structure on an area of hair, the system comprising a first composition comprising a coloured polyallylamine hydrochloride of the formula (II), wherein the labelling degree k is 1:5001 to 1:10,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

14. A hair colouring system for providing a multilayer structure on an area of hair, the system comprising a first composition comprising a coloured polyallylamine hydrochloride of the formula (II), wherein the labelling degree k is 1:10,001 to 20,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

15. A hair colouring system for providing a multilayer structure on an area of hair, the system comprising a first composition comprising a coloured polyallylamine hydrochloride of the formula (II), wherein the labelling degree k is 1:20,001 to 50,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

16. A hair colouring system for providing a multilayer structure on an area of hair, the system comprising a first composition comprising
a coloured polyallylamine hydrochloride of the formula (II), wherein the labelling degree k is 1:50,001 to 100,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

17. A hair colouring system for providing a multilayer structure on an area of hair, the system comprising a first composition comprising
a coloured polyallylamine hydrochloride of the formula (II), wherein the labelling degree k is 1:100,001 to 200,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

18. A hair colouring system for providing a multilayer structure on an area of hair, the system comprising a first composition comprising
a coloured polyallylamine hydrochloride of the formula (II), wherein the labelling degree k is 1:200,001 to 300,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

19. A hair colouring system for providing a multilayer structure on an area of hair, the system comprising a first composition comprising
a coloured polyallylamine hydrochloride of the formula (II), wherein the labelling degree k is 1:300,001 to 400,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

20. A hair colouring system for providing a multilayer structure on an area of hair, the system comprising a first composition comprising
a coloured polyallylamine hydrochloride of the formula (II), wherein the labelling degree k is 1:400,001 to 500,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

21. A hair colouring system for providing a multilayer structure on an area of hair, the system comprising a first composition comprising
a coloured polyallylamine hydrochloride of the formula (II), wherein the labelling degree k is 1:500,001 to 600,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

22. A hair colouring system for providing a multilayer structure on an area of hair, the system comprising a first composition comprising
a coloured polyallylamine hydrochloride of the formula (II), wherein the labelling degree k is 1:600,001 to 700,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

23. A hair colouring system for providing a multilayer structure on an area of hair, the system comprising a first composition comprising
a coloured polyallylamine hydrochloride of the formula (II), wherein the labelling degree k is 1:700,001 to 800,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

24. A hair colouring system for providing a multilayer structure on an area of hair, the system comprising a first composition comprising a coloured polyallylamine hydrochloride of the formula (II), wherein the labelling degree k is 1:800,001 to 900,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

25. A hair colouring system for providing a multilayer structure on an area of hair, the system comprising a first composition comprising a coloured polyallylamine hydrochloride of the formula (II), wherein the labelling degree k is 1:900,001 to 1,000,000, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

Each of the above described systems based on a coloured polyallylamine hydrochloride according to items 1 to 25 can have the following additional features a) to g) and any combination thereof:

a) The first composition may have a pH ranging from 6 to 11, alternatively from 7 to 11, alternatively from 7 to 10.5, alternatively from 7.5 to 10.5, more alternatively from 7.5 to 10, even more alternatively from 8 to 10.

b) The second composition may have a pH ranging from 3 to 10, alternatively from 4 to 9, more alternatively from 4 to 9, even more alternatively from 4 to 8.

c) The first composition may comprise a cosmetically acceptable salt at a concentration ranging from 0 to 1.5 mol/L, preferably from 0.05 to 1 mol/L, more preferably from 0.2 to 0.5 mol/L.

d) The second composition may comprise a cosmetically acceptable salt at a concentration ranging from 0 to 1.5 mol/L, preferably from 0.05 to 1 mol/L, more preferably from 0.2 to 0.5 mol/L.

e) The first and/or second compositions may comprise pH modifiers and/or buffering agents selected from the group consisting of ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

f) The first and/or second compositions may comprise thickeners (i.e. rheology modifiers) selected from the group consisting of associative polymers, polysaccharides, non-associative polycarboxylic polymers, and mixtures thereof.

g) The first and/or second compositions may comprise surfactants selected from the group consisting of anionic surfactants, nonionic surfactants, amphoteric surfactants, cationic surfactants, and mixtures thereof.

h) The first and/or second compositions may comprise conditioning agents selected from the group consisting of silicones, aminosilicones, fatty alcohols, polymeric resins, polyol carboxylic acid esters, cationic polymers, cationic surfactants, oil derived materials, insoluble oils such as mineral oils, other oils such as glycerin and sorbitol, and mixtures thereof.

i) The first and/or the second compositions of the present invention may further have an ionic strength as defined herein of less than about 1.35 mole/kg, alternatively from about 0.10 to about 0.75 mole/kg, alternatively from about 0.20 to about 0.60 mole/kg.

C) Systems Based on a Coloured Polydiallyldimethylammonium Chloride

A coloured polydiallyldimethylammonium chloride of the formula (III) is defined as:

a coloured polydiallyldimethylammonium chloride of the formula:

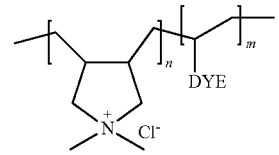

in which n and m are integers representing the degree of polymerization, wherein m/n ranges from 0 to 1,000 provided that n is different from 0 and/or m+n ranges from 50 to 20,000, alternatively from 100 to 4000, alternatively from 100 to 3,500;

wherein the DYE is a chromophore which is selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof, and 1. A hair colouring system for providing a multilayer structure on an area of hair, the system comprising a first composition comprising a coloured polydiallyldimethylammonium chloride of the formula (III), wherein the labelling degree k is 1:2 to 1:10, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

2. A hair colouring system for providing a multilayer structure on an area of hair, the system comprising a first composition comprising a coloured polydiallyldimethylammonium chloride of the formula (III), wherein the labelling degree k is 1:11 to 1:20, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

3. A hair colouring system for providing a multilayer structure on an area of hair, the system comprising a first composition comprising a coloured polydiallyldimethylammonium chloride of the formula (III), wherein the labelling degree k is 1:21 to 1:30, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

4. A hair colouring system for providing a multilayer structure on an area of hair, the system comprising a first composition comprising a coloured polydiallyldimethylammonium chloride of the formula (III), wherein the labelling degree k is 1:31 to 1:40, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

5. A hair colouring system for providing a multilayer structure on an area of hair, the system comprising a first composition comprising a coloured polydiallyldimethylammonium chloride of the formula (III), wherein the labelling degree k is 1:41 to 1:50, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

6. A hair colouring system for providing a multilayer structure on an area of hair, the system comprising a first composition comprising a coloured polydiallyldimethylammonium chloride of the formula (III), wherein the labelling degree k is 1:51 to 1:60, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

7. A hair colouring system for providing a multilayer structure on an area of hair, the system comprising a first composition comprising a coloured polydiallyldimethylammonium chloride of the formula (III), wherein the labelling degree k is 1:61 to 1:70, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

8. A hair colouring system for providing a multilayer structure on an area of hair, the system comprising a first composition comprising a coloured polydiallyldimethylammonium chloride of the formula (III), wherein the labelling degree k is 1:71 to 1:80, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

9. A hair colouring system for providing a multilayer structure on an area of hair, the system comprising a first composition comprising a coloured polydiallyldimethylammonium chloride of the formula (III), wherein the labelling degree k is 1:81 to 1:90, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

10. A hair colouring system for providing a multilayer structure on an area of hair, the system comprising a first composition comprising a coloured polydiallyldimethylammonium chloride of the formula (III), wherein the labelling degree k is 1:91 to 1:100, and a second composition comprising at least one anionic polymer, the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

11. A hair colouring system for providing a multilayer structure on an area of hair, the system comprising a first composition comprising
a coloured polydiallyldimethylammonium chloride of the formula (III), wherein the labelling degree k is 1:1100 to 1:2000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

12. A hair colouring system for providing a multilayer structure on an area of hair, the system comprising a first composition comprising
a coloured polydiallyldimethylammonium chloride of the formula (III), wherein the labelling degree k is 1:1201 to 1:5000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

13. A hair colouring system for providing a multilayer structure on an area of hair, the system comprising a first composition comprising
a coloured polydiallyldimethylammonium chloride of the formula (III), wherein the labelling degree k is 1:5001 to 1:10,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

14. A hair colouring system for providing a multilayer structure on an area of hair, the system comprising a first composition comprising
a coloured polydiallyldimethylammonium chloride of the formula (III), wherein the labelling degree k is 1:10,001 to 1:20,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

15. A hair colouring system for providing a multilayer structure on an area of hair, the system comprising a first composition comprising
a coloured polydiallyldimethylammonium chloride of the formula (III), wherein the labelling degree k is 1:20,001 to 50,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

16. A hair colouring system for providing a multilayer structure on an area of hair, the system comprising a first composition comprising
a coloured polydiallyldimethylammonium chloride of the formula (III), wherein the labelling degree k is 1:50,001 to 100,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

17. A hair colouring system for providing a multilayer structure on an area of hair, the system comprising a first composition comprising
a coloured polydiallyldimethylammonium chloride of the formula (III), wherein the labelling degree k is 1:100,001 to 200,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

18. A hair colouring system for providing a multilayer structure on an area of hair, the system comprising a first composition comprising
a coloured polydiallyldimethylammonium chloride of the formula (III), wherein the labelling degree k is 1:200,001 to 300,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

19. A hair colouring system for providing a multilayer structure on an area of hair, the system comprising a first composition comprising
a coloured polydiallyldimethylammonium chloride of the formula (III), wherein the labelling degree k is 1:300,001 to 400,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

20. A hair colouring system for providing a multilayer structure on an area of hair, the system comprising a first composition comprising
a coloured polydiallyldimethylammonium chloride of the formula (III), wherein the labelling degree k is 1:400,001 to 500,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

21. A hair colouring system for providing a multilayer structure on an area of hair, the system comprising a first composition comprising
a coloured polydiallyldimethylammonium chloride of the formula (III), wherein the labelling degree k is 1:500,001 to 600,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

22. A hair colouring system for providing a multilayer structure on an area of hair, the system comprising a first composition comprising
a coloured polydiallyldimethylammonium chloride of the formula (III), wherein the labelling degree k is 1:600,001 to 700,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

23. A hair colouring system for providing a multilayer structure on an area of hair, the system comprising a first composition comprising
a coloured polydiallyldimethylammonium chloride of the formula (III), wherein the labelling degree k is 1:700,001 to 800,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

24. A hair colouring system for providing a multilayer structure on an area of hair, the system comprising a first composition comprising
a coloured polydiallyldimethylammonium chloride of the formula (III), wherein the labelling degree k is 1:800,001 to 900,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

25. A hair colouring system for providing a multilayer structure on an area of hair, the system comprising a first composition comprising
a coloured polydiallyldimethylammonium chloride of the formula (III), wherein the labelling degree k is 1:900,001 to 1,000,000, and
a second composition comprising at least one anionic polymer,
the anionic polymer being a selected from the group comprising polystyrene sulfonate (PSS), co-polymer of polystyrene sulfonate (PSS) sodium salt and poly(4-styrenesulfonic acid-co-maleic acid), λ-Carrageenan, polyacrylic acid (PAA), alginic acid sodium salts, carboxymethylcellulose sodium salt, polysaccharide such as Dextrans and Dextran sulfate sodium salts, copolymers thereof and mixtures thereof.

Each of the above described systems based on a coloured polydiallyldimethylammonium chloride according to items 1 to 25 can have the following additional features a) to g) and any combination thereof:
a) The first composition may have a pH ranging from 6 to 11, alternatively from 7 to 11, alternatively from 7 to 10.5, alternatively from 7.5 to 10.5, more alternatively from 7.5 to 10, even more alternatively from 8 to 10.
b) The second composition may have a pH ranging from 3 to 10, alternatively from 4 to 9, more alternatively from 4 to 9, even more alternatively from 4 to 8.
c) The first composition may comprise a cosmetically acceptable salt at a concentration ranging from 0 to 1.5 mol/L, preferably from 0.05 to 1 mol/L, more preferably from 0.2 to 0.5 mol/L.
d) The second composition may comprise a cosmetically acceptable salt at a concentration ranging from 0 to 1.5 mol/L, preferably from 0.05 to 1 mol/L, more preferably from 0.2 to 0.5 mol/L.

e) The first and/or second compositions may comprise pH modifiers and/or buffering agents selected from the group consisting of ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

f) The first and/or second compositions may comprise thickeners (i.e. rheology modifiers) selected from the group consisting of associative polymers, polysaccharides, non-associative polycarboxylic polymers, and mixtures thereof.

g) The first and/or second compositions may comprise surfactants selected from the group consisting of anionic surfactants, nonionic surfactants, amphoteric surfactants, cationic surfactants, and mixtures thereof.

h) The first and/or second compositions may comprise conditioning agents selected from the group consisting of silicones, aminosilicones, fatty alcohols, polymeric resins, polyol carboxylic acid esters, cationic polymers, cationic surfactants, oil derived materials, insoluble oils such as mineral oils, other oils such as glycerin and sorbitol, and mixtures thereof.

i) The first and/or the second compositions of the present invention may further have an ionic strength as defined herein of less than about 1.35 mole/kg, alternatively from about 0.10 to about 0.75 mole/kg, alternatively from about 0.20 to about 0.60 mole/kg.

The following items also form part of the description:

1. A method for colouring hair comprising:
   a) carrying out the following sequence of steps:
      (i) applying a first composition comprising at least one cationic polymer to a first portion of the hair; and
      (ii) applying a second composition comprising at least one anionic polymer to a second portion of the hair; the first and the second portions of the hair having at least one common area;
   and optionally
   b) repeating step a) at least once, wherein the common area of each of the repeated steps a) has at least one common area with:
      the common area of step a); and
      the common area of each of the other repeated steps a) in case step a) is repeated more than once;
   wherein in step a) and/or in at least one of the repeated steps a), the cationic polymer is a coloured cationic polymer.

2. The method according to item 1, wherein in step a) and/or in each of the repeated steps a), the cationic polymer is a coloured cationic polymer.

3. The method according to any of the preceding items, wherein steps i) and/or ii) further comprise the subsequent sub-steps of:
   removing the excess of respectively the first composition and/or the second composition from the hair; and/or
   applying energy to the hair in the form of heat, ultrasounds, infrared and/or microwaves; and/or
   washing and/or rinsing the hair, preferably with a liquid selected from the group consisting of a cosmetically acceptable solvent, a solution comprising a cosmetically acceptable solvent and a cosmetically acceptable salt, a shampoo composition and mixtures thereof, more preferably with water.

4. The method according to any of the preceding items, wherein the cationic polymer comprises at least one monomer unit comprising at least one amino functional group, preferably wherein the amino functional group is selected from the group consisting of primary, secondary, tertiary, quaternary amino functional groups and mixtures thereof, more preferably wherein the amino functional group is selected from the group consisting of primary, secondary amino functional groups and mixtures thereof, even more preferably wherein the amino functional group is selected from secondary amino functional groups.

5. The method according to any of the preceding items, wherein the cationic polymer is selected from the group consisting of linear polyethyleneimine, branched polyethyleneimine, polyallylamine hydrochloride, polydiallyldimethylammonium chloride, copolymers thereof and mixtures thereof.

6. The method according to any of the preceding items, wherein the coloured cationic polymer comprises the same type of chromophore and/or fluorophore or different types of chromophores and/or fluorophores.

7. The method according to any of the preceding items, wherein the anionic polymer comprises at least one monomer unit comprising at least one functional group selected from the group consisting of sulfate, sulfonate, carboxylate, phosphate, phosphonate groups and mixtures thereof, preferably from the group consisting of sulfate, sulfonate, carboxylate groups and mixtures thereof.

8. The method according to any of the preceding items, wherein the anionic polymer is selected from the group consisting of polystyrene sulfonate salts, λ-Carrageenan, Dextran sulfate salts, polyacrylic acid, poly(methacrylic acid) salts, alginic acid salts, carboxymethylcellulose salts, copolymers thereof and mixtures thereof.

9. The method according to any of the preceding items, wherein the anionic polymer is selected from the group consisting of coloured anionic polymers, anionic uncoloured polymers and mixtures thereof.

10. The method according to any of the preceding items, wherein the anionic polymer is an coloured anionic polymer comprising the same type of chromophore and/or fluorophore or different types of chromophores and/or fluorophores.

11. The method according to any of the preceding items, wherein the cationic polymer and/or the anionic polymer comprise one or more compounds selected from the group consisting of cosmetically active molecules, care ingredients, optically active molecules, pharmaceutical active molecules, biomarkers and mixtures thereof.

12. The method according to any of the preceding items, wherein:
   the cationic polymer has a charge density at full protonation of at least 0.3, preferably at least 0.6, more preferably at least 0.8, even more preferably at least 1.0 positive charges per monomer unit and/or
   the anionic polymer has a charge density at full deprotonation of at least 0.3, preferably at least 0.6, more preferably at least 0.8, even more preferably at least 1.0 negative charges per monomer unit.

13. The method according to any of the preceding items, wherein:
   the cationic polymer has a weight average molecular weight of more than 0.5 kDa, preferably from 0.5 to 5000 kDa, preferably from 2 to 1000 kDa, more preferably from 10 to 500 kDa, even more preferably from 25 to 70 kDa and/or the anionic polymer has a weight average molecular weight of at least 1 kDa, preferably from 10 kDa to 1000 kDa, more preferably from 70 to 500 kDa.

14. The method according to any of the preceding items, wherein:

the first composition comprises a total concentration of cationic polymers ranging from 0.1 g/L to 100 g/L, preferably from 0.5 g/L to 100 g/L, more preferably from 2 g/L to 50 g/L, even more preferably from 5 g/L to 10 g/L and/or the second compositions comprise a total concentration of anionic polymers ranging from 0.1 g/L to 100 g/L, preferably from 0.5 g/L to 100 g/L, more preferably from 2 g/L to 50 g/L, even more preferably from 5 g/L to 10 g/L.

15. The method according to any of the preceding items, wherein the first and/or second compositions have a pH ranging from 2 to 14, preferably from 3 to 11, more preferably from 5 to 10, even more preferably from 7 to 9.

16. The method according to any of the preceding items, wherein the first and/or the second compositions comprise a cosmetically acceptable salt at a concentration ranging from 0 to 1.5 mol/L, preferably from 0.05 to 1 mol/L, more preferably from 0.2 to 0.5 mol/L.

17. The method according to any of the preceding items, wherein prior to step a), the hair is pretreated to modify the number of positive or negative charges in some portions of the hair or all over the hair, preferably by chemical or physical means such as pH change, oxidation, reduction, bleaching, plasma treatment, ozone treatment, electrowetting, dry or wet ion-treatment.

18. A hair colouration obtainable by the method according to any of the preceding items.

19. A kit for colouring hair comprising a first compartment comprising the first composition as defined in any of items 1 to 17 and a second compartment comprising the second composition as defined in any of items 1 to 17.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the following section the solvent used to prepare the different compositions is water, unless otherwise specified.

I. Synthesis Methods for Obtaining the Different Cationic or Coloured Anionic Polymers Used in the Examples Coloured Cationic Polymers Polyallylamine hydrochloride labeled with Rhodamine B isothiocyanate (PAH-RhoB_iso):
Starting materials:
Polyallylamine hydrochloride (PAH), Mw=56,000 Da (CAS: 71550-12-4) available from Sigma-Aldrich
Rhodamine-B isothiocyanate (RhoB_iso) (CAS: 36877-69-7) available from Sigma-Aldrich Synthesis method:
The following method has been used for labeling Polyallylamine hydrochloride (PAH) with Rhodamine B isothiocyanate (RhoB_iso):
Dissolving 60 mg of Polyallylamine hydrochloride (PAH) in 10 mL of carbonate buffer (pH 9);
Mixing the dissolved polymer with 1 mg of Rhodamine-B isothiocyanate (RhoB_iso) dissolved in 1 mL of DMSO;
Stirring for 24 h at 4° C. and dialyzing against distilled water the resultant mixture.

Branched polyethyleneimine labeled with Rhodamine B (PEI-RhoB_iso):
Starting materials:
Branched polyethyleneimine (PEI), LUPASOL G 500, Mw=25,000 Da (CAS: 9002-98-6) available from BASF
Rhodamine-B isothiocyanate (RhoB_iso) (CAS: 36877-69-7) available from Sigma-Aldrich Synthesis method:
The same method as for labeling Polyallylamine hydrochloride with Rhodamine B isothiocyanate has been used, wherein PAH was replaced by PEI.

Branched polyethyleneimine labeled with Reactive Red 180 (PEI-Red with a labelling degree of 7.8):
Starting materials:
Branched polyethyleneimine (PEI) (LUPASOL G 500), Mw=25,000 Da, available from BASF (CAS: 9002-98-6)
Reactive Red 180 available from S3 Chemicals (CAS: 72828-03-6).

Synthesis method:
The following method has been used for labeling Branched polyethyleneimine (PEI) with Reactive Red 180 (Red):
1) Dissolving 12.5 g of a 40 wt % solution of Branched polyethyleneimine (PEI) in a 200 ml methanol solution containing 14.05 g of Reactive Red 180;
2) Stirring the suspension at 60° C. for 1 hour;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colourless;
7) Mixing all the resulting supernatant solutions from steps 4) to 6);
8) Adding 12.5 ml of a 32 wt % hydrochloric acid solution to the resulting mixture from step 7)
9) Centrifuging the resulting suspension and collecting the precipitate;
10) Washing the precipitate with acetone until the supernatant is colourless;
11) Drying the precipitate and dissolving it in water;
12) Dialyzing the resulting solution against a solution of 0.15 M NaCl and $10^{-4}$ to $10^{-5}$ M HCl
13) Freeze-drying the product Branched polyethyleneimine (PEI) labeled with Remazol brilliant Blue R (PEI-Blue with a labelling degree of 10):
Starting materials:
Branched polyethyleneimine (PEI), LUPASOL G 500, Mw=25,000 Da (CAS: 9002-98-6) available from BASF
Remazol brilliant Blue R available from Sigma-Aldrich (CAS: 2580-78-1)

Synthesis method:
The same method as for labeling Branched polyethyleneimine with Reactive Red 180 has been used wherein Reactive Red 180 was replaced by Remazol brilliant Blue R and wherein in step 1) 12.5 g of a 40 wt % Branched polyethyleneimine (PEI) solution were dissolved in a 200 ml methanol solution containing 7.3 g of Remazol brilliant Blue R.

Branched polyethyleneimine labeled with Reactive Blue 116 (PEI-Cyan with a labelling degree of 10):
Starting materials:
Branched polyethyleneimine (PEI), LUPASOL G 500, Mw=25,000 Da (CAS: 9002-98-6), available from BASF
Reactive Blue 116 (CAS: 61969-03-7) available from mijn-eigen.nl.
Synthesis method:
The same method as for labeling Branched polyethyleneimine with Reactive Red 180 has been used wherein Reactive Red 180 was replaced by Reactive Blue 116 and wherein in step 1) 12.5 g of a 40 wt % Branched polyethyleneimine (PEI) solution were dissolved in a 200 ml methanol solution containing 11.1 g of Reactive Blue 116.

Polydiallyldimethylammonium chloride copolymerized with Methacryloxyethyl thiocarbamoyl rhodamine B (PDADMAC-RhoB with a labelling degree of 206):
Starting materials:
Monomeric diallyldimethylammonium chloride (CAS. 7398-69-8) available from Sigma-Aldrich
Methacryloxyethyl thiocarbamoyl rhodamine B (RhoB), available from Polysciences
Synthesis method:
1.61 g monomeric diallyldimethylammonium chloride and 33 mg methacryloxyethyl thiocarbamoyl rhodamine B were copolymerized in 20 mL 50% methanol at 80° C. under nitrogen atmosphere for 24 hours using 10 mg potassium peroxodisulfate as initiator. After polymerization, the coloured polymer was dialyzed against distilled water.

Coloured Anionic Polymers
Polystyrene sulfonate copolymerized with Rhodamine B isothiocyanate (PSS-RhoB with a labelling degree of 206):
Starting materials:
Monomeric Sodium 4-vinylbenzenesulfonate (CAS: 2695-37-6) available from Sigma-Aldrich.
Methacryloxyethyl thiocarbamoyl rhodamine B (RhoB), available from Polysciences
Synthesis method:
The same method as for copolymerizing Polydiallyldimethylammonium chloride with Methacryloxyethyl thiocarbamoyl rhodamine B has been used wherein 1.61 g monomeric diallyldimethylammonium chloride has been replaced by 2.05 g monomeric Sodium 4-vinylbenzenesulfonate.

Cationic Uncoloured Polymer Used in the Following Examples
Branched polyethyleneimine (PEI), LUPASOL G 500, Mw=25,000 Da (CAS: 9002-98-6) available from BASF Anionic Uncoloured Polymers Used in the Following Examples
Poly(methacrylic acid) sodium salt (PMAA), Mw=15,000 Da (CAS: 25087-26-7) available from Polysciences, Inc.
Polystyrene sulfonate sodium salt (PSS), Mw=70,000 Da (CAS: 25704-18-1) available from Sigma-Aldrich.
Lambda-Carrageenan (CAS: 9064-57-7) available from Fluka
Dextran sulfate sodium salt, Mw=500,000 Da (CAS: 9011-18-1) available from Fluka.
Sodium alginate (CAS: 9005-38-3) available from Fagron.

The hair swatches which have been used in the following sets of experimental data are natural hair blond hair swatches available from Kerling International Haarfabrik GmbH, Backnang, Germany with the reference number 826533.

II. First Set of Experimental Data—Examples of Methods According to the Present Invention Wherein Different Types of Anionic Polymers have been Used Example 1A

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been halved vertically and coloured according to the following protocol:
(i) Preparing the first and second compositions shortly before application;
(ii) Dipping the hair swatch into 5 mL of the first composition at 55° C. in a test tube;
(iii) Agitating the first composition with the hair swatch for 15 min at 55° C. in a laboratory-type drying cabinet;
(iv) Rinsing the hair swatch for 30 s with running lukewarm tap water at a temperature of 30° C. to 35° C.;
(v) Dipping the hair swatch into 5 mL of the second composition at 55° C. in a test tube;
(vi) Agitating the second composition with the hair swatch for 15 min at 55° C. in a laboratory-type drying cabinet;
(vii) Rinsing the hair swatch for 30 s with running lukewarm tap water at a temperature of 30° C. to 35° C.;
(viii) Repeating steps (ii) to (vii) a second time.
(ix) Drying the hair swatch first with tissue paper and then with a hair dryer.

Example 1B

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |

-continued

| Ingredients | g/l |
|---|---|
| pH adjusted to 8 by adding 1.0 mol/l NaOH or 1.0 mol/l HCl | |
| Second Composition | |
| Lambda-Carrageenan | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured using the same protocol as for Example 1A.

Example 1C

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| Sodium Alginate | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured using the same protocol as for Example 1A.

Example 1D

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to: 8 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured using the same protocol as for Example 1A.

Conclusion:

Examples 1A to 1D demonstrates that a high diversity of anionic polymer may be used in the system and method according to the present invention.

III. Second Set of Experimental Data—Comparison Between the Method According to the Present Invention and a Method for Colouring Hair Using Direct Dyes Example 2A

| Ingredients | g/l |
|---|---|
| First Composition | |
| PAH-RhoB_iso | 1.00 (0.1 wt %) |
| NaCl | 11.69 (0.2 mol/L) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PSS | 1.00 (0.1 wt %) |
| NaCl | 11.69 (0.2 mol/L) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured according to the following protocol:
(i) Preparing the first and second compositions shortly before application;
(ii) Dipping the hair swatch into 10 mL of the first composition at 40° C. in a test tube;
(iii) Agitating the first composition with the hair swatch for 30 min at 40° C. in a laboratory-type drying cabinet;
(iv) Rinsing the hair swatch three times with fresh 10 ml lukewarm tap water at a temperature of 30° C. to 35° C. in a test tube while stirring for 5 min;
(v) Dipping the hair swatch into 10 mL of the second composition at 40° C. in a test tube;
(vi) Agitating the second composition with the hair swatch for 30 min at 400 laboratory-type drying cabinet;
(vii) Rinsing the hair swatch three times with fresh 10 ml lukewarm tap water at a temperature of 30° C. to 35° C. in a test tube while stirring for 5 min;
(viii) Repeating steps (ii) to (vii) a second time.
(ix) Drying the hair swatch first with tissue paper and then with a hair dryer Example 2B

| Ingredients | g/l |
|---|---|
| First Composition | |
| PDADMAC-RhoB | 1.00 (0.1 wt %) |
| NaCl | 11.69 (0.2 mol/L) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 2A.

Example 2C

| Ingredients | g/l |
|---|---|
| First Composition | |
| PEI-RhoB_iso | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 2A.

Example 2D

| Ingredients | g/l |
|---|---|
| First Composition | |
| PAH-RhoB_iso | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PMAA | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 2A.

Example 2E

| Ingredients | g/l |
|---|---|
| First Composition | |
| PDADMAC-RhoB | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PMAA | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 2A.

Comparative Example 1

| Direct Dye composition | |
|---|---|
| Ingredients | g/l |
| Rhodamine B[1] | 0.25 (0.025 wt %) | pH: 7
[1]Rhodamine B (CAS: 81-88-9) available from Fluka

A hair swatch has been coloured according to the following experimental protocol:
  (i) Preparing the direct dye composition;
  (ii) Dipping the hair swatch into 10 mL of the direct dye composition at 40° C. in a test tube;
  (iii) Agitating the direct dye composition with the hair swatch for 30 min at 40° C. in a laboratory-type drying cabinet;
  (iv) Rinsing the hair swatch three times with fresh 10 ml lukewarm tap water at a temperature of 30° C. to 35° C. in a test tube while stirring for 5 min;
  (v) Repeating steps (ii) to (iv) a second time;
  (vi) Drying the hair swatch first with tissue paper and then with a hair dryer.

Washing with Shampoo:

Each of the coloured hair swatches which have been obtained in examples 2A to 2E and in comparative example 1 were washed 5 times with a neutral shampoo using the following procedure:
  (i) Wetting the hair swatch with running tap water for 10 s;
  (ii) Adding 2-3 drops of a shampoo to the hair swatch;
  (iii) Rubbing the hair swatch with fingers for 30 s;
  (iv) Rinsing the hair swatch with running tap water at a temperature of 30° C. to 35° C.;
  (v) Repeating steps (ii) to (iv) four more times
  (vi) Drying the hair swatch first with tissue paper and then with a hair dryer.

Colour Intensity:

Measurement

The colour intensity of the coloured hair swatches obtained in example 2A to 2E has been compared visually with the colour intensity of the coloured hair swatch obtained in comparative example 1.

Result and Conclusion

The colour intensity of the coloured hair swatches obtained in examples 2A to 2E was higher than the colour intensity of the coloured hair swatch of comparative example 1. Hence, colouring the hair using the system according to the present invention provides a better colour intensity than colouring the hair with a direct dye composition.

Washfastness:

Measurement

The washfastness of each of the coloured hair swatches obtained in examples 2A to 2E and in comparative example 1 has been evaluated visually comparing the colour intensity of the hair swatch before and after washing the hair swatch with shampoo according to the above procedure.

Result and Conclusion

The coloured hair swatches obtained in examples 2A to 2E have a better washfastness than the coloured hair swatch obtained in comparative example 1.

IV. Third Set of Experimental Data—Influence of the pH of the First and Second Compositions which are Used in the Method According to the Present Invention on the Colour Intensity of the Hair Colouration Example 3A

| Ingredients | g/l |
|---|---|
| First Composition | |
| PEI-Blue | 2.00 (0.2 wt %) |
| NaCl | 11.69 (0.2 mol/l) |
| Sodium acetate | 3.71 |
| Acetic acid | 0.85 |
| pH adjusted to 5 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been halved vertically and coloured according to the following protocol:
(i) Preparing the first and second compositions shortly before application;
(ii) Dipping the hair swatch into 5 mL of the first composition at 45° C. in a test tube;
(iii) Agitating the first composition with the hair swatch for 20 min at 45° C. in a laboratory-type drying cabinet;
(iv) Rinsing the hair swatch for 30 s with running lukewarm tap water at a temperature of 30° C. to 35° C.;
(v) Dipping the hair swatch into 5 mL of the second composition at 45° C. in a test tube;
(vi) Agitating the second composition with the hair swatch for 20 min at 45° C. in a laboratory-type drying cabinet;
(vii) Rinsing the hair swatch for 30 s with running lukewarm tap water at a temperature of 30° C. to 35° C.;
(viii) Repeating steps (ii) to (vii) a second time.
(ix) Drying the hair swatch first with tissue paper and then with a hair dryer Example 3B

| Ingredients | g/l |
|---|---|
| First Composition | |
| PEI-Blue | 2.00 (0.2 wt %) |
| NaCl | 11.69 (0.2 mol/l) |
| Sodium acetate | 3.71 |
| Acetic acid | 0.85 |
| pH adjusted to 6 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 3A.

Example 3C

| Ingredients | g/l |
|---|---|
| First Composition | |
| PEI-Blue | 2.00 (0.2 wt %) |
| NaCl | 11.69 (0.2 mol/l) |
| HEPES(4-(2-hydroxyethyl)-1-piperazineethanesulfonic acid) | 11.92 (0.05 mol/l) |
| pH adjusted to 7 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental protocol as in Example 3A.

Example 3D

| Ingredients | g/l |
|---|---|
| First Composition | |
| PEI-Blue | 2.00 (0.2 wt %) |
| NaCl | 11.69 (0.2 mol/l) |
| HEPES(4-(2-hydroxyethyl)-1-piperazineethanesulfonic acid) | 11.92 (0.05 mol/l) |
| pH adjusted to 8 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured following the same experimental protocol as in Example 3A.

Example 3E

| Ingredients | g/l |
|---|---|
| First Composition | |
| PEI-Blue | 2.00 (0.2 wt %) |
| NaCl | 11.69 (0.2 mol/l) |
| Ethanolamine | 3.05 (0.05 mol/l) |
| pH adjusted to: 9 by adding 1.0 mol/l NaOH or 1.0 mol/l HCl | |

-continued

| Ingredients | g/l |
| --- | --- |
| Second Composition | |
| Ingredients | g/l |
| PSS | 2.00 (0.2 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured following the same experimental protocol as in Example 3A.

Colour Intensity:

Measurement

The colour intensity of each of the coloured hair swatches obtained in example 3A to 3E has been compared visually.

Result and Conclusion

The colour intensity increases proportionally to the pH of the first composition. Nevertheless, one of the advantages of the system according to the present invention is that the hair may be coloured with a good colour intensity even if the compositions which are used have a lower pH than standard oxidative hair colouring compositions. Using compositions with a lower pH than standard oxidative hair colouring compositions may reduce the risk of damaging the hair.

V. Fourth Set of Experimental Data—Influence of the Number of Sequences of Steps and of the Type of Outermost Layer on Colour Intensity and Washfastness of the Hair Colouration In the following set of data, the following first and second compositions have been used. The first and second compositions have been prepared shortly before application.

| Ingredients | g/l |
| --- | --- |
| First Composition | |
| PEI-Red | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

Examples 4A to 4G

In each of the following examples, the first and the second compositions have been applied to a hair swatch according to different sequences, alternating the application of the first composition with the application of the second composition. The first and the second compositions have been prepared shortly before application.

The first composition has been applied to the hair according to the following protocol:
(i) Dipping the hair swatch into 5 mL of the first composition at 55° C. in a test tube;
(ii) Agitating the first composition with the hair swatch for 15 min at 55° C. in a laboratory-type drying cabinet;
(iii) Rinsing the hair swatch with lukewarm tap water at a temperature of 30° C. to 35° C.

The second composition has been applied to the hair according to the following protocol:
(i) Dipping the hair swatch into 5 mL of the second composition at 55° C. in a test tube;
(ii) Agitating the second composition with the hair swatch for 15 min at 55° C. in a laboratory-type drying cabinet;
(iii) Rinsing the hair swatch with lukewarm tap water at a temperature of 30° C. to 35° C.

At the end of each of the sequence of application of the first and the second compositions to the hair, the hair swatch has been dried first with tissue paper and then with a hair dryer Sequences of Application of the First and the Second Compositions to the Hair:

| Example | Sequence |
| --- | --- |
| Example 4A | PEI-Red/PSS |
| Example 4B | PEI-Red/PSS/PEI-Red |
| Example 4C | (PEI-Red/PSS)2 |
| Example 4D | (PEI-Red/PSS)2/PEI-Red |
| Example 4E | (PEI-Red/PSS)3 |
| Example 4F | (PEI-Red/PSS)3/PEI-Red |
| Example 4G | (PEI-Red/PSS)4 |

Comparative Example 2

A hair swatch has been coloured according to the following protocol:
(i) Dipping the hair swatch into 5 mL of the first composition at 55° C. in a test tube;
(ii) Agitating the first composition with the hair swatch for 15 min at 55° C. in a laboratory-type drying cabinet;
(iii) Rinsing the hair swatch with lukewarm tap water at a temperature of 30° C. to 35° C.

Washing with Shampoo:

Each of the coloured hair swatches which have been obtained in examples 4A to 4G and in comparative example 2 were washed 3 times with Wella Brillance Shampoo available in Germany in August 2014 using the following procedure:
(i) Wetting the hair swatch with running tap water for 10 s;
(ii) Adding 2-3 drops of a shampoo to the hair swatch;
(iii) Rubbing the hair swatch with fingers for 30 s;
(iv) Rinsing the hair swatch with running tap water at a temperature of 30° C. to 35° C.;
(v) Repeating steps (ii) to (iv) two more times;
(vi) Drying the hair swatch first with tissue paper and then with a hair dryer.

$L^*$, $a^*$, $b^*$ Measurements

The colorimetric parameters in the CIE $L^*$ $a^*$ $b^*$ system are measured for each of the hair swatches obtained in Example 4A to 4G and in comparative example 2 before and after washing using a Minolta CM-508i spectrophotometer (illuminant is D65 daylight with 100 observer) in which $L^*$ represents the lightness of the colour, $a^*$ indicates the green/red colour axis and $b^*$ the blue/yellow colour axis. Overall colour change is represented by $\Delta E$ where $\Delta E$ is defined by the following formula:

$$\Delta E = [(\Delta L^*)^2 + (\Delta a^*)^2 + (\Delta b^*)^2]^{1/2}$$

Results and Conclusion:

| Example | Type of layers | Before washing | | | After three times washing with shampoo | | | ΔE |
|---|---|---|---|---|---|---|---|---|
| | | L* | a* | b* | L* | a* | b* | |
| Comparative Example 2 | PEI-Red | −19.31 | 30.94 | −7.62 | −13.90 | 27.50 | −8.46 | 6.47 |
| Example 4A | PEI-Red/PSS | −18.62 | 30.75 | −8.51 | −15.65 | 27.93 | −8.09 | 4.12 |
| Example 4B | PEI-Red/PSS/ PEI-Red | −23.71 | 30.29 | −7.33 | −19.46 | 30.23 | −8.62 | 4.44 |
| Example 4C | (PEI-Red/PSS)2 | −24.93 | 32.32 | −7.03 | −22.37 | 30.74 | −7.88 | 3.13 |
| Example 4D | (PEI-Red/PSS)2/ PEI-Red | −27.21 | 26.43 | −6.09 | −25.08 | 27.35 | −6.90 | 2.46 |
| Example 4E | (PEI-Red/PSS)3 | −27.87 | 28.24 | −6.62 | −26.03 | 27.74 | −7.00 | 1.94 |
| Example 4F | (PEI-Red/PSS)3/ PEI-Red | −28.66 | 24.86 | −6.00 | −26.73 | 24.88 | −6.79 | 2.09 |
| Example 4G | (PEI-Red/PSS)4 | −29.34 | 25.08 | −6.72 | −27.35 | 24.04 | −6.96 | 2.26 |

When comparing the L* values measured for examples 4A, 4C, 4E and 4G before washing, it can be noticed that the colour intensity of hair coloured with the first and second compositions according to the present invention increases with increased number of times the sequence of steps of the method according to the present invention is repeated.

When comparing the ΔE values measured for examples 4A, 4C and 4E, it can be noticed that the ΔE value decreases with increased number of times the sequence of steps of the method according to the present invention is repeated.

When comparing the ΔE values obtained for example 4A vs. comparative example 2 or for example 4C vs. example 4B or for example 4E vs. example 4D, the ΔE value is usually lower when the last layer which is positioned on top of the hair is made of an anionic polymer, i.e. the hair colouration obtained on hair is characterized by a better washfastness. This demonstrates that the anionic layer may act as a protective layer for the coloured cationic layer which is placed underneath.

VI. Fifth Set of Experimental Data—Examples of a System According to the Present Invention Wherein a First Composition Comprising a Coloured Cationic Polymer and a Second Composition Comprising a Coloured Anionic Polymer have been Used Example 5

| Ingredients | g/l |
|---|---|
| First Composition | |
| PEI-Cyan | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS-RhoB | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the following protocol:
(i) Preparing the first and second compositions shortly before application;
(ii) Dipping the hair swatch into 5 mL of the first composition at 55° C. in a test tube;
(iii) Agitating the first composition with the hair swatch for 15 min at 55° C. in a laboratory-type drying cabinet;
(iv) Rinsing the hair swatch with lukewarm tap water at a temperature of 30° C. to 35° C.;
(v) Dipping the hair swatch into 5 mL of the second composition at 55° C. in a test tube;
(vi) Agitating the second composition with the hair swatch for 15 min at 55° C. in a laboratory-type drying cabinet;
(vii) Rinsing the hair swatch with lukewarm tap water at a temperature of 30° C. to 35° C.

Comparative Example 3

| Ingredients | g/l |
|---|---|
| First Composition | |
| PEI-Cyan | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the same protocol as for Example 5 using the above first and second compositions.

Comparative Example 4

| Ingredients | g/l |
|---|---|
| First Composition | |
| PEI | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

-continued

| Ingredients | g/l |
|---|---|
| Second Composition | |
| PSS-RhoB | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the same protocol as for Example 5 using the above first and second compositions.

L*, a*, b* Measurements

The colorimetric parameters in the CIE L* a* b* system have been measured for each of the hair swatches obtained in example 5 and in comparative examples 3 and 4 before and after colouring using a Minolta CM-508i spectrophotometer (illuminant is D65 daylight with 10° observer) in which L* represents the lightness of the colour, a* indicates the green/red colour axis and b* the blue/yellow colour axis.

Results and Conclusion:

| | | Before colouring | | | | After colouring | | | |
|---|---|---|---|---|---|---|---|---|---|
| Example | Layers | L* | a* | b* | Colour | L* | a* | b* | Colour |
| Comparative example 3 | PEI-Cyan/PSS | 14.08 | 1.81 | 7.05 | Blond | 2.22 | −13.63 | −1.73 | Cyan |
| Comparative example 4 | PEI/PSS-Rho | 13.42 | 1.74 | 7.28 | Blond | −2.57 | 19.81 | −6.76 | Red |
| Example 5 | PEI-Cyan/PSS-Rho | 12.75 | 1.94 | 7.76 | Blond | −10.37 | 6.47 | −14.71 | Purple |

As can be seen in this set of experimental data, the first composition used in example 5 comprises a coloured cationic polymer and the second composition used in example 5 comprises a coloured anionic polymer. When both coloured first and second composition have been applied onto hair, the resultant colour which was obtained was different from the colour which was obtained when either the first coloured composition or the second coloured composition have been applied onto hair. Therefore, it is possible to combine different cationic and coloured anionic polymers in order to obtain in an easy manner the desired colour result.

VII. Different Dyes Linked to the Same Polymer

Synthesis Methods for Obtaining Cationic Coloured Polymers which May be Used in the Method According to the Present Invention:

I. Branched polyethyleneimine labeled with anionic dyes:
1. Starting materials:
   1) Branched polyethyleneimine (PEI), LUPASOL WF, Mw=25,000 Da available from BASF (CAS: 9002-98-6)
   2) EverPlus Red 4B Powder available from Everlight Chemicals
   3) EverPlus Yellow 6G Powder available from Everlight Chemicals
   4) EverPlus Blue 3R Powder available from Everlight Chemicals
   5) Remazol brilliant Blue R available from Sigma-Aldrich (CAS: 2580-78-1)
   6) Remazol Yellow GR (Reactive Yellow 15) available from Dystar (CAS: 12226-47-0)
   7) Reactive Red 180 available from S3 Chemicals (CAS: 72828-03-6).
2. Synthesis method I (Sample 6A):
   The following method has been used for labeling Branched polyethyleneimine (PEI) with EverPlus Red 4B, Yellow 6G and Blue 3R to label a cationic polymer with three different dyes (chromophores) in a weight ratio 1:1:1 (red:green:blue) in water. The obtained visual result is illustrated in FIG. 1, Sample 6A and produces a brown colouration:
   1) Dissolving 200 mg branched polyethyleneimine (PEI) in a 30 ml aqueous solution containing 92 mg EverPlus Red 4B, 92 mg Yellow 6G and 92 mg Blue 3R
   2) Stirring the suspension at 60° C. for 1 hour;
   3) Further stirring the resultant mixture at room temperature for 12 h;
   4) Centrifuging the resultant mixture and collecting the supernatant;
   5) Evaporate the collected supernatant to dryness;
   6) Adding methanol to dissolve the solid completely;
   7) Adding 0.5 ml of a 32 wt % hydrochloric acid solution to the resulting mixture from step 6)
   8) Centrifuging the resulting suspension and collecting the precipitate;
   9) Washing the precipitate with acetone until the supernatant is colorless;
   10) Drying the precipitate and dissolving it in water;
   11) Dialyzing the resulting solution against a solution of 0.15 M NaCl and $10^{-4}$ to $10^{-5}$ M HCl
   12) Freeze-drying the product
3. Synthesis method II (Sample 6B):
   The following method has been used for labeling Branched polyethyleneimine (PEI) with EverPlus Red 4B, Yellow 6G and Blue 3R to label a cationic polymer with three different dyes (chromophores) in a weight ratio 1:2:2 (red:green:blue) in methanol. The obtained visual result is illustrated in FIG. 1, Sample 6B and produces a green-brown colouration:
   1) Dissolving 200 mg branched polyethyleneimine (PEI) in a 30 ml methanolic solution containing 40 mg EverPlus Red 4B, 80 mg Yellow 6G and 80 mg Blue 3R
   2) Stirring the suspension at 60° C. for 1 hour;
   3) Further stirring the resultant mixture at room temperature for 12 h;
   4) Centrifuging the resultant mixture and collecting the supernatant;
   5) Adding methanol to the precipitate, centrifuging the mixture and collecting the supernatant;
   6) Repeating step 5) until the resulting supernatant is colorless;

7) Mixing all the resulting supernatant solutions from steps 4) to 6);
8) Adding 12.5 ml of a 32 wt % hydrochloric acid solution to the resulting mixture from step 7)
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and $10^{-4}$ to $10^{-5}$ M HCl
13) Freeze-drying the product 4. Synthesis method III (Sample 6C):

The following method has been used for labeling Branched polyethyleneimine (PEI) with EverPlus Red 4B, Yellow 6G and Blue 3R to label a cationic polymer with three different dyes (chromophores) in a weight ratio 1:2:2 (red:green:blue) in water. The obtained visual result is illustrated in FIG. 1, Sample 6C and produces a green-brown colouration:
1) Dissolving 200 mg branched polyethyleneimine (PEI) in a 30 ml aqueous solution containing 40 mg EverPlus Red 4B, 80 mg Yellow 6G and 80 mg Blue 3R;
2) Stirring the suspension at 60° C. for 1 hour;
3) Further stirring the resultant mixture at room temperature for 12 h;
4) Centrifuging the resultant mixture and collecting the supernatant;
5) Evaporate the collected supernatant to dryness;
6) Adding methanol to dissolve the solid completely;
7) Adding 0.5 ml of a 32 wt % hydrochloric acid solution to the resulting mixture from step 6)
8) Centrifuging the resulting suspension and collecting the precipitate;
9) Washing the precipitate with acetone until the supernatant is colorless;
10) Drying the precipitate and dissolving it in water;
11) Dialyzing the resulting solution against a solution of 0.15 M NaCl and $10^{-4}$ to $10^{-5}$ M HCl
12) Freeze-drying the product 5. Synthesis method IV (Samples 7A to 7E)

Figure 2:
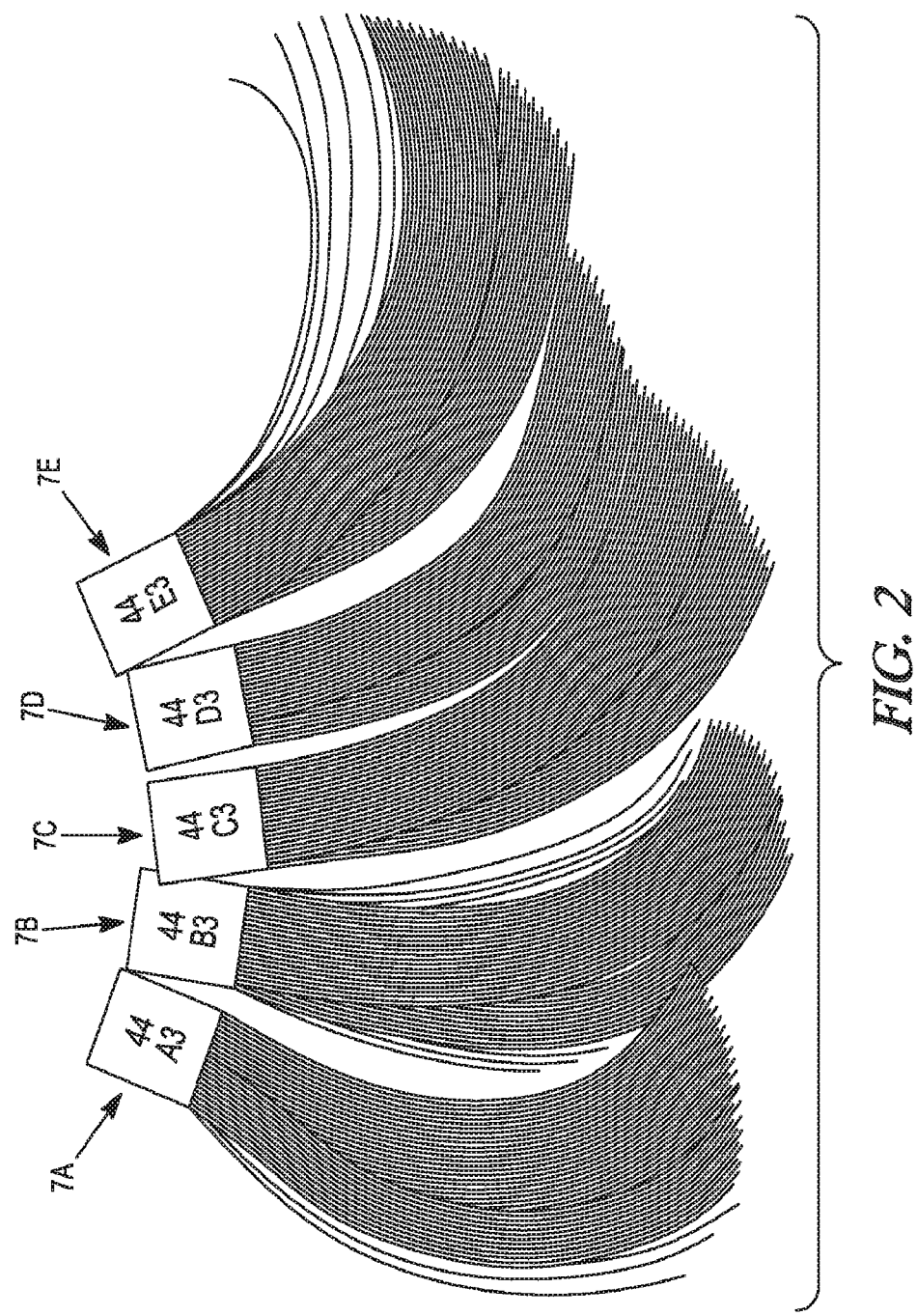
FIG. 2 illustrates samples prepared according to an embodiment of the invention, wherein different chromophores were linked to the same polymer backbone.

The following method has been used for labeling Branched polyethyleneimine (PEI) with Reactive Red 180, Remazol Yellow 6G and Blue 3R:
1) Dissolving 100 mg branched polyethyleneimine (PEI) in a 5 ml methanolic solution containing respective amounts of Reactive Red 180 and/or Remazol Yellow 6G and/or Blue 3R as defined in table 1.
2) Stirring the suspension at 60° C. for 1 hour;
3) Centrifuging the resultant mixture and collecting the supernatant;
4) Adding methanol to the precipitate, centrifuging the mixture and collecting the supernatant;
5) Repeating step 5) until the resulting supernatant is colorless;
6) Mixing all the resulting supernatant solutions from steps 4) to 6);
7) Adding 232 μl ml of a 32 wt % hydrochloric acid solution to the resulting mixture from step 6)
8) Centrifuging the resulting suspension and collecting the precipitate;
9) Washing the precipitate with methanol until the supernatant is colorless;
10) Washing the precipitate with diethyl ether until the supernatant is colorless;
11) Stirring the precipitate with diethyl ether until for 1 h to obtain a fine powder;
12) Filtrate the precipitate to remove diethyl ether
13) Drying the precipitate and dissolving it in water;
14) Dialyzing the resulting solution against a solution of 0.15 M NaCl and $10^{-4}$ to $10^{-5}$ M HCl
15) Freeze-drying the product The following table 1 gives a summary of the respective amounts of Reactive Red 180, Remazol Yellow 6G Blue 3R used to synthesize a cationic polymer with different dyes (chromophores). As it is shown in FIG. 2, a variety of different colours, shades and tones can be obtained by linking different dyes to the same polymer.

TABLE 1

| Sample nr. | [mg] Reactive Red | [mg] Remazol yellow | [mg] Remazol blue | Color |
|---|---|---|---|---|
| 7A |  | 46 | 149 |  | Orange |
| 7B | 139 |  | 117 | Purple |
| 7C |  | 93 | 146 | Green |
| 7D | 77 | 62 | 97 | Brown |
| 7E | 185 | 37 |  | Red |

II. Procedure for colouring hair with the above prepared coloured cationic polymers of samples 6A to 6C and 7A to 7E.

The first and second compositions used for colouring the hair are listed below. "PEI-shade" means the respective coloured PEI used, for example the PEI with the different dyes of any of the samples 6A to 6C and 7A to 7E.

| Ingredients | g/l |
|---|---|
| First Composition | |
| PEI-Shade | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |

A hair swatch has been coloured according to the following protocol:
(i) Preparing the first and second compositions shortly before application;
(ii) Place hair swatch on plastic wrap or color wraps
(iii) Work 5 mL of the first composition into the hair tress using a brush
(iv) Agitating the first composition with the hair swatch for 15 min at 45° C. in a laboratory-type drying cabinet;
(v) Rinsing the hair swatch for 30 s with running lukewarm tap water at a temperature of 30° C. to 35° C.;
(vi) Place hair swatch on plastic wrap or color wraps (vii) Work 5 mL of the second composition into the hair tress using a brush
(viii) Rinsing the hair swatch for 30 s with running lukewarm tap water at a temperature of 30° C. to 35° C.;
(ix) Repeating steps (ii) to (vii) a second time.
(x) Drying the hair swatch first with tissue paper and then with a hair dryer.

When adjusting the pH of the first composition to be 10, the colouration becomes more intense showing that that the intensity of the colouration can be tailored by varying the pH of the composition which contains the coloured polymers.

Using the above approach of linking different dyes (chromophores and/or fluorphores) to the same polymer ensures that the colouration tone can be well defined and controlled by the manufactured. The colouration thus does not vary from application to application.

While the above experiments has been made with two or three different dyes, the invention is not limited thereto and can be carried out with 4, 5, 6 or even more different dyes linked to the same polymer.

VIII. Different Dyes Linked to Separate Polymers of the Same Polymeric Layer (Mixing Different Coloured Cationic Polymers in the Same Polymeric Layer)

I. Samples 8A to 8F, mixing of PEI-Everlight Red 4B and PEI-Everlight Blue 3R

According to an embodiment, differently coloured cationic polymers are mixed in the same composition to obtain a shading of the colouration. A first dye has been linked with a first polymer and a second dye linked to a second polymer. The differently coloured polymers are mixed with a selected ratio in the first composition. The first and second (uncoloured) polymers may be the same or may be different.

The first and second compositions used in the experiments have been prepared as shown below. The weight mixing ratio in the following table is 1:1 (PEI-Everlight Red 4B: PEI-Everlight Blue 3R), which corresponds to sample 8A. Sample 8B has a mixing ratio 1:3, sample 8C has a mixing ratio of 1:9, sample 8D has a mixing ratio of 3:1, and sample 8E has a mixing ratio of 9:1.

Sample 8F is a not coloured reference sample.

| Ingredients | g/l |
|---|---|
| First Composition | |
| PEI-Everlight Red 4B | 2.50 (0.25 wt %) |
| PEI-Everlight Blue 3R | 2.50 (0.25 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |

A hair swatch has been coloured according to the following protocol:
(i) Preparing the first and second compositions shortly before application;
(ii) Place hair swatch on plastic wrap or color wraps
(iii) Work 5 mL of the first composition into the hair tress using a brush
(iv) Agitating the first composition with the hair swatch for 15 min at 45° C. in a laboratory-type drying cabinet;
(v) Rinsing the hair swatch for 30 s with running lukewarm tap water at a temperature of 30° C. to 35° C.;
(vi) Place hair swatch on plastic wrap or color wraps
(vii) Work 5 mL of the second composition into the hair tress using a brush
(viii) Rinsing the hair swatch for 30 s with running lukewarm tap water at a temperature of 30° C. to 35° C.;
(ix) Repeating steps (ii) to (vii) a second time.
(x) Drying the hair swatch first with tissue paper and then with a hair dryer.

Figure 3:
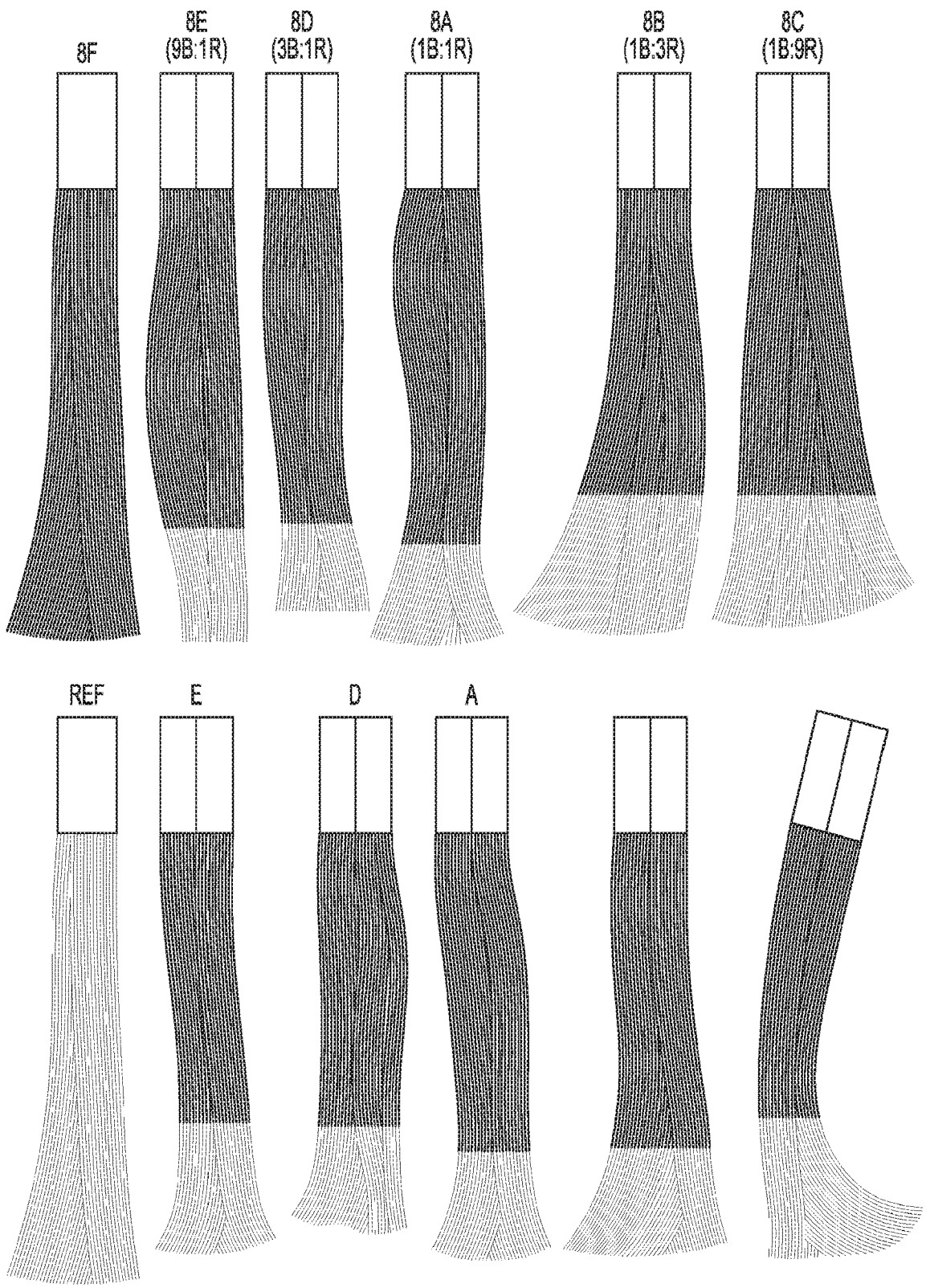
FIG. 3 illustrates samples prepared according to an embodiment of the invention, wherein a mixture of polymers each linked with a different chromophore was applied to hair.

The upper row in FIG. 3 shows the colouration results on medium blond hair, whereas the lower row shows the colouration results on white blond hair.

The samples illustrated in FIG. 3 shows that different colours and shades can be obtained when mixing polymers that a differently coloured. While the above samples uses only two differently coloured polymers, the number is not restricted thereto and virtually any number of differently coloured polymers, for example, three, four, five or oven more can be used.

II. Samples 9A to 9I, mixing of PEI-Reactive Red 180 and PEI-Remazol Yellow

Figure 4:
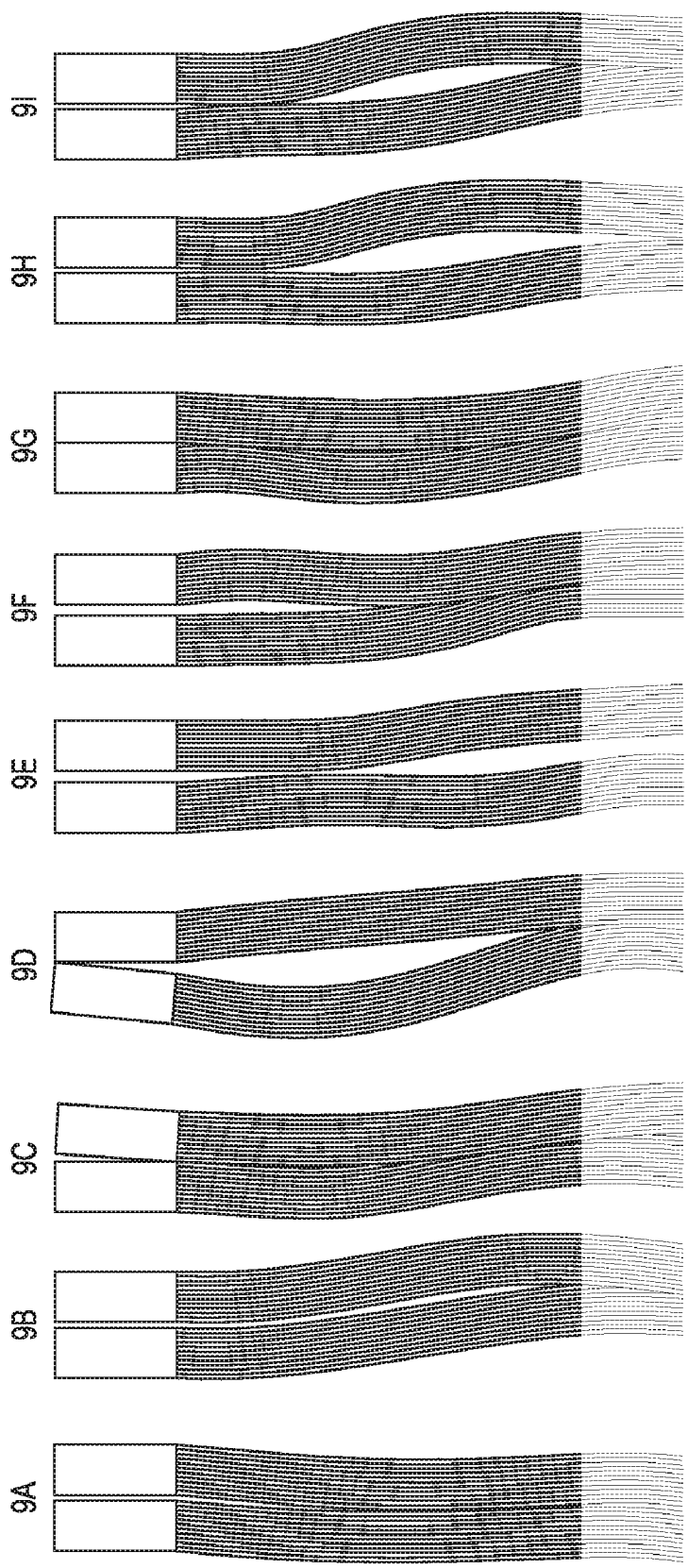
FIG. 4 illustrates samples prepared according to an embodiment of the invention, wherein a mixture of polymers each linked with a different chromophore was applied to hair.

Differently coloured cationic polymers were mixed in the same composition to obtain a shading of the colouration. The results are shown in FIG. 4.

The first and second compositions used in the experiments have been prepared as shown below.

| Ingredients | g/l |
|---|---|
| First Composition | |
| PEI-Reactive Red 180 | 2.50 (0.25 wt %) |
| PEI-Remazol Yellow | 2.50 (0.25 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

The weight mixing ratio in the above table is 1:1 (PEI-Reactive Red 180: PEI-Remazol Yellow), which corresponds to sample 9D. The following table gives the mixing ratio for each sample.

| Sample | Mixing ratio (weight) PEI-Reactive Red 180:PEI-Remazol Yellow |
|---|---|
| 9A | 4:1 |
| 9B | 3:1 |

| Sample | Mixing ratio (weight) PEI-Reactive Red 180:PEI-Remazol Yellow |
|---|---|
| 9C | 2:1 |
| 9D | 1:1 |
| 9E | 1:2 |
| 9F | 1:3 |
| 9G | 1:4 |

A hair swatch has been coloured according to the following protocol:
 (i) Preparing the first and second compositions shortly before application;
 (ii) Dipping the hair swatch into 4 mL of the first composition at 55° C. in a test tube;
 (iii) Agitating the first composition with the hair swatch for 15 min at 55° C. in a laboratory-type drying cabinet;
 (iv) Rinsing the hair swatch for 30 sec with fresh lukewarm tap water at a temperature of 30 to 35° C.;
 (v) Dipping the hair swatch into 4 mL of the second composition at 55° C. in a test tube;
 (vi) Agitating the second composition with the hair swatch for 15 min at 55° C. in a laboratory oven;
 (vii) Rinsing the hair swatch for 30 sec with fresh lukewarm tap water at a temperature of 30 to 35° C.;
 (viii) Repeating steps (ii) to (vii) a second time
 (ix) Drying the hair swatch first with tissue paper and then with a hair dryer.

III. Samples 10A to 10E, mixing of PEI-Remazol Blue and PEI-Reactive Red 180

Differently coloured cationic polymers were mixed in the same composition to obtain a shading of the colouration. The results are shown in FIG. 5.

Figure 5:
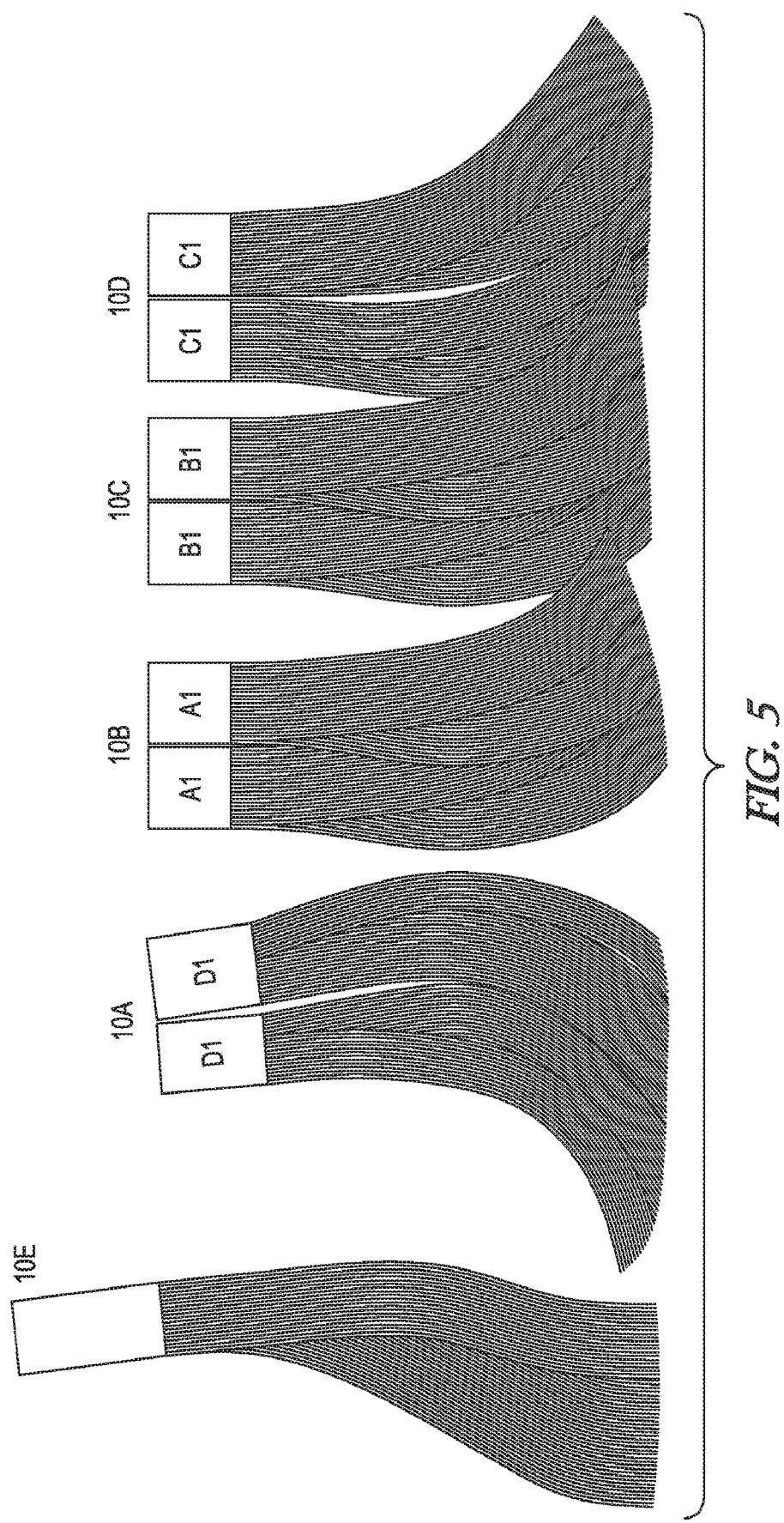
FIG. 5 illustrates samples prepared according to an embodiment of the invention, wherein a mixture of polymers each linked with a different chromophore was applied to hair.

The first and second compositions used in the experiments have been prepared as shown below with a varying mixing ratio for PEI-Remazol Blue and PEI-Reactive Red 180 to obtain the different coloration and shading as shown in FIG. 5. Sample 10E is a not-coloured reference sample.

| Ingredients | g/l |
|---|---|
| First Composition | |
| PEI-Remazol Blue | 2.50 (0.25 wt %) |
| PEI-Reactive Red 180 | 2.50 (0.25 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured according to the following protocol:
 (i) Preparing the first and second compositions shortly before application;
 (ii) Dipping the hair swatch into 4 mL of the first composition at 55° C. in a test tube;
 (iii) Agitating the first composition with the hair swatch for 15 min at 55° C. in a laboratory-type drying cabinet;
 (iv) Rinsing the hair swatch for 30 sec with fresh lukewarm tap water at a temperature of 30 to 35° C.;
 (v) Dipping the hair swatch into 4 mL of the second composition at 55° C. in a test tube;
 (vi) Agitating the second composition with the hair swatch for 15 min at 55° C. in a laboratory oven;
 (vii) Rinsing the hair swatch for 30 sec with fresh lukewarm tap water at a temperature of 30 to 35° C.;
 (viii) Repeating steps (ii) to (vii) a second time
 (ix) Drying the hair swatch first with tissue paper and then with a hair dryer.

IV. Samples 11A and 11B, mixing of PEI—ICI-Red and PEI-Everlight Blue

The samples of FIGS. 3 to 5 used anionic dyes (chromophores) that were linked to a cationic polymer. The samples 11A and 11B uses a mixture a first cationic polymer to which an anionic dye (Everlight Blue 3R) is linked and a second cationic polymer to which a cationic dye (ICI Red) is linked. Both coloured dyes are mixed in the first composition.

| Ingredients | g/l |
|---|---|
| First Composition | |
| PEI-ICI Red | 2.50 (0.25 wt %) |
| PEI-Everlight Blue | 2.50 (0.25 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| pH adjusted to 8 by adding 1.0 mol/l NaOH or 1.0 mol/l HCl | |

A hair swatch has been coloured according to the following protocol:
 (i) Preparing the first and second compositions shortly before application;
 (ii) Place hair swatch on plastic wrap or color wraps
 (iii) Work 5 mL of the first composition into the hair tress using a brush
 (iv) Agitating the first composition with the hair swatch for 15 min at 45° C. in a laboratory-type drying cabinet;
 (v) Rinsing the hair swatch for 30 s with running lukewarm tap water at a temperature of 30° C. to 35° C.;
 (vi) Place hair swatch on plastic wrap or color wraps
 (vii) Work 5 mL of the second composition into the hair tress using a brush
 (viii) Rinsing the hair swatch for 30 s with running lukewarm tap water at a temperature of 30° C. to 35° C.;
 (ix) Repeating steps (ii) to (vii) a second time.
 (x) Drying the hair swatch first with tissue paper and then with a hair dryer.

Figure 6:
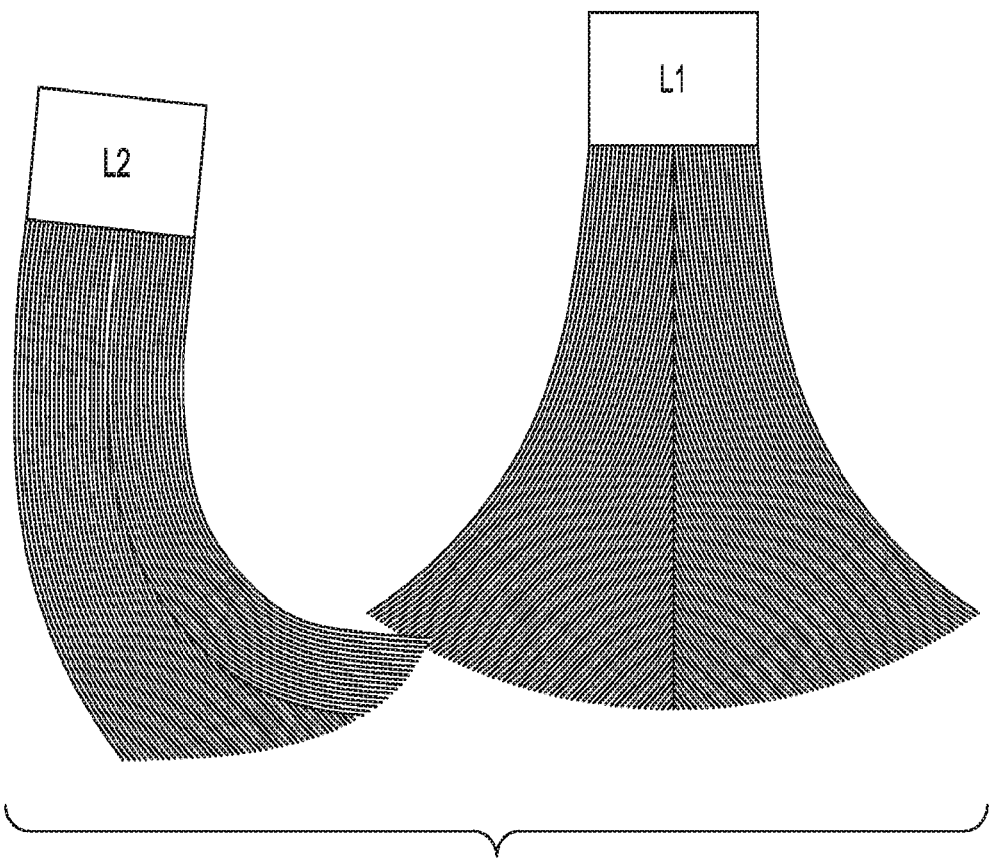
FIG. 6 illustrates samples prepared according to an embodiment of the invention, wherein different polymers each linked with a different chromophore were applied to hair.

The results for two different mixtures are illustrated in FIG. 6 showing that shading can also be obtained when using cationic and anionic dyes.

PEI-ICI Red can be synthesized as follows:
Fluoro-Diazonium Salt

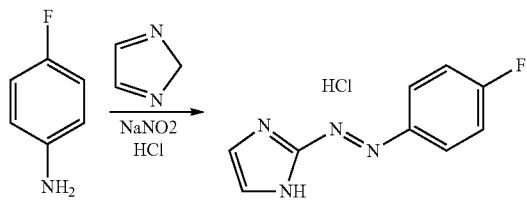

A three neck, 250 mL round bottom flask was charged with water (50 mL) and aqueous concentrated HCl (50 mL). The flask was equipped with a mechanical stirrer and cooled in a brine/dry ice bath. The internal temperature was 10-15° C. A separate vial was charged with 4-fluoroaniline (22.4097 g). The 4-fluoroaniline was added to the acid dropwise by pipette, maintaining an internal temperature of 20-27° C.

The flask was cooled with a cooling bath (external temperature between −5° C. and 0° C.). A solution of sodium nitrite (15.0498 g) in water (30 mL) was prepared. The dissolution was endothermic. The sodium nitrate solution was added dropwise by pipette over 7 minutes, maintaining an internal temperature of mostly below 5° C. (At one point the reaction was very briefly at a temperature of 7° C.). After the addition, the reaction was stirred at a temperature below 2° C. for 73 minutes. During this time, the external bath temperature was −5 to 0° C.

Sulfamic acid (5.4072 g) was added portionwise as a neat solid. The addition was done over 10 minutes. The mixture was stirred for an additional 50 minutes while being cooled. This will now be referred to as the diazo solution.

A different 1 L three neck flask was charged with imidazole (14.03 g) in water (300 mL). The flask was equipped with mechanical stirring and internal temperature/pH probes. Aqueous sodium hydroxide (12M) was added (1 mL). The pH reached 12. Concentrated HCl was added dropwise to get the pH back to 11. The imidazole mixture was then cooled to a temperature below 0° C. The bath temperature was −8° C. This will now be referred to as the imidazole solution. After stirring the diazo solution for 50 minutes, the stirring was stopped (cooling bath remained). The cold diazo solution and room temperature aqueous sodium hydroxide (12M) were added dropwise to the imidazole solution, maintaining a temperature below 0° C. and a pH between 8-12. After the start of the addition, the mixture in the 1 L flask was a yellow suspension. For most of the addition, the pH of the mixture in the 1 L flask was between 9-12. After the addition was complete the pH was adjusted to between 10-11. The total amount of sodium hydroxide added to the reaction was 36 mL. The addition took 55 minutes to complete. When the addition was complete, the mixture was a yellow orange suspension.

After the addition of the diazo solution the cooling bath was removed and the mixture was allowed to warm in room temperature air. After 60 minutes the internal temperature was 15° C. A water bath was then used to warm the reaction faster to 23° C. The reaction was stirred at 23° C. for 60 minutes total. The mixture was then filtered. The Buchner funnel was equipped with a Whatman GF/F filter. The solid was sticky, but easy to filter. The residual solids in the flask were rinsed into the funnel with water (2×50 mL). The filter cake was then washed with water (50 mL). The wet cake was allowed to sit overnight. The next day the mass of the cake was 100.14 g.

The wet solid was taken onto the next step.
Dimethylimidazolium Precursor

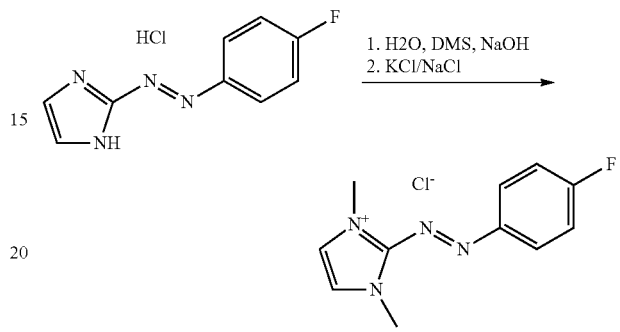

The crude, wet filter cake from the previous step was added to a 1 L, three neck round bottom flask.

The solid was rinsed in with water (500 mL). The mixture was stirred mechanically to yield a yellow suspension. The flask was equipped with pH and temperature probes. The internal temperature was 22° C. Sodium hydroxide (12M, aqueous) was added to the suspension. The pH was adjusted to 10.04 with concentrated HCl. A total of 5 mL of NaOH, 12M was added. The reaction mixture was a yellow suspension at 23° C. Three equivalents of dimethyl sulfate were added dropwise. During the dimethyl sulfate addition, the pH was maintained between 9.4-10.9 with 12M NaOH as necessary. By the time two equivalents of dimethyl sulfate had been added, there was a yellow/orange suspension in a red liquid. The temperature was then maintained between 22-26° C. and the pH between 9-11 with dropwise addition of 12M NaOH. At completion, the reaction mixture was a red brown solution. Sodium chloride (100.00 g) and potassium chloride (50.02 g) were added to the reaction. The mixture looked like a brown slush. After 10 minutes, the pH reached 8.80. The reaction was then cooled in a brine/dry ice bath (internal temperature 2° C., pH-7.76). The reaction was then let to stir for 42.5 hours. The pH was then 7.94. A saturated solution of NaCl/KCl was pre-prepared in a separate flask. This solution had 150 g of NaCl, 75 g of KCl, and was diluted to a total volume of 675 mL with water. The mixture was cooled in an ice bath while stirring. Just enough water was added to barely have haziness in the solution while stirring. The stirring was then stopped to allow the solids to settle to the bottom of the flask. The reaction was filtered. The temperature of the reaction before filtration was 21° C. There was dark red filtrate and a brown solid. The solid was filtered and air dried giving an orange solid.

The cake was then rinsed with 3-5° C. salt solution (2×100 mL). The solid cake was pressed down after the 2nd and 3rd rinse. The solid was light brown in color. The wet mass of the solid was 65.46 g. The solid was transferred to a round bottom flask and dried on high vacuum at 60° C. for 90 minutes. The dried solid mass was 43.20 g.

PEI-Cationic Red Polymer

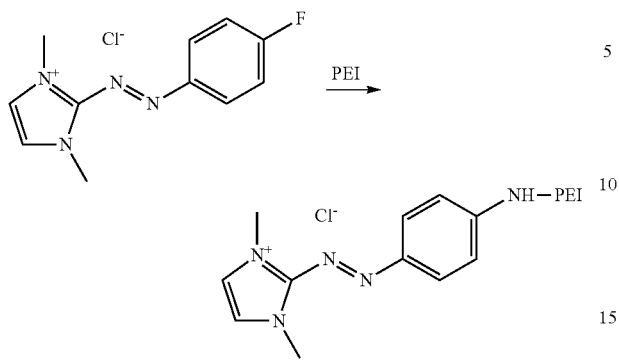

A reaction vessel was charged with 1 g of the solid from the previous step, 0.5 g of polyethyleneimine and 2.5 g of water, then heated at 60° C. for 16 hours. The reaction was cooled and the resulting viscous liquid was dissolved in water (7.5 mL; 60° C.) using sonication. The resulting solution was washed with dichloromethane (3×20 mL). Acetonitrile (80 mL) was added and the purplish reside that preciptitated was washed several additional times with acetonitrile. Methanol (40 mL) was added to the resulting purple residue and it was sonicated and to get an homogenous purple mixture. Concentrated HCl was added (1.1 mL), followed by acetone (120 mL) to precipitate the salt. Filtration and drying under vacuum gave 1 g of a dark red-purple solid which was used for dying experiments.

IX. Different Dyes Linked to Separate Anionic and Cationic Polymers of Different Polymeric Layers (Separate Polymeric Layers)

Synthesis Methods for Obtaining Anionic Coloured Polymers which May be Used in the Method According to the Present Invention:
 I. Branched polyethyleneimine labelled with modified Disperse Red 13:
  1. Starting materials:
   Dextran sulfate sodium salt, Mw=500,000 Da available from Sigma Aldrich (CAS: 9011-18-1)
   Disperse Red 13, available from Sigma Aldrich (CAS: 3180-81-2) N,N-Ethyldiisopropylamine available from Sigma Aldrich (CAS: 7087-68-5)
   3,3'-Iminobis(N,N-dimethylpropylamine) available from Sima Aldrich (CAS: 6711-48-4
   Cyanuric Chloride available from Sigma Aldrich (CAS: 108-77-0)
  2. Synthesis method:
   The following method has been used for labelling Dextran sulfate sodium salt (DxS) with Disperse Red13:
   1) Dissolving 0.523 g Disperse Red 13 and 628 μL N,N-Ethyldiisopropylamine in 13 ml Dichloromethane;
   2) Adding 668 mg Cyanurchloride after 5 min at 0° C.;
   3) Stirring the suspension at room temperature for 3 h;
   4) Evaporate the solvent and wash solid with water until neutral pH of washing solution collected supernatant to dryness;
   5) Drying the solid under reduced pressure;
   6) Dissolving 250 mg of the obtained solid in 7.5 ml Tetrahydrofuran,
   7) Adding 94 μl 3,3'-Iminobis(N,N-dimethylpropylamine) drop wise at room temperature;
   8) Stirring the solution at room temperature for 30 min;
   9) Evaporate the solvent, dissolve the residue in 10 ml Dichloromethan and wash the solution with 30 water three times;
   10) Evaporate the aqueous solution under reduced pressure to obtain activated Disperse Red 13;
   11) Dissolving 0.225 g Dextran sulfate in 10 ml water;
   12) Adding 132 mg activated Disperse Red 13 dissolved in 10 ml water;
   13) Agitating the reaction 2 h at 70° C.,
   14) Adding 0.5 mL N,N-Ethyldiisopropylamine
   15) Stirring the solution at room temperature for 12 h;
   16) Drying the solid and dissolving it in water;
   17) Dialyzing the resulting solution against water;
   18) Freeze-drying the product
 Cationic Coloured Polymers
 Cationic coloured polymers were coloured as described above.
  II. Layer combination of a cationic polymer coloured with an anionic dye and an anionic polymer coloured with an anionic dye.

| Ingredients | g/l |
|---|---|
| First Composition | |
| PEI-Reactive Red 180 | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| Dextran sulfate -Disperse Red 13 | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured according to the following protocol:
 (i) Preparing the first and second compositions shortly before application;
 (ii) Dipping the hair swatch into 4 mL of the first composition at 55° C. in a test tube;
 (iii) Agitating the first composition with the hair swatch for 15 min at 55° C. in a laboratory-type drying cabinet;
 (iv) Rinsing the hair swatch for 30 sec with fresh lukewarm tap water at a temperature of 30 to 35° C.;
 (v) Dipping the hair swatch into 4 mL of the second composition at 55° C. in a test tube;
 (vi) Agitating the second composition with the hair swatch for 15 min at 55° C. in a laboratory oven;
 (vii) Rinsing the hair swatch for 30 sec with fresh lukewarm tap water at a temperature of 30 to 35° C.;
 (viii) Repeating steps (ii) to (vii) a second time
 (ix) Drying the hair swatch first with tissue paper and then with a hair dryer.

The obtained results illustrated in FIG. 6 show that tailoring of the coloration is obtainable when combining differently coloured polymeric layers.

X. Examples of Methods According to the Present Invention Wherein Dialysed or Non-Dialysed PEI-Dye has been Used The following examples illustrate the effect of the polymer composition in terms of polymer weight distribution. The examples show that a coloured polymer being substantially free of coloured low molecular weight shows improved colouration results.

Example 10A

| Ingredients | g/l |
|---|---|
| First or Third Composition | |
| PEI | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) |
| pH adjusted to 8 by adding 1.0 mol/l NaOH or 1.0 mol/l HCl | |
| Second, Fourth or Sixth Composition | |
| DxS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) |
| pH adjusted to 8 by adding 1.0 mol/l NaOH or 1.0 mol/l HCl | |
| Fifth Composition | |
| PEI- 4B (Dialysed) | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5%) |
| pH adjusted to 8 by adding 1.0 mol/l NaOH or 1.0 mol/l HCl | |
| Removal Composition | |
| Na2HPO4 | 7.10 (0.05 mol/l) |
| pH was adjusted to 10.9 by adding 1.0 mol/l NaOH or 1.0 mol/l HCl | |

Step 1: Formation of the Polymeric Layer and the Coloured Layer on Top of the Polymeric Layer:
A hair swatch has been treated according to the following protocol:
  (i) Preparing the first to sixth compositions shortly before application;
  (ii) Applying 4 mL of the first composition to the hair swatch with a brush and wrapping the hair swatch with a commercial kitchen plastic wrap;
  (iii) Agitating the first composition with the hair swatch in plastic wrap for 15 min at 45° C. in a laboratory-type drying cabinet;
  (iv) Wiping the hair swatch with a paper towel;
  (v) Applying 4 mL of the second composition to the hair swatch with a brush and wrapping the hair swatch with a commercial kitchen plastic wrap;
  (vi) Agitating the second composition with the hair swatch in plastic wrap for 15 min at 45° C. in a laboratory-type drying cabinet;
  (vii) Wiping the hair swatch with a paper towel;
  (viii) Applying 4 mL of the third composition to the hair swatch with a brush and wrapping the hair swatch with a commercial kitchen plastic wrap;
  (ix) Agitating the third composition with the hair swatch in plastic wrap for 15 min at 45° C. in a laboratory-type drying cabinet;
  (x) Wiping the hair swatch with a paper towel;
  (xi) Applying 4 mL of the fourth composition to the hair swatch with a brush and wrapping the hair swatch with a commercial kitchen plastic wrap;
  (xii) Agitating the fourth composition with the hair swatch in plastic wrap for 15 min at 45° C. in a laboratory-type drying cabinet;
  (xiii) Wiping the hair swatch with a paper towel;
  (xiv) Applying 4 mL of the fifth composition to the hair swatch with a brush and wrapping the hair swatch with a commercial kitchen plastic wrap;
  (xv) Agitating the fifth composition with the hair swatch in plastic wrap for 15 min at 45° C. in a laboratory-type drying cabinet;
  (xvi) Wiping the hair swatch with a paper towel;
  (xvii) Applying 4 mL of the sixth composition to the hair swatch with a brush and wrapping the hair swatch with a commercial kitchen plastic wrap;
  (xviii) Agitating the sixth composition with the hair swatch in plastic wrap for 15 min at 45° C. in a laboratory-type drying cabinet;
  (xix) Rinsing the hair swatch for 30 s with running lukewarm tap water at a temperature of 30° C. to 35° C.;
  (xx) Drying the hair swatch first with tissue paper and then with a hair dryer.
Step 2: Removal of the Polymeric Layer
The hair swatch obtained at the end of step 1) has been then treated according to the following protocol:
  (i) Applying 5 ml of the removal composition to the coloured hair swatch with a brush for 30 s in a plastic bowl and letting the hair swatch soaked for 30 s;
  (ii) Rinsing the hair swatch for 30 s with running lukewarm tap water at a temperature of 30° C. to 35° C.;
  (iii) Drying the hair swatch first with tissue paper and then with a hair dryer.
  (iv) Repeating steps (i) to (iii) once more Example 10B A hair swatch has been treated as in example 10A except that the fifth composition has been replaced with the following fourth composition:

| Fifth Composition | |
|---|---|
| Ingredients | g/l |
| PEI- 4B (Non-Dialysed) | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5%) |
| pH adjusted to 8 by adding 1.0 mol/l NaOH or 1.0 mol/l HCl | |

L*, a*, b* Measurements
  The colorimetric parameters in the CIE L* a* b* system have been measured for each of the hair swatches obtained in Example 5A and 5B as described in the sets of experimental data as described above.
Results and Conclusions:
  The ΔE values obtained for the different examples are summarized in Table 1 below.

TABLE 1

| Example | Sequence of layers prior to removal | Low MW residues? | $\Delta E_{Stage2/Stage1}$[1] | $\Delta E_{Stage3/Stage1}$[2] |
|---|---|---|---|---|
| Example 10A | PEI/DxS/PEI/DxS/PEI-4B D/DxS | No | 31.47 | 4.03 |
| Example 10B | PEI/DxS/PEI/DxS/PEI-4B ND/DxS | Yes | 30.81 | 9.71 |

[1] corresponds to the overall change of colour measured between stage 2 and stage 1
[2] corresponds to the overall change of colour measured between stage 3 and stage 1

When comparing the ΔE values obtained for the different examples, it can be noticed that if the PEI-Dye is dialysed, $\Delta E_{Stage3/Stage1}$ value becomes lower. This shows that the amount of colour which is removed is much higher when the fifth composition includes dialysed PEI-Dye, in which the low MW residues, i.e. low molecular weight compounds, have been removed. Furthermore, also the colouration is slightly improved as evident from the $\Delta E_{Stage2/Stage1}$ value showing that the removal of low molecular weight compounds prevents unwanted reaction with the hair.

Combinations

A. A polymeric hair colouring formulation, comprising: at least two different chromophores and/or fluorophores linked to polymer(s), and optionally one or more uncoloured polymer(s).

B. A polymeric hair colouring formulation of paragraph A, wherein the formulation comprises at least one cationic coloured polymer having a cationic polymer-backbone and at least two different chromophores and/or fluorophores linked to the cationic polymer-backbone.

C. A polymeric hair colouring formulation of Paragraph A or B, wherein the formulation comprises at least one of:
(a) a mixture of at least a first cationic coloured polymer and a second cationic coloured polymer,
wherein the first cationic coloured polymer comprises a first cationic polymer-backbone to which at least a first chromophore and/or a first fluorophore is linked, and
wherein the second cationic coloured polymer comprises a second cationic polymer-backbone to which at least a second chromophore and/or a second fluorophore different to the first chromophore and/or fluorophore is linked;
and
(b) a mixture of at least a first anionic coloured polymer and a second anionic coloured polymer,
wherein the first anionic coloured polymer comprises a first anionic polymer-backbone to which at least a first chromophore and/or a first fluorophore is linked, and
wherein the second anionic coloured polymer comprises a second anionic polymer-backbone to which at least a second chromophore and/or a second fluorophore different to the first chromophore and/or fluorophore is linked.

D. A polymeric hair colouring formulation of any of the previous paragraphs, wherein the formulation comprises at least
a first composition comprising a first coloured polymer comprising a first polymer(s), to which at least a first chromophore and/or a first fluorophore is linked, and
a second composition comprising a second coloured polymer comprising a second polymer(s) to which at least a second chromophore and/or a second fluorophore different to the first chromophore and/or fluorophore is linked.

E. A polymeric hair colouring formulation of paragraph D, wherein
the first coloured polymer(s) is one of a first coloured cationic polymer and a first coloured anionic polymer, and
the second coloured polymer(s) is one of a second coloured cationic polymer and a second coloured anionic polymer.

F. A polymeric hair colouring formulation of any of the previous paragraphs, wherein at least one of the two different chromophores and/or fluorophores or at least one of the first or second chromophore and/or first or second fluorophore is an anionic chromophore and/or an anionic fluorophore which is linked to cationic polymer(s), or is a nonionic chromophore and/or a nonionic fluorophore which is linked to cationic polymer(s), or is a cationic chromophore and/or a cationic fluorophore which is linked to cationic polymer(s), or is an amphoteric chromophore and/or an amphoteric fluorophore which is linked to cationic polymer(s).

G. A polymeric hair colouring formulation of any of the previous paragraphs,
wherein one of the two different chromophores and/or fluorophores or one of the first or second chromophore and/or first or second fluorophore is a chromophore and/or fluorophore of a first type which is linked to the cationic polymer(s),
wherein the other one of the two different chromophores and/or fluorophores or the other one of the first or second chromophore and/or first or second fluorophore is a chromophore and/or fluorophore of a second type which is linked to cationic polymer(s),
wherein the first and second type are different from each other and are selected from anionic, cationic, nonionic, and amphoteric.

H. A polymeric hair colouring formulation of paragraph A, wherein the formulation comprises at least one anionic coloured polymer having an anionic polymer-backbone and two different chromophores and/or fluorophores linked to the anionic polymer-backbone.

I. A polymeric hair colouring formulation of paragraph H, wherein at least one of the two different chromophores and/or fluorophores is an anionic chromophore and/or an anionic fluorophore which is linked to the anionic polymer-backbone, or is a nonionic chromophore and/or a nonionic fluorophore which is linked to the anionic polymer-backbone, or is a cationic chromophore and/or a cationic fluorophore which is linked to the anionic polymer-backbone, or is an amphoteric chromophore and/or an amphoteric fluorophore which is linked to the anionic polymer-backbone.

J. A polymeric hair colouring formulation of any of the previous paragraphs, wherein a labelling degree of the respective coloured polymer(s) is between 1:3 to 1:50, particularly between 1:3 to 1:30, more particularly between 1:3 to 1:25.

K. A polymeric hair colouring formulation of any of the previous paragraphs, wherein the cationic polymer(s) of the coloured cationic polymer(s) comprises at least one monomer unit comprising at least one amino functional group, preferably wherein the amino functional group is selected from the group consisting of primary, secondary, tertiary, quatemary amino functional groups and mixtures thereof, more preferably wherein the amino functional group is selected from the group consisting of primary, secondary amino functional groups and mixtures thereof, even more preferably wherein the amino functional group is selected from secondary amino functional groups, wherein the cationic polymer(s) are particularly selected from the group consisting of polyethyleneimine, polyallylamine hydrochloride, polyvinylamine, copolymers thereof and mixtures thereof, preferably from the group consisting of polyethyleneimine, copolymers thereof and mixtures thereof.

L. The hair colouring formulation according to any of the preceding paragraphs, wherein the anionic polymer(s) of the coloured anionic polymer (s) is/are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and mixtures thereof, preferably from the group consisting of dextran sulfate salts, polystyrene sulfonate salts, polystyrene sulfonate/polystyrene copolymer salts, polystyrene sulfonate/maleic acid copolymers salts, copolymers thereof and mixtures thereof.

M. A method for colouring hair comprising:
applying any of the polymeric hair colouring formulations as defined in any of the paragraphs, to keratin fibres of hair to form one or more polymeric layers on the keratin fibres of the hair, so that the one or more polymeric layers comprises at least two different chromophores and/or fluorophores linked to polymer(s) of the one or more polymeric layers.

N. A method for colouring hair of paragraph M, wherein at least one, two or three of the following steps is carried out:
(i) applying a first composition comprising at least one uncoloured cationic polymer to a first portion of hair;
(ii) applying a second composition comprising at least one uncoloured anionic polymer to a second portion of the hair;
(iii) applying a third composition to a third portion of hair, wherein third composition comprises at least one of
a) a cationic coloured polymer having a cationic polymer-backbone and at least two different chromophores and/or fluorophores linked to the cationic polymer-backbone, and
b) a mixture of at least a first cationic coloured polymer and a second cationic coloured polymer, wherein the first cationic coloured polymer comprises a first cationic polymer-backbone to which at least a first chromophore and/or fluorophore is linked, and wherein the second cationic coloured polymer comprises a second cationic polymer-backbone to which at least a second chromophore and/or fluorophore different to the first chromophore and/or fluorophore is linked;
(iv) applying a fourth composition to a fourth portion of the hair, wherein the fourth composition comprises at least one of
a) an anionic coloured polymer having an anionic polymer-backbone and at least two different chromophores and/or fluorophores linked to the anionic polymer-backbone, and
b) a mixture of at least a first anionic coloured polymer and a second anionic coloured polymer, wherein the first anionic coloured polymer comprises a first anionic polymer-backbone to which at least a first chromophore and/or fluorophore is linked, and wherein the second anionic coloured polymer comprises a second anionic polymer-backbone to which at least a second chromophore and/or fluorophore different to the first chromophore and/or fluorophore is linked;
wherein the first, second, third and fourth portion have at least one common area.

O. A method for manufacturing a polymeric hair colouration composition for hair coloration, the method comprising:
(1) providing at least one of anionic polymer(s) and cationic polymer(s); and
(2) linking at least two different chromophores and/or fluorophores to the at least one of anionic polymer(s) and cationic polymer(s).

P. A method for manufacturing a polymeric hair colouration composition for hair coloration, the method comprising:
(1) providing at least first and second polymer(s) each having a polymer back-bone;
(2) linking at least a first chromophore and/or a first fluorophore to the polymer back-bone of the first polymer(s) to form a first composition comprising first coloured polymer(s);
(3) linking at least a second chromophores and/or a second fluorophores to the polymer back-bone of the second polymer(s) to form a second composition comprising second coloured polymer(s); and
(4) mixing the first and second composition to form the polymeric hair colouration composition,
(5) wherein the first and second polymer(s) both are either anionic or cationic.

Q. Use of a polymeric hair colouration formulation to provide hair colouration, wherein the polymeric hair colouration formulation comprises at least one of:
a first composition comprising one or more polymer(s) to which at least two different chromophores and/or fluorophores are linked;
a first composition comprising a mixture of at least first polymer(s), to which at least a first chromophore and/or a first fluorophore is linked, and at least second polymer(s) to which at least a second chromophore and/or second fluorophores different to the first chromophore and/or first fluorophore is linked, wherein the first and second polymer(s) are both either anionic or cationic; and
a first composition comprising at least first polymer(s), to which at least a first chromophore and/or a first fluorophore is linked, and a second composition comprising at least second polymer(s) to which at least a second chromophore and/or second fluorophores different to the first chromophore and/or first fluorophore is linked.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A polymeric hair colouring formulation, comprising:
at least two different chromophores and/or fluorophores linked to polymer(s), wherein the formulation comprises at least one of:
(a) a mixture of at least a first cationic coloured polymer and a second cationic coloured polymer,
wherein the first cationic coloured polymer comprises a first cationic polymer-backbone to which at least a first chromophore and/or a first fluorophore is linked, and
wherein the second cationic coloured polymer comprises a second cationic polymer-backbone to which at least a second chromophore and/or a second fluorophore different to the first chromophore and/or fluorophore is linked; and
(b) a mixture of at least a first anionic coloured polymer and a second anionic coloured polymer,
wherein the first anionic coloured polymer comprises a first anionic polymer-backbone to which at least a first chromophore and/or a first fluorophore is linked, and
wherein the second anionic coloured polymer comprises a second anionic polymer-backbone to which at least a second chromophore and/or a second fluorophore different to the first chromophore and/or fluorophore is linked
and
optionally one or more uncoloured polymer(s).

2. A polymeric hair colouring formulation of claim 1, wherein at least one of the two different chromophores and/or fluorophores or at least one of the first or second chromophore and/or first or second fluorophore is an anionic chromophore and/or an anionic fluorophore which is linked to cationic polymer(s), or is a nonionic chromophore and/or a nonionic fluorophore which is linked to cationic polymer(s), or is a cationic chromophore and/or a cationic fluorophore which is linked to cationic polymer(s), or is an amphoteric chromophore and/or an amphoteric fluorophore which is linked to cationic polymer(s).

3. A polymeric hair colouring formulation of claim 1, wherein one of the two different chromophores and/or fluorophores or one of the first or second chromophore and/or first or second fluorophore is a chromophore and/or fluorophore of a first type which is linked to the cationic polymer(s),
wherein the other one of the two different chromophores and/or fluorophores or the other one of the first or second chromophore and/or first or second fluorophore is a chromophore and/or fluorophore of a second type which is linked to cationic polymer(s),
wherein the first and second type are different from each other and are selected from anionic, cationic, nonionic, and amphoteric.

4. A polymeric hair colouring formulation of claim 1, wherein the formulation comprises at least one anionic coloured polymer having an anionic polymer-backbone and two different chromophores and/or fluorophores linked to the anionic polymer-backbone.

5. A polymeric hair colouring formulation of claim 4, wherein at least one of the two different chromophores and/or fluorophores is an anionic chromophore and/or an anionic fluorophore which is linked to the anionic polymer-backbone, or is a nonionic chromophore and/or a nonionic fluorophore which is linked to the anionic polymer-backbone, or is a cationic chromophore and/or a cationic fluorophore which is linked to the anionic polymer-backbone, or is an amphoteric chromophore and/or an amphoteric fluorophore which is linked to the anionic polymer-backbone.

6. A polymeric hair colouring formulation of claim 1, wherein the respective coloured polymer(s) has a labeling degree between 1:3 to 1:50.

7. A polymeric hair colouring formulation of claim 1, wherein the cationic polymer(s) of the coloured cationic polymer(s) comprises at least one monomer unit comprising at least one amino functional group.

8. The hair colouring formulation according to claim 1, wherein the anionic polymer(s) of the coloured anionic polymer (s) is/are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and mixtures thereof.

9. A method for colouring hair comprising:
applying any of the polymeric hair colouring formulations as defined in claim 1 to keratin fibres of hair to form one or more polymeric layers on the keratin fibres of the hair, so that the one or more polymeric layers comprises at least two different chromophores and/or fluorophores linked to polymer(s) of the one or more polymeric layers.

10. A method for colouring hair of claim 9, wherein at least one, two or three of the following steps is carried out:
(i) applying a first composition comprising at least one uncoloured cationic polymer to a first portion of hair;
(ii) applying a second composition comprising at least one uncoloured anionic polymer to a second portion of the hair;
(ii) applying a third composition to a third portion of hair, wherein third composition comprises
a mixture of at least a first cationic coloured polymer and a second cationic coloured polymer, wherein the first cationic coloured polymer comprises a first cationic polymer-backbone to which at least a first chromophore and/or fluorophore is linked, and wherein the second cationic coloured polymer comprises a second cationic polymer-backbone to which at least a second chromophore and/or fluorophore different to the first chromophore and/or fluorophore is linked;

(iv) applying a fourth composition to a fourth portion of the hair, wherein the fourth composition comprises a mixture of at least a first anionic coloured polymer and a second anionic coloured polymer, wherein the first anionic coloured polymer comprises a first anionic polymer-backbone to which at least a first chromophore and/or fluorophore is linked, and wherein the second anionic coloured polymer comprises a second anionic polymer-backbone to which at least a second chromophore and/or fluorophore different to the first chromophore and/or fluorophore is linked;

wherein the first, second, third and fourth portion have at least one common area.

11. A method for manufacturing a polymeric hair colouration composition for hair coloration, the method comprising:
(1) providing at least first and second polymer(s) each having a polymer back-bone;
(2) linking at least a first chromophore and/or a first fluorophore to the polymer back-bone of the first polymer(s) to form a first composition comprising first coloured polymer(s);
(3) linking at least a second chromophores and/or a second fluorophores, which are different from the first chromophore and/or fluorophore, to the polymer back-bone of the second polymer(s) to form a second composition comprising second coloured polymer(s); and
(4) mixing the first and second composition to form the polymeric hair colouration composition,
(5) wherein the first and second polymer(s) both are either anionic or cationic.

* * * * *